(12) United States Patent
De Vivo et al.

(10) Patent No.: US 10,889,560 B2
(45) Date of Patent: Jan. 12, 2021

(54) 4-AMINO-2-PYRIDO-BICYCLIC PYRIMIDINES AND USE THEREOF AS TOPOISOMERASE II INHIBITORS

(71) Applicants: FONDAZIONE ISTITUTO ITALIANO DI TECNOLOGIA, Genoa (IT); ALMA MATER STUDIORUM—UNIVERSITA' DI BOLOGNA, Bologna (IT); UNIVERSITA' DEGLI STUDI DI PADOVA, Padua (IT)

(72) Inventors: Marco De Vivo, Genoa (IT); Jose Antonio Ortega Martinez, Genoa (IT); Jose Manuel Arencibia Jimenez, Genoa (IT); Anna Minarini, Bologna (IT); Claudia Sissi, Cadoneghe (IT)

(73) Assignees: UNIVERSITÀ DEGLI STUDI DI PADOVA, Padua (IT); ALMA MATER STUDIORUM-UNIVERSITÀ DI BOLOGNA, Bologna (IT); FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 16/472,593

(22) PCT Filed: Dec. 15, 2017

(86) PCT No.: PCT/EP2017/083087
§ 371 (c)(1),
(2) Date: Jun. 21, 2019

(87) PCT Pub. No.: WO2018/114700
PCT Pub. Date: Jun. 28, 2018

(65) Prior Publication Data
US 2019/0315709 A1    Oct. 17, 2019

(30) Foreign Application Priority Data
Dec. 23, 2016   (IT) .................. 102016000130706

(51) Int. Cl.
| | |
|---|---|
| C07D 401/04 | (2006.01) |
| A61K 33/243 | (2019.01) |
| A61K 31/167 | (2006.01) |
| A61K 31/282 | (2006.01) |
| A61K 31/337 | (2006.01) |
| A61K 31/357 | (2006.01) |
| A61K 31/407 | (2006.01) |
| A61K 31/4745 | (2006.01) |
| A61K 31/475 | (2006.01) |
| A61K 31/513 | (2006.01) |
| A61K 31/517 | (2006.01) |
| A61K 31/519 | (2006.01) |
| A61K 31/655 | (2006.01) |
| A61K 31/704 | (2006.01) |

(Continued)

(52) U.S. Cl.
CPC .......... *C07D 401/04* (2013.01); *A61K 31/167* (2013.01); *A61K 31/282* (2013.01); *A61K 31/337* (2013.01); *A61K 31/357* (2013.01); *A61K 31/407* (2013.01); *A61K 31/475* (2013.01); *A61K 31/4745* (2013.01); *A61K 31/513* (2013.01); *A61K 31/517* (2013.01); *A61K 31/519* (2013.01); *A61K 31/655* (2013.01); *A61K 31/704* (2013.01); *A61K 31/706* (2013.01); *A61K 31/7076* (2013.01); *A61K 33/243* (2019.01); *C07D 471/04* (2013.01)

(58) Field of Classification Search
CPC .................................................... C07D 401/04
See application file for complete search history.

(56) References Cited

U.S. PATENT DOCUMENTS

| | | | |
|---|---|---|---|
| 2002/0025968 A1 | 2/2002 | Pamukcu et al. | |
| 2010/0069383 A1 | 3/2010 | Anderson et al. | |

FOREIGN PATENT DOCUMENTS

| | | |
|---|---|---|
| WO | 2010/019637 A1 | 2/2010 |
| WO | 2015/112739 A1 | 7/2015 |

OTHER PUBLICATIONS

International Search Report and Written Opinion for corresponding Application No. PCT/EP2017/083087 (dated Mar. 21, 2018).

(Continued)

*Primary Examiner* — Brian E McDowell
(74) *Attorney, Agent, or Firm* — Troutman Pepper Hamilton Sanders LLP (Rochester)

(57) ABSTRACT

The present invention concerns 4-amino-2-pyrido-bicyclic pyrimidines of Formula (I)

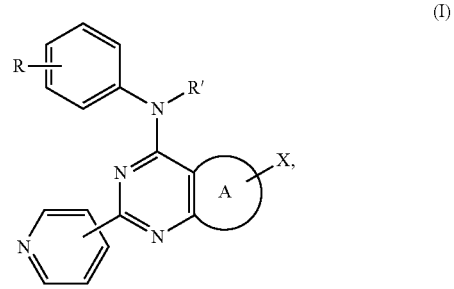

that function as type II topoisomerase inhibitors and their use thereof as medicaments especially in the treatment of cancer. The invention also provides a method for the manufacture of 4-amino-2-pyrido bicyclic pyrimidines of Formula (I).

3 Claims, No Drawings

(51) Int. Cl.
*A61K 31/706* (2006.01)
*A61K 31/7076* (2006.01)
*C07D 471/04* (2006.01)

(56) References Cited

OTHER PUBLICATIONS

CAS Registry Nos. 1381533-07-8; 1381664-75-0; 1381255-39-5; 1381354-68-2; 1381622-08-7; 1381426-41-0; 1381314-22-2; 1381286-96-9;1381331-68-5; 1381675-88-2; 1381487-17-7; 1381462-67-4 from Chemical Abstracts Service: Columbus, Ohio (Mar. 22, 2016).
Wasfy et al., "Synthesis and Anti-Cancer Properties of Novel Quinazoline Derivatives," Internat. J. Res. Pharm. Chem. 5(1):34-40 (2015).

4-AMINO-2-PYRIDO-BICYCLIC PYRIMIDINES AND USE THEREOF AS TOPOISOMERASE II INHIBITORS

This application is a national stage application under 35 U.S.C. § 371 of PCT Application No. PCT/EP2017/083087, filed Dec. 15, 2017, which claims the priority benefit of Italy Patent Application No. 102016000130706, filed Dec. 23, 2016.

FIELD OF THE INVENTION

The present invention concerns with 4-amino-2-pyrido-bicyclic pyrimidines as type II topoisomerase inhibitors and use thereof as medicaments.

Specifically, the present invention is related to a family of selected 4-amino-2-pyrido bicyclic pyrimidines that inhibit human type II topoisomerase enzyme and that are useful as anticancer agents.

BACKGROUND OF THE INVENTION

Topoisomerases are enzymes that modulate the topological state of DNA in the cell. This activity is performed by introducing transient breaks in the DNA strand, thus catalyzing DNA unwinding, an essential step in, for example, transcription and replication (Nitiss, 2009).

Topoisomerases are classified in two major classes, type I and II, based on the number DNA strands that they cleave and on their mechanism of action (Deweese and Osheroff, 2009). Type II topoisomerases, also known as topo II, are essential for cell survival and play vital roles in virtually every nucleic acid process, including DNA replication, transcription, and recombination. They also are required for proper chromosome organization and segregation as discussed by Pendelton et al., 2014 Human topo II enzymes are essential for DNA topology modification, and represent a validated drug target to treat cancer. Several classes of topo II drugs have been developed over the last few decades.

It is known that epipodopodophyllotoxin compounds, like etoposide, are used to treat lung cancer, choriocarcinoma, ovarian and testicular cancers, lymphoma, and acute myeloid leukemia. Other members of topoisomerase inhibitors belonging to this group, like the drug teniposide, are approved by the Health Authorities for the treatment of central nervous system tumors, malignant lymphoma, and bladder cancer.

Another wide class of topoisomerase inhibitors is represented by anthracyclines, which are used for the treatment of many different types of solid tumors and hematologic cancers. Moreover, the use of anthraquinones in the treatment of advanced prostate cancer and in certain forms of leukemia is also known. Acridines are a further family of compounds that finds application in the treatment of leukemia (for a comprehensive review on these chemical classes, see Bailly C. Chem Rev. 2012).

Although the availability of several topoII inhibitors, drug resistance and severe side effects related to topoII-targeted drugs demand the discovery of novel and safer topoII inhibitors, toward better anticancer therapeutics as evidenced by Mayer, C. and Janin, Y.-L., in Chemmical Reviews, 2014, 114 (4), 2313-2342.

An explored strategy for cancer therapy was to target topo II with molecule inhibitors. These are grouped into several classes like, for examples, poisons, which increase the levels of topo II covalently bound to the DNA, and catalytic inhibitors, which bind to the catalytic site of topo II (Nitiss, 2009). Importantly, there are several drugs that target topo II and that are regularly used in the clinics for the treatment of several types of cancer including prostate and lung cancers (Chen et al., 2015).

In the scientific article "syntheses of 2,4,6-trisubstituted pyrimidine derivatives as a new class of antifilarial topoisomerase II inhibitors", the authors Katiyar et al. disclose the synthesis of series of 21 compounds of trisubstituted pyrimidine derivatives and their evaluation for the in vitro topo II inhibitory activity against filarial parasite *Setaria cervi*. Out of these, seven compounds (8, 11-14, 25 and 28) have shown 60-80% inhibition at 40 and 20 lg/mL concentration. Five compounds (12, 13, 14, 25 and 28) exhibited 70-80% inhibition at 10 lg/mL concentration and three compounds (13, 14 and 28) have shown 40-60% inhibition at 5 lg/mL concentration. All the above-mentioned compounds have shown better topo II inhibitory activity than standard antifilarial drug (DEC) and enzyme topo II inhibitors (Novobiocin, Nalidixic acid).

A major shortcoming of drugs that target topo II and that are used in the clinics, however, is their elevated toxicity and the appearance of drug-resistance.

Fused pyrimidines compounds having a saturated, unsaturated or aromatic A ring fused to a pyrimidine ring and having a complex substituent at the 2 position and a substituted amine at the 4 position of the pyrimidine ring as well as optional aliphatic, functional and/or aromatic components substituted at other positions of the pyrimidine ring and A ring are also disclosed in the application WO 2014/015291. The authors discovered that these compounds are inhibitors of the AAA proteasome complex containing p97 and tested then as medicinal agents for treatment of diseases associated with p97 bioactivity.

Therefore, at present there is an urgent and unmet medical need for novel and safer topo II inhibitors for the treatment of cancer.

One of the objects of the present invention is therefore to provide compounds acting as potent inhibitors of human type II topoisomerase (topo II) enzymes, showing also potent inhibition of cancer cells proliferation.

SUMMARY OF THE INVENTION

The inventors have found that a family of selected compounds which have a 4-amino-2-pyrido-bicyclic-pyrimidine scaffold are potent inhibitors towards human type II topoisomerase (topo II) enzymes and are effective in blocking the proliferation of cancer cells.

Accordingly, in one aspect the present invention provides a compound having the formula (I)

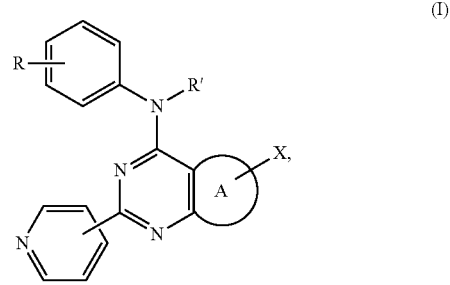

an enantiomer, or a pharmaceutically acceptable salt thereof, wherein

R=H, halogen, preferably F, $C_{1-6}$ alkyl, $C_{1-6}$ alkoxy, OH, $CF_3$, NR"R"';
R'=H, $C_{1-6}$ alkyl;

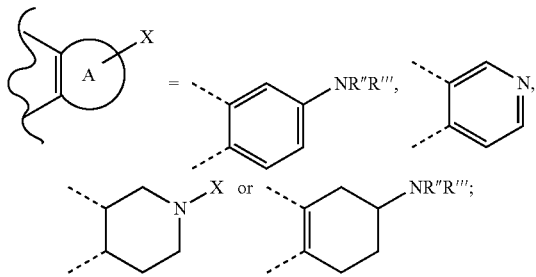

X=H, $C_{1-6}$ alkyl, $C_{1-6}$ alkoxy, $C_{1-6}$ alkylalkoxy, NR"R"', $C_1$-$C_6$ alkylamide.

R"R"' are, independently, H, $C_{1-6}$ alkyl, $C_{1-6}$ alkyloxy or may form a 4 to 7-membered heterocyclic ring together with the nitrogen atom to which they are connected, for use in treating cancer.

In accordance with a second aspect, the present invention provides compounds of Formula (Ia)

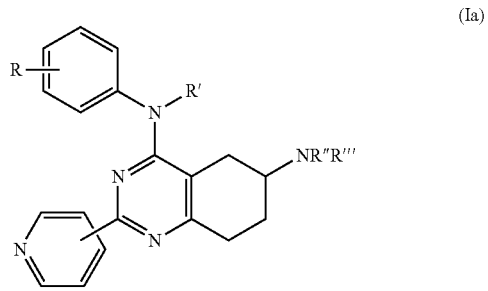

(Ia)

wherein R=H, halogen, $C_{1-6}$ alkyl, $C_{1-6}$ alkoxy, OH, $CF_3$, NR"R"' and

R'=H, $C_{1-6}$ alkyl;

R"R"' are, independently, H, $C_{1-6}$ alkyl, $C_{1-6}$ alkylalkoxy or may form a 4 to 7-membered heterocyclic ring together with the nitrogen atom to which they are connected.

In accordance with a third aspect, the present invention provides compounds of Formula (Ib) having the formula

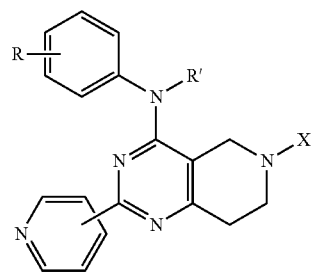

(Ib)

wherein R=H, halogen, $C_{1-6}$ alkyl, $C_{1-6}$ alkoxy, OH, $CF_3$, NR"R"' and

R'=H, $C_{1-6}$ alkyl;

X is H, $C_{1-6}$ alkyl, $C_{1-6}$ alkylalkoxy, $C_{1-6}$ alkylamide.

In accordance with a fourth aspect, the present invention provides a method for the treatment of cancer in a subject comprising the administration of an effective amount of a compound of the above formula (I), (Ia), (Ib) or a pharmaceutically acceptable salt thereof, wherein the cancer is treatable with a type II topoisomerase (topo II) inhibitor.

The present invention also describes methods the preparation of the above compounds of formula (I), (Ia), (Ib).

In a yet further aspect, the present invention relates to pharmaceutical compositions comprising a compound of formula (I), (Ia), (Ib) and a pharmaceutically acceptable vehicle or excipient.

DETAILED DESCRIPTION OF THE INVENTION

The present invention origins from the finding that compounds having a fused two rings scaffold having 2-pyrido-4-amino substituted-pyrimidine as one of the rings and a six-membered saturated or unsaturated carbocyclic, or heterocyclic ring having up to 2 nitrogen atoms as the other ring fused to the 2,4-pyrimidine ring, have a specific inhibitory activity against human type II topoisomerase (topo II) enzyme making the compounds effective in the treatment of cancerous forms.

The pyrimidine scaffold of the compounds of the invention has a pyridinyl substituent at position 2 and an amine substituent at position 4.

I. Medical Uses of Compounds of Formula (I)

According to a first aspect, compounds of formula (I) are provided for use in the treatment of cancer,

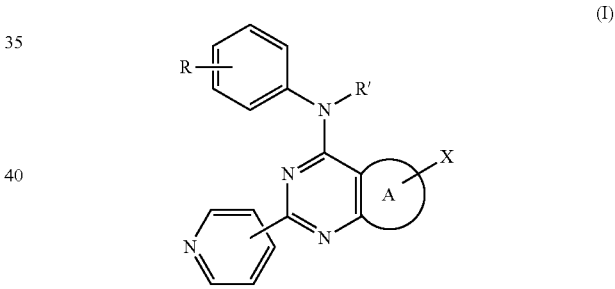

(I)

wherein

R=H, halogen, $C_{1-6}$ alkyl, $C_{1-6}$ alkoxy, OH, $CF_3$, NR"R"';

R'=H, $C_{1-6}$ alkyl;

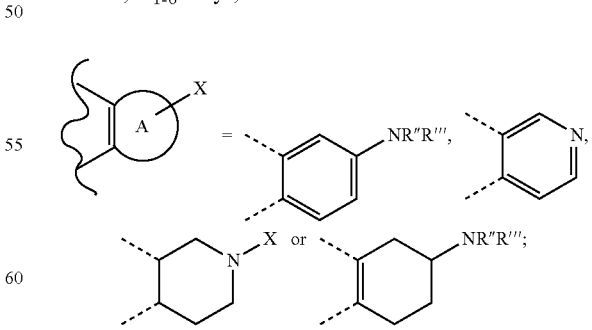

X=H, $C_{1-6}$ alkyl, $C_{1-6}$ alkoxy, $C_{1-6}$ alkylalkoxy, NR"R"';

R"R"' are, independently, H, $C_{1-6}$ alkyl, or may form a 4 to 7-membered heterocyclic ring together with the nitrogen atom to which they are connected.

In certain embodiments the scaffold

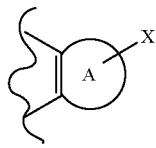

is selected from:

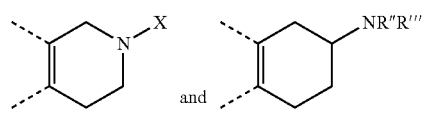

wherein X and R"R'" are as defined above.

According to certain embodiments the saturated six-membered heterocyclic ring is piperidine.

According to certain embodiments the unsaturated six-membered heterocyclic ring is pyridine.

In accordance with certain embodiments, the six-membered carbocyclic ring is a saturated carbocyclic ring.

For example, the six-membered heterocyclic ring having up to 2 nitrogen atoms may be pyridazine, pyrimidine, or pyrazine.

Specific compounds for use in the treatment of cancer are defined in claim 2, 3. Compounds having formula (I) which are preferred in the treatment of cancer are N4-(3-fluorophenyl)-2-(4-pyridyl)quinazoline-4,6-diamine (E3) or N-(3-fluorophenyl)-2-(4-pyridyl)pyrido[4,3-d]pyrimidin-4-amine (E4).

In accordance with certain embodiments the compounds of formula (I) for use in the treatment of cancer have the selected formula (Ia) or (Ib) as defined herein below.

II. Subset of Compounds of Formula (Ia)

In accordance with a second aspect of the present invention, the inventors have found that the compounds of Formula (I):

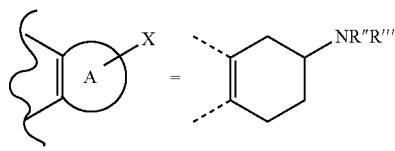

wherein the scaffold has a very effective inhibitory activity against human type II topoisomerase (topo II) enzyme and are effective in the treatment of cancer.

In accordance with this second aspect, the invention provides compounds of the formula (Ia) for use in the treatment of cancer

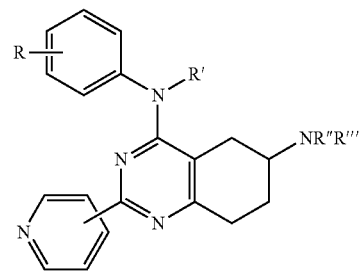

wherein R=H, halogen, $C_{1-6}$ alkyl, $C_{1-6}$ alkoxy, OH, $CF_3$, NR"R'" and
R'=H, $C_{1-6}$ alkyl;
R"R'" are, independently, H, $C_{1-6}$ alkyl, $C_1$-$C_6$ alkylalkoxy or may form a 4 to 7-membered heterocyclic ring together with the nitrogen atom to which they are connected.

In accordance with certain embodiments R"R'" are H.

In accordance with the above and additional embodiments R' is H.

In a further aspect, the present invention concerns the compound of formula (Ia) as specifically defined in anyone of claims 8 to 10.

III. Subset of Compounds of Formula (Ib)

In accordance with a third aspect of the present invention, the inventors have found that also compounds of Formula (I) wherein the scaffold

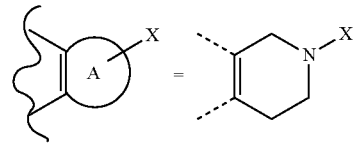

has a very effective inhibitory activity against human type II topoisomerase (topo II) enzyme.

In accordance with this third aspect, compounds are provided having the formula (Ib)

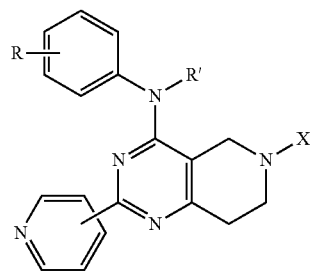

wherein R=H, halogen, $C_{1-6}$ alkyl, $C_{1-6}$ alkoxy, OH, $CF_3$, NR"R'" and
R'=H, $C_{1-6}$ alkyl;
X is H, $C_{1-6}$ alkyl, $C_{1-6}$ alkylalkoxy.

In accordance with certain embodiments X is H.

In accordance with the above and additional embodiments R' is H.

According to certain embodiments, in the compounds of formula I, Ia or Ib, the substituent R is an halogen selected from fluorine or chlorine, methyl, methoxy, OH, $CF_3$ or NR"R"', wherein R"R"' are, independently, H, methyl, or may form a 4 to 7-membered heterocyclic ring together with the nitrogen atom to which they are connected.

In a further aspect, the present invention concerns the compound of formula (Ib) as specifically defined in claim 11 or claim 12.

Common Embodiments of the Compounds of Formulae (I), (Ia), (Ib)

According to certain embodiments, in the compounds of formula I, Ia or Ib, the substituent R' is H or methyl.

According to certain embodiments, in the compounds of formula I, Ia or Ib, the substituent X is H, methyl, $C_{1-6}$ alkylalkoxide, such as $CH_2OCH_3$, or NR"R"', wherein R"R"' are, independently, H, methyl, or may form a 4 to 7-membered heterocyclic ring together with the nitrogen atom to which they are connected.

IV. Medical Uses of Compounds of Formula (Ia) and (Ib)

In accordance with another aspect of the present invention compounds of Formula Ia or Ib are provided for use as a medicament.

In accordance with an additional aspect, the present invention provides the compounds of Formula (Ia) and (Ib) for inhibiting the activity of type II topoisomerase (topo II) enzymes and therefore are effective in blocking the proliferation of cancer cells.

In some embodiments, the compounds of Formula (Ia), (Ib) and their pharmaceutical compositions and methods of administering them, are useful in treating diseases or disorders involving increased, type II topoisomerase (topo II) enzymatic activity, compared to physiological.

The treatment with the compounds of the invention may be prophylactic or therapeutic.

The subject to be treated may be an animal (e.g., mouse, rat, non-human primate and non-human mammal) or human.

The treatment may or may not be administered in a combination therapy with another anticancer agent.

The diseases and disorders which may be treated with the compounds of the invention include, but are not limited to, primary and metastatic neoplastic diseases or, in general, involving cell overproliferation, inflammatory related conditions or pain.

Diseases and disorders involving cell overproliferation include, but are not limited to, pre-malignant conditions, for example hyperplasia, metaplasia or dysplasia, cancers, cancer metastasis, benign tumors, hyperproliferative disorders and benign dysproliferative disorders.

Primary and metastatic neoplastic diseases and related disorders that can be treated and/or prevented by the methods, compounds and compositions of the presently disclosed subject matter include, but are not limited to prostate and lung cancer, colorectal cancer, liver cancer, prostate cancer, head and neck cancer, breast cancer, choriocarcinoma, ovarian and testicular cancers, lymphoma, and acute myeloid leukemia, central nervous system tumors, malignant lymphoma and bladder cancer, metastatic melanoma, precancerous skin conditions such as actinic keratosis, skin cancers such as squamous cell carcinoma and basal cell carcinoma, and hematological malignancies such as chronic myelogeneous leukemia.

In some embodiments, the compounds of Formula (Ia) or/and (Ib), and their pharmaceutical compositions and methods of administering them, are useful in treating or preventing a disease or disorder when administered in combination with other treatments.

In an additional aspect the present invention also concerns combination therapies or treatment with a compound of formula (Ia), (Ib) or pharmaceutical composition containing them.

In some embodiments, the compounds of Formula (Ia) and (Ib) and their pharmaceutical compositions and methods of administering them, are useful in treating various cancers when administered in combination with other pharmacological agents or active ingredients.

In certain embodiments, these pharmacological agents are chemotherapeutic agents including, but not limited to, doxorubicin, daunorubicin, etoposide, cisplatin, oxaliplatin, carboplatin, gemcitabine, 5-fluorouracil, capecitabine, tegafururacil (UFT), dacarbazine, fenretinide, camptothecin, irinotecan, fludarabine, vinblastine, taxol, mitomycin C.

In some embodiments, the compounds of Formula (I), and their pharmaceutical compositions and methods of administering them, are useful in treating various cancers when administered before, during or after patient's treatment with radiation therapy.

V. Pharmaceutically Acceptable Salts

It will be understood that, as used herein, references to the compounds of Formula (I), (Ia) or (Ib) are meant to include also the pharmaceutically acceptable salts or derivatives thereof.

Furthermore, the compound of the formula (I), (Ia) and (Ib) may form an acid addition salt or a salt with a base, depending on the kind of the substituents, and these salts are included in the present invention, as long as they are pharmaceutically acceptable salts.

The terms "the compound of the invention" and "the compounds of the present invention" and "the compounds of Formula (I)" refer to each of the compounds of Formulae (I), (Ia) or (Ib) and are meant to include their pharmaceutically acceptable salts, hydrates, solvates, and crystalline forms and also any suitable forms as illustrated hereinafter.

As used herein, the term "salt" refers to any salt of a compound according to the present invention prepared from an inorganic or organic acid or base and internally formed salts. Typically, such salts have a physiologically acceptable anion or cation. Suitably physiologically or pharmaceutically acceptable salts of the compounds of the present invention include the hydrochloride, acetate, hydrobromide, sulfate, phosphate, methane or ethane sulfonate, acetate, citrate, gluconate, lactate, tartrate, phosphate, borate, maleate, oxalate, succinate, fumarate benzoate, salicylate, phenylacetate, or mandelate, sulphate and nitrate, the hydrochloride being preferred.

Alternatively, the salt may be a salt of a metal which typically is selected from the IA or IIA groups of the periodic table of elements.

The salts of compounds of Formula (I), (Ia) and (Ib), may be prepared by reacting a basic compound with the desired acid in solution.

Physiologically or pharmaceutically acceptable salts are particularly suitable for medical applications because of their greater aqueous solubility relative to the parent compounds.

Pharmaceutical acceptable salts may also be prepared from other salts, including other pharmaceutically acceptable salts, of the compounds of Formula (I), (Ia) and (Ib), using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of Formula I may readily be isolated in association with solvent molecules by crystallization or evaporation of an appropriate solvent to give the corresponding solvates.

VI. Pharmaceutical Compositions

In a third aspect, the invention provides pharmaceutical compositions of compounds of Formula (I), (Ia) and (Ib). The pharmaceutical compositions of the present invention encompass any compositions made by admixing a compound of the present invention and a pharmaceutically acceptable carrier. Such compositions are suitable for pharmaceutical use in an animal or human. The pharmaceutical compositions of the present invention comprise a therapeutically effective amount of one or more compounds of Formula (I), (Ia), (Ib), or a pharmaceutically acceptable salt thereof, and a pharmaceutically acceptable carrier. A pharmaceutical composition may optionally contain other active ingredients.

The term "carrier" refers to a vehicle, excipient, diluent, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for, parenteral including subcutaneous, intramuscular, and intravenous, pulmonary, nasal, rectal, topical or oral administration. Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy. The preferred compositions include compositions suitable for oral, parenteral, topical, subcutaneous, or pulmonary, in the form of nasal or buccal inhalation, administration. The compositions may be prepared by any of the methods well-known in the art of pharmacy. The pharmaceutical compositions may be in the form of tablets, pills, capsules, solutions, suspensions, emulsion, powders, suppository and as sustained release formulations. If desired, tablets may be coated by standard aqueous or non-aqueous techniques. In certain embodiments such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that a therapeutically effective dosage will be obtained. The active compounds can also be administered intranasally as, for example, liquid drops or spray. The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the gastrointestinal tract, the composition may be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula (I), (Ia), (Ib) or a salt thereof, and the powder of a suitable carrier and/or lubricant. The compositions for pulmonary administration can be inhaled from any suitable dry powder inhaler device known to a person skilled in the art. Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I), (Ia) or (Ib) per dosage unit for daily administration. In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation. When used in combination with one or more other active ingredients, the compound of the present invention and the other active ingredients may be used in lower doses than when each is used singly. With respect to formulations with respect to any variety of routes of administration, methods and formulations for the administration of drugs are disclosed in *Remington's Pharmaceutical Sciences, 17$^{th}$ Edition*, Gennaro et al. Eds., Mack Publishing Co., 1985, and *Remington's Pharmaceutical Sciences,* Gennaro A R ed. 20$^{th}$ *edition,* 2000, Williams & Wilkins PA, USA, and *Remington: The Science and Practice of Pharmacy, 21$^{st}$ Edition*, Lippincott Williams & Wilkins Eds., 2005; and in *Ansel's Pharmaceutical Dosage Forms and Drug Delivery*

Systems, 8th Edition. Lippincott Williams & Wilkins Eds., 2005, which are herein incorporated as reference.

VII. Definitions

All technical and scientific terms used herein have the same meaning as commonly understood by a person of ordinary skill in the art, unless otherwise defined. The following terms, used in the specification and claims of this application, have the meaning specified hereunder, unless otherwise defined.

The term "alkyl", as used herein, indicates a saturated aliphatic hydrocarbon radical, including straight chain and branched chain radicals of 1 to 6 carbon atoms referred to as $C_{1-6}$ alkyl. Non-limiting examples of alkyl are methyl, ethyl, propyl, isopropyl, n-butyl, iso-butyl, tert-butyl, n-amyl, iso-amyl, n-hexyl, and the like.

The term "carbocyclic compounds or carbocyclic ring" means cyclic compounds in which all of the ring members are carbon atoms.

The terms "heterocyclic" or "heterocyclic ring", as used herein mean cyclic compounds having as ring members atoms of at least two different elements. Typically, the cyclic compounds are a 4- to 7-membered, saturated or partially unsaturated carbocyclic ring wherein one or more carbon atoms are independently replaced by nitrogen. The heteroatom nitrogen optionally may be oxidized, and the nitrogen atom(s) are optionally quaternized.

Examples of heterocyclyl groups include, unsaturated or saturated radicals for instance derived from pyrrolidine, dihydropyrrole, piperidine, pyrazoline, piperazine, pyridine and the like.

Any of the above mentioned alkyl, cycloalkyl, heterocyclyl or heterocyclic ring group may be unsubstituted or substituted by one or more substituents, especially by any of a $C_1$-$C_6$ alkyl.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like. The term MeO means methoxy, the term EtO means ethoxy.

The term "halogen", as used herein, indicates fluorine (F), chlorine (Cl), bromine (Br) or iodine (I).

The term "hydroxy" means a —OH radical.

The term "trifluoromethyl" means a —$CF_3$ radical.

The term "trifluoromethoxy" means a —$OCF_3$ radical.

The term "alkylalkoxy" means an alkyl group functionalized with one or more alkoxy group, like $CH_2$—O—$CH_3$.

VIII. Methods for Preparing Compounds of Formula (I), (Ia) and (Ib)

Compounds of Formula (I), (Ia) and (Ib), provided herein that inhibit the activity of topo II, may be synthesized using synthetic techniques described herein. The reactions can be employed in a linear sequence to provide the compounds described herein or they may be used to synthesize fragments which are subsequently joined by the methods described herein and/or known in the art.

In an aspect, a method for the manufacture of compounds (Ia) and (Ib) is provided according to the following reaction scheme 1.

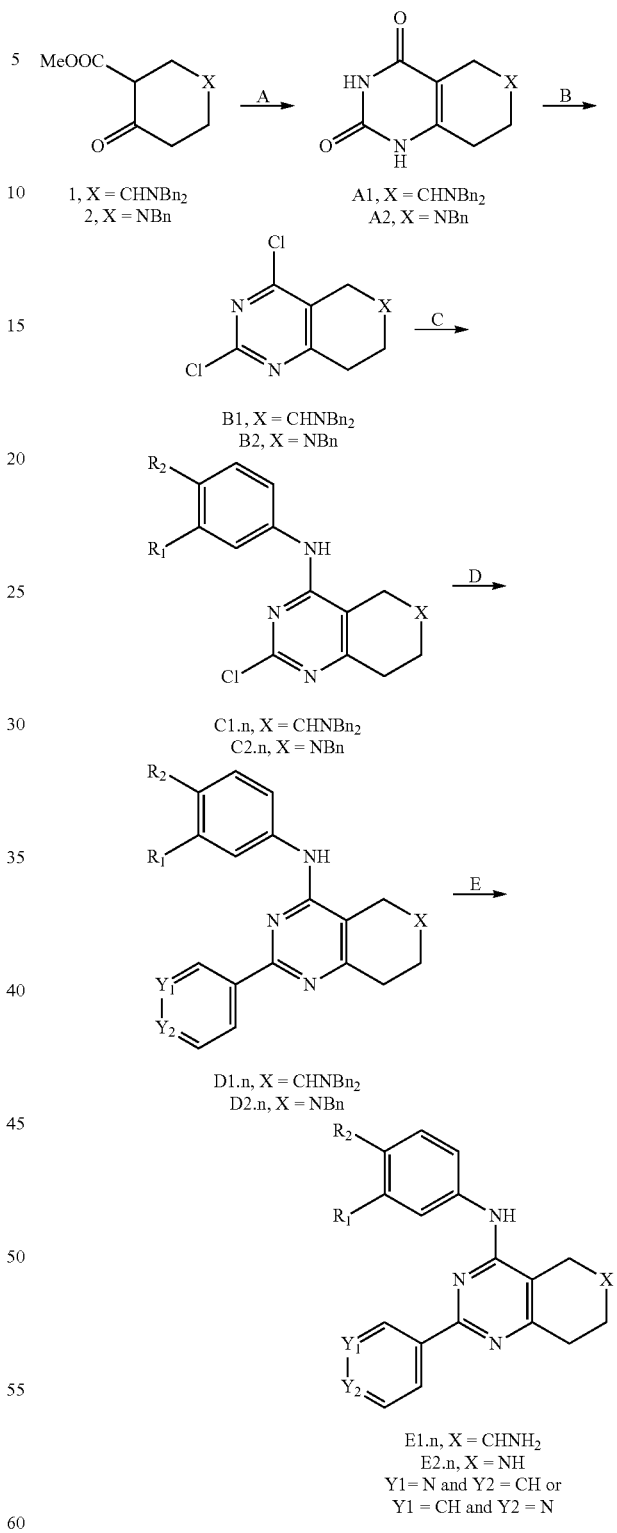

Scheme 1 wherein step A comprises the addition of urea, MeONa in a $C_1$-$C_4$ alcohol step B comprises the addition of $POCl_3$ to give a solution which is evaporated to give a residue step C comprises the addition of aniline and diisopropylethylamine in a C1-C4 alcohol step D comprises the addition of boronic acid PdCl$_2$(dppf) dichloromethane complex and an aqueous solution of K$_2$CO$_3$ in 1,4-dioxane step E comprises the addition of ammonium formate, Pd(OH)$_2$—C, a C$_1$-C$_4$ alcohol.

In accordance with another aspect, a method for the manufacture of a compound E3 according to the invention is provided, in accordance with the following reaction scheme:

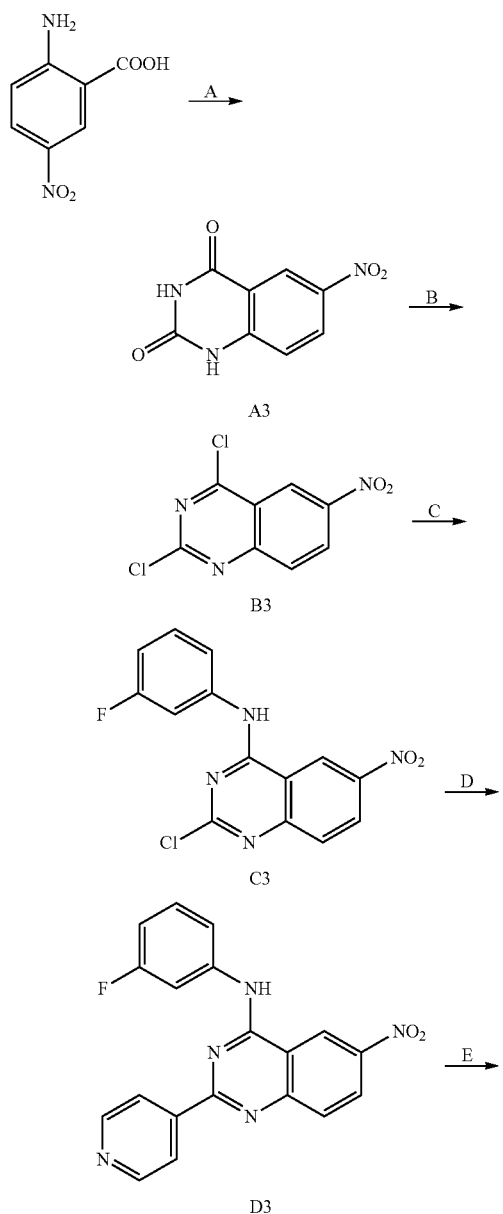

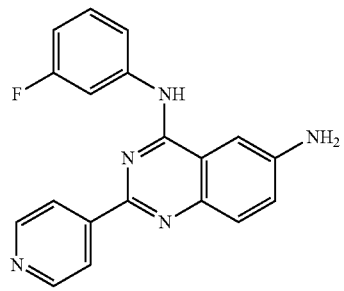

wherein
step A comprises the addition of urea
step B comprises the addition of PCl$_5$ in POCl$_3$
step C comprises the addition of 3-fluoroaniline, diisopropylethylamine
step D comprises the addition of PdCl$_2$(dppf) dichloromethane complex and aqueous K$_2$CO$_3$ solution
step E comprises the addition of ammonium formate (4 mmol), Pd(OH)$_2$—C.

In accordance with another aspect, the compounds of Formula (I) according to claim 1 are prepared with the method defined in claim 20.

With the aim of better illustrating the present invention, without limiting it, the examples reported in Table 1 are provided herein.

TABLE 1

| Examples of Markush formula | |
|---|---|
| Example | Structure |
| E1.1 | 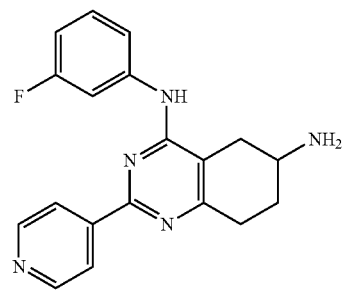 [SMILES: NC1CCc2nc(-c3ccncc3)nc(Nc3cccc(F)c3)c2C1] |
| E1.2 | 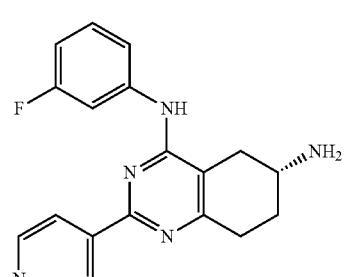 |

TABLE 1-continued

Examples of Markush formula

| Example | Structure |
|---|---|
| E1.3 | 4-(3-fluorophenylamino)-2-(pyridin-4-yl)-5,6,7,8-tetrahydroquinazolin-6-amine |
| E1.4 | 4-(3-methylphenylamino)-2-(pyridin-4-yl)-5,6,7,8-tetrahydroquinazolin-6-amine |
| E1.5 | 4-(3-methoxyphenylamino)-2-(pyridin-4-yl)-5,6,7,8-tetrahydroquinazolin-6-amine |
| E1.6 | 4-(3-aminophenylamino)-2-(pyridin-4-yl)-5,6,7,8-tetrahydroquinazolin-6-amine |
| E1.7 | 4-(3-methylaminophenylamino)-2-(pyridin-4-yl)-5,6,7,8-tetrahydroquinazolin-6-amine |
| E1.8 | 4-(4-fluorophenylamino)-2-(pyridin-4-yl)-5,6,7,8-tetrahydroquinazolin-6-amine |
| E1.9 | 4-(4-hydroxyphenylamino)-2-(pyridin-4-yl)-5,6,7,8-tetrahydroquinazolin-6-amine |
| E1.10 | 4-(3-fluorophenylamino)-2-(pyridin-3-yl)-5,6,7,8-tetrahydroquinazolin-6-amine |
| E1.11 | 4-(4-dimethylaminophenylamino)-2-(pyridin-4-yl)-5,6,7,8-tetrahydroquinazolin-6-amine |
| E2.1 | N-(3-fluorophenyl)-2-(pyridin-4-yl)-5,6,7,8-tetrahydropyrido[3,4-d]pyrimidin-4-amine |

TABLE 1-continued

Examples of Markush formula

| Example | Structure |
|---|---|
| E2.2 | (structure) |
| E2.3 | (structure) |
| E2.4 | (structure) |
| E2.5 | (structure) |
| E2.6 | (structure) |
| E2.7 | (structure) |
| E3 | (structure) |
| E4 | (structure) |
| E5 | (structure) |
| E6 | (structure) |

Working examples of the present invention are hereinafter provided for illustrative and non-limiting purposes, together with examples showing the inhibitory activity (Table 2) of the compounds of the invention.

EXAMPLES

Methods of preparations of compounds of formula I, Ia, Ib

General Considerations.

All the commercial available reagents and solvents were used as purchased from vendors without further purification. Dry solvents were purchased from Sigma-Aldrich. Automated column chromatography purifications were done using a Teledyne ISCO apparatus (CombiFlash® Rf) with pre-packed silica gel columns of different sizes (from 4 g up to 120 g) and mixtures of increasing polarity of cyclohexane and ethyl acetate (EtOAc), cyclohexane and tert-ButylMethyl eter (TBME) or dicloromethane (DCM) and methanol (MeOH). NMR experiments were run on a Bruker Avance III 400 system (400.13 MHz for 1H, and 100.62 MHz for 13C), equipped with a BBI probe and Z-gradients. Spectra were acquired at 300 K, using deuterated dimethylsulfoxide (DMSO-$d_6$), deuterated chloroform (CDCl$_3$), deuterated acetone (Acetone-$d_6$) or deuterated methanol (CD$_3$OD) as solvents. For $^1$H-NMR, data are reported as follows: chemical shift, multiplicity (s=singlet, d=doublet, dd=double of doublets, t=triplet, q=quartet, m=multiplet), coupling constants (Hz) and integration. UPLC/MS analyses were run on a Waters ACQUITY UPLC/MS system consisting of a SQD (single quadrupole detector) mass spectrometer equipped with an electrospray ionization interface and a photodiode array detector. The PDA range was 210-400 nm. Analyses were performed on an ACQUITY UPLC BEH C18 column (100×2.1 mmID, particle size 1.7 μm) with a VanGuard BEH C18 pre-column (5×2.1 mmID, particle size 1.7 μm). Mobile phase was 10 mM NH$_4$OAc in H2O at pH 5 adjusted with CH$_3$COOH (A) and 10 mM NH$_4$OAc in CH$_3$CN—H2O (95:5) at pH 5.0. Electrospray ionization in positive and negative mode was applied. ESI was applied in positive and negative mode. All tested compounds showed ≥90% purity by NMR and UPLC/MS analysis.

Scheme 1

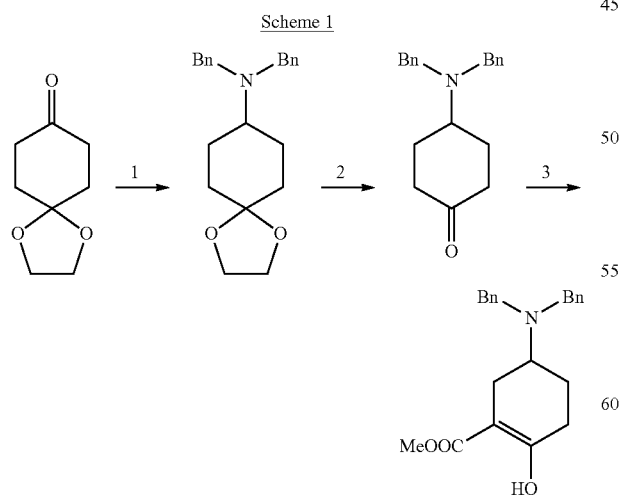

1. NBn$_2$ (1 eq), NaBH(OAc)$_3$ (1.5 eq), 1,2-dichloroethane, room temp., 16 h, yield 77%
2. HCl 2M (2 eq), THF, N$_2$, reflux, 4 h, yield 95%. 3. Dimethyl carbonate (3.3 eq), KH (3.2 eq), NaH (0.7 eq), THF (dry), N$_2$, room temp. to reflux, 3 h, yield 98%.

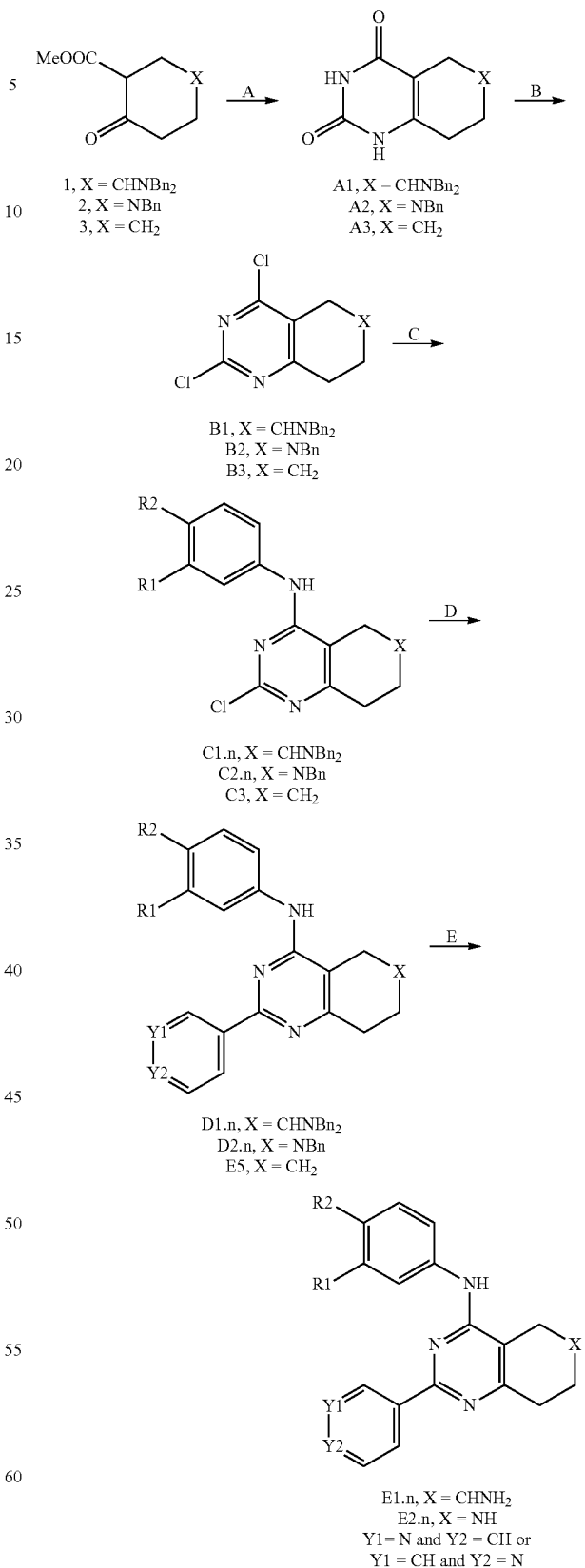

-continued

A. Urea, MeONa, EtOH, N₂, reflux, 16 h. B. POCl₃, N₂, reflux, 5 h. C. Aniline, DIPEA, iPrOH, N₂, microwave, 100° C., 5-16 h or Pd(OAc)₂, rac-BINAP, aniline, Cs₂CO₃, microwave, 80° C., 1,4-dioxane. D. Boronic acid, PdCl₂(dppf)·DCM, K₂CO₃, 1,4-dioxane, Ar, microwave, 100° C., 2 h. E. HCOONH₄, Pd(OH)₂—C, MeOH, Ar, reflux, 4 h.

-continued

A. Urea (10 eq), microwave, 160° C., 4 h, yield 99%. B. POCl₃ (15 eq), PCl₅ (5 eq), reflux, 2 h, yield 58%. C. 3-fluoroaniline (1.1 eq), DIPEA (1.6 eq), iPrOH/DCM (4/1), room temp., 2 h, yield 99%. D. PdCl₂(dppf)·DCM (0.05 eq), K₂CO₃ (2 eq), dioxane, 120° C., 2 h, yield 43%. E. HCOONH₄ (4 eq), Pd(OH)₂—C, MeOH, reflux, 2 h, yield 75%.

Reaction 1 Scheme 1. Synthesis of N,N-dibenzyl-1,4-dioxaspiro[4.5]decan-8-amine

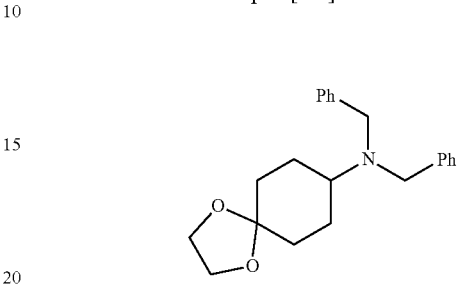

Scheme 2.

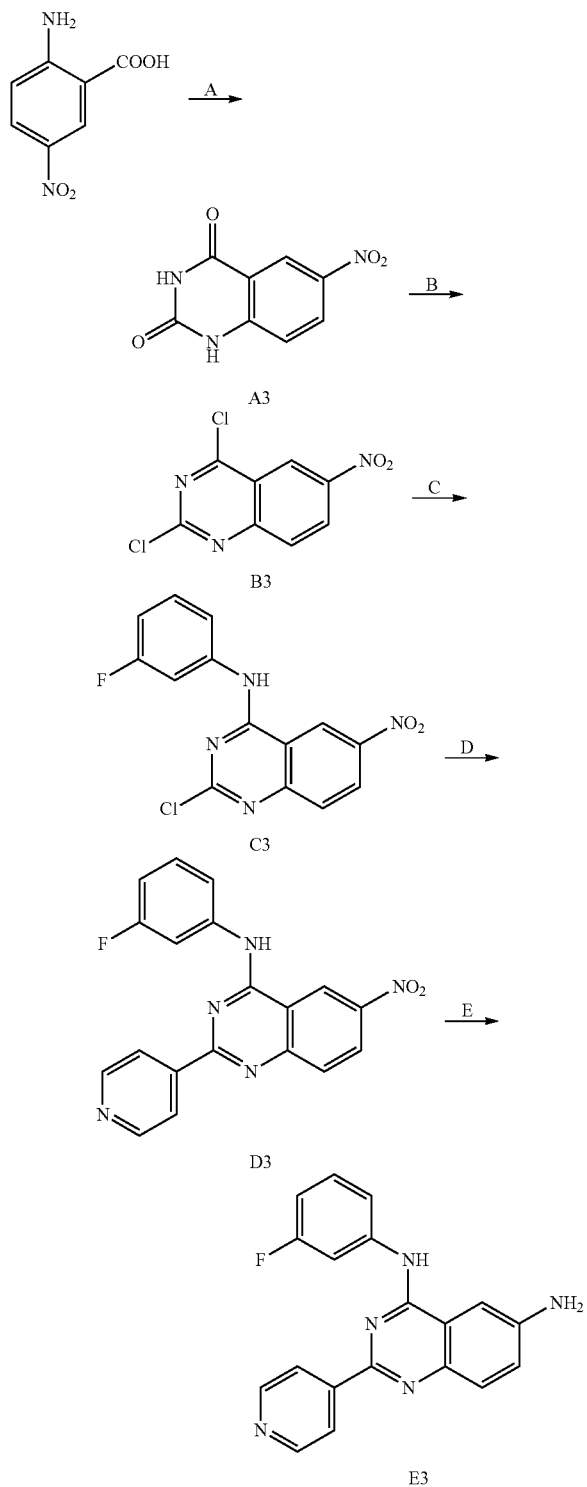

A solution of 1,4-cyclohexanedione monoethylene acetal (5000 mg, 31.05 mmol) in dry 1,2-dichloroethane (129 ml), dibenzylamine (6.3 ml, 31.05 mmol) and acetic acid (1.8 ml, 31.05 mmol) was stirred for 15 minutes at room temperature. Then sodium triacetoxyborohydride (10391.9 mg, 46.58 mmol) was portionwise added and the reaction mixture stirred at room temperature for 16 hours, afterwards was diluted with DCM (100 ml), extracted with NaHCO₃ 10% solution (100 ml), the aqueous layer extracted twice with DCM (2×100 ml), combined organic layers were dried over Na₂SO₄ and concentrated to dryness at low pressure. Purification by typical silica gel flash chromatography (cyclohexane/TBME from 100:0 to 90:10) afforded the pure title compound (8070 mg, yield 77%) as a white solid. Rt=2.15 min; MS (ESI) m/z: 338.3 [M-H]⁺, [M-H]⁺ calculated: 338.5. ¹H NMR (400 MHz, CDCl₃) δ 7.39-7.33 (m, 4H), 7.28 (dd, J=8.5, 7.0 Hz, 4H), 7.24-7.16 (m, 2H), 3.96-3.87 (m, 4H), 3.64 (s, 4H), 2.57 (tt, J=11.5, 3.6 Hz, 1H), 1.90-1.81 (m, 2H), 1.81-1.72 (m, 2H), 1.67 (td, J=12.5, 3.5 Hz, 2H), 1.45 (td, J=13.0, 4.3 Hz, 2H).

Reaction 2 Scheme 1. Synthesis of 4-(dibenzylamino)cyclohexanone

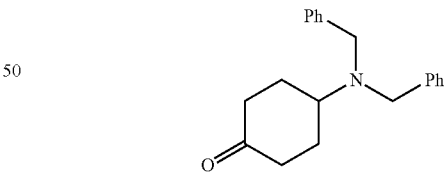

HCl 2M solution (62 ml, 124.70 mmol) was added to a of N,N-dibenzyl-1,4-dioxaspiro[4.5]decan-8-amine (8070 mg, 23.19 mmol) solution in tetrahydrofuran (62 ml). The reaction mixture was stirred under N₂ atmosphere at reflux temperature for 4 hours, then cooled in an ice/water bath, basified with NaOH 5M solution, extracted with AcOEt (3×50 ml), combined organic layers dried over Na₂SO₄ and concentrated to dryness at low pressure. Purification by typical silica gel flash chromatography (cyclohexane/TBME from 100:0 to 90:10) afforded the pure title compound (6464 mg, yield 95%). Rt=1.83 min; MS (ESI) m/z: 294.2 [M-H]⁺, [M-H]⁺ calculated: 294.2. ¹H NMR (400 MHz, CDCl₃) δ

7.40-7.35 (m, 4H), 7.34-7.28 (m, 4H), 7.26-7.20 (m, 2H), 3.66 (s, 4H), 3.02 (tt, J=11.5, 3.4 Hz, 1H), 2.43 (p, J=2.4 Hz, 1H), 2.39 (p, J=2.4 Hz, 1H), 2.31-2.22 (m, 2H), 2.20-2.14 (m, 2H), 1.88-1.78 (m, 2H).

Reaction 3 Scheme 1. Synthesis of methyl 5-(dibenzylamino)-2-hydroxy-cyclohexene-1-carboxylate (Compound 1)

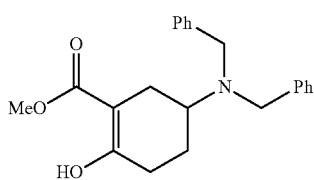 [SMILES: COC(=O)C1=C(O)CCC(N(Cc2ccccc2)Cc2ccccc2)C1]

Under $N_2$ atmosphere, a solution of 4-(dibenzylamino)cyclohexanone (6200 mg, 20.50 mmol) in HO tetrahydrofuran (2.5 ml) was dropwise added to a suspension of KH (5261.3 mg, 65.59 mmol) and NaH (414.2 mg, 16.40 mmol) in dry tetrahydrofuran (256 ml) at room temperature. The reaction mixture was stirred for 30 minutes and dimethyl carbonate was added (5.9 ml, 69.08 mmol), then stirred at reflux temperature under for 3 hours, cooled to room temperature, added to cold $NaHCO_3$ saturated solution (100 ml), the organic layer separated, the aqueous one extracted with ethyl acetate (100 ml), the combined organic layers dried over $Na_2SO_4$ and concentrated to dryness at low pressure. Purification by typical silica gel flash chromatography (cyclohexane/TBME from 100:0 to 90:10) afforded the pure title compound (7058 mg, yield 98%). Rt=2.54 min; MS (ESI) m/z: 352.2 [M-H]$^+$, [M-H]$^+$ calculated: 352.2. $^1$H NMR (400 MHz, $CDCl_3$) δ 12.06 (s, 1H), 7.42-7.34 (m, 4H), 7.29 (dd, J=8.3, 6.7 Hz, 4H), 7.24-7.18 (m, 2H), 3.76 (s, 3H), 3.72 (d, J=14.0 Hz, 2H), 3.62 (d, J=14.0 Hz, 2H), 2.88-2.73 (m, 1H), 2.54-2.43 (m, 1H), 2.43-2.18 (m, 3H), 2.05-1.94 (m, 1H), 1.74-1.57 (m, 1H).

General Procedure Reaction A Scheme 1. Pyrimidone Fused Ring Formation

A suspension of corresponding cyclic 2-oxo ethylester (1 mmol) in ethanol (4.5 ml), urea (5 mmol) and sodium methoxide (4.5 mmol) was stirred at reflux temperature for 16 hours. Afterwards the reaction crude was concentrated to dryness at low pressure, resulting solid triturated in water (0.5 ml), ice cooled, pH adjusted to 8-9 with concentrated HCl and filtrated. Resulting solid was then rinsed with methanol (0.5 ml) and diethyl ether (0.5 ml) yielding titled compound.

General Procedure Reaction B Scheme 1. Pyrimidone Fused Ring Clorination

A suspension of corresponding pyrimidone fused ring obtained from general method A (1 mmol) in $POCl_3$ (1.5 ml) was stirred at 120° C. under $N_2$ atmosphere until total solution was observed (around 4 hours). $POCl_3$ was then evaporated at low pressure, resulting residue solved in dichloromethane (3 ml), poured onto ice cold $NaHCO_3$ saturated solution (18 ml), aqueous pH adjusted to 7-8 with $NaHCO_3$ (no gas evolution observed after addition), organic layer separated, dried over $Na_2SO_4$ and concentrated to dryness at low pressure. Resulting solid normal phase chromatography purification finally yielded titled compound.

General Procedure Reaction C Scheme 1. Aniline Introduction

Method 1. Aromatic Nucleophilic Substitution.

A suspension of dichlorinated pyrimidinic fused ring obtained from general method B (1 mmol), corresponding aniline (1.1 mmol) and diisopropylethylamine (5 mmol) in 2-propanol (2 ml) was stirred in a CEM® microwave apparatus at 100-160° C. (depending of corresponding aniline) until reaction completion or no crude evolution was observed. Then reaction crude was concentrated to dryness at low pressure, solved in dichloromethane (20 ml), extracted with $NaHCO_3$ saturated solution (20 ml), dried over $Na_2SO_4$ and concentrated to dryness at low pressure. Final normal phase purification yielded titled compound.

Method 2. Palladium Catalyzed Coupling.

A mixture of $Pd(OAc)_2$ (0.05 mmol) and rac-BINAP (0.05 mmol) in 1,4-dioxane (3 ml) was stirred under Ar flushing for 10 minutes. Then were stepwise added a solution of corresponding dichlorinated pyrimidinic fused ring obtained from general method B (1 mmol) in 1,4-dioxane (1 ml), a solution of corresponding aniline (1 mmol) in 1,4-dioxane (1 ml) and $Cs_2CO_3$ (1.2 mmol). The reaction mixture was stirred in a CEM® microwave apparatus at 80° C. for 4 hours, filtrated through a celite coarse patch, rinsed with DCM and concentrated to dryness at low pressure. Final normal phase purification yielded titled compound.

General Procedure Reaction D Scheme 1. Suzuki Coupling Reaction

A suspension of compound obtained from general method C (1 mmol), corresponding boronic acid (1.2 mmol), $PdCl_2$(dppf) dichloromethane complex (0.1 mmol) and $K_2CO_3$ 2 M solution (2 mmol) in 1,4-dioxane (10 ml) was stirred in a CEM® microwave apparatus at 120° C. for 2 hours. Resulting crude was portioned between dichloromethane (25 ml), $NaHCO_3$ saturated solution (25 ml), the organic layer dried over $Na_2SO_4$ and concentrated to dryness at low pressure. Final normal phase purification yielded titled compound.

General Procedure Reaction E Scheme 1. Benzyl Group Removal

Under $N_2$ atmosphere, a suspension of compound to be deprotected (1 mmol), ammonium formate (4 mmol), $Pd(OH)_2$/C (20% of starting material weight) was stirred at reflux temperature until reaction completion. Catalyst was filtered off with trough a celite coarse patch and resulting filtrate concentrated to dryness at low pressure. Final normal phase purification yielded titled compound.

Example E1.1. N4-(3-fluorophenyl)-2-(4-pyridyl)-5,6,7,8-tetrahydroquinazoline-4,6-diamine

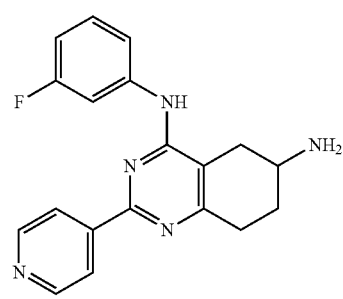

Step 1. Synthesis of 6-(dibenzylamino)-5,6,7,8-tetrahydro-1H-quinazoline-2,4-dione (Compound A1)

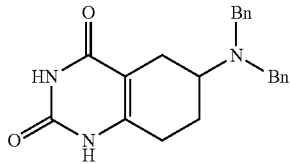 [SMILES: O=c1[nH]c2c(c(=O)[nH]1)CC(N(Cc1ccccc1)Cc1ccccc1)CC2]

Titled compound was obtained using compound 1 (7040.0 mg, 20.03 mmol) following the general procedure A previously described and affording pure title compound (5865 mg, yield 81%). Rt=0.94 min (gradient 1); MS (ESI) m/z: 362.1 [M-H]$^+$, [M-H]$^+$ calculated: 362.4. $^1$H NMR (400 MHz, DMSO-d$_6$) δ 10.85 (br s, 1H), 10.56 (br s, 1H), 7.36 (d, J=7.2 Hz, 4H), 7.30 (t, J=7.2 Hz, 4H), 7.20 (t, J=7.2 Hz, 2H), 3.67 (d, J=14.2 Hz, 2H), 3.59 (d, J=14.2 Hz, 2H), 2.76-2.61 (m, 1H), 2.48-2.37 (m, 2H), 2.37-2.22 (m, 1H), 2.25-2.11 (m, 1H), 2.06-1.93 (m, 1H), 1.64 (qd, J=12.1, 5.6 Hz, 1H).

Step 2. Synthesis of N,N-dibenzyl-2,4-dichloro-5,6,7,8-tetrahydroquinazolin-6 amine (Compound B1)

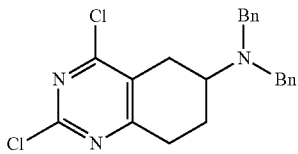 [SMILES: Clc1nc(Cl)c2c(n1)CCC(N(Cc1ccccc1)Cc1ccccc1)C2]

Titled compound was obtained using compound A1 (5862 mg, 16.22 mmol) following the general procedure B previously described and affording pure title compound (5685 mg, yield 88%). Rt=2.60 min (gradient 2); MS (ESI) m/z: 398.2/400.2 [M-H]$^+$, [M-H]$^+$ calculated: 398.2/400.2. $^1$H NMR (400 MHz, CDCl$_3$) δ 7.41 (d, J=7.4 Hz, 4H), 7.32 (t, J=7.4 Hz, 4H), 7.23 (d, J=7.4 Hz, 2H), 3.82 (d, J=13.7 Hz, 2H), 3.69 (d, J=13.7 Hz, 2H), 3.19-3.00 (m, 1H), 3.02-2.86 (m, 1H), 2.87-2.65 (m, 2H), 2.42-2.12 (m, 1H), 2.01-1.56 (m, 2H).

Step 3. Synthesis of N6,N6-dibenzyl-2-chloro-N4-(3-fluorophenyl)-5,6,7,8-tetrahydroquina zoline-4,6-diamine (Compound C1.1)

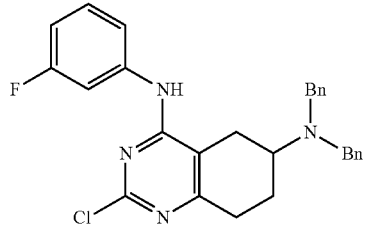 [SMILES: Fc1cccc(Nc2nc(Cl)nc3c2CC(N(Cc2ccccc2)Cc2ccccc2)CC3)c1]

Titled compound was obtained using compound B1 (400 mg, 1.0 mmol) and 3-Fluoroaniline (0.12 ml, 1.21 mmol) following the general procedure C method 1 previously described at 100° C. for 72 h. Final normal phase purification (cyclohexane/TBME from 100:0 to 80:20) afforded pure title compound (152 mg, yield 32%). Rt=2.61 min (gradient 2); MS (ESI) m/z: 471.1/473.1 [M-H]$^+$, [M-H]$^+$ calculated: 471.2/473.2. $^1$H NMR (400 MHz, CDCl$_3$) δ 7.56 (dt, J=11.0, 2.3 Hz, 1H), 7.45-7.38 (m, 4H), 7.37-7.28 (m, 5H), 7.30-7.19 (m, 3H), 6.82 (tdd, J=8.2, 2.5, 1.2 Hz, 1H), 6.38 (s, 1H), 3.86 (d, J=14.1 Hz, 2H), 3.67 (d, J=14.0 Hz, 2H), 3.17-3.05 (m, 1H), 2.95 (ddd, J=18.2, 5.0, 2.4 Hz, 1H), 2.71 (ddd, J=18.1, 12.1, 5.6 Hz, 1H), 2.55-2.46 (m, 2H), 2.32-2.21 (m, 1H), 1.78 (qd, J=12.3, 5.1 Hz, 1H).

Step 4. N6,N6-dibenzyl-N4-(3-fluorophenyl)-2-(4-pyridyl)-5,6,7,8-tetrahydro quinazoline-4,6-diamine (Compound D1.1)

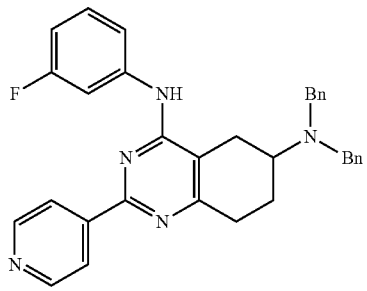 [SMILES: Fc1cccc(Nc2nc(-c3ccncc3)nc3c2CC(N(Cc2ccccc2)Cc2ccccc2)CC3)c1]

Titled compound was obtained using compound C1.1 (150 mg, 0.32 mmol) and Pyridine-4-boronic acid (52 mg, 0.38 mmol) following the general procedure D previously described. Final normal phase purification (cyclohexane/TBME from 80:20 to 50.20) afforded pure title compound (157 mg, yield 96%). Rt=2.74 min (gradient 2); MS (ESI) m/z: 516.4 [M-H]$^+$, [M-H]$^+$ calculated: 516.2. $^1$H NMR (400 MHz, DMSO-d$_6$). 1H NMR (400 MHz, DMSO-d$_6$) δ 8.72 (s, 1H), 8.70-8.67 (m, 2H), 8.10-8.05 (m, 2H), 7.73 (dt, J=12.0, 2.3 Hz, 1H), 7.63 (ddd, J=8.2, 2.0, 0.9 Hz, 1H), 7.48-7.39 (m, 5H), 7.32 (dd, J=8.3, 6.9 Hz, 4H), 7.25-7.17 (m, 2H), 6.92 (tdd, J=8.4, 2.5, 0.9 Hz, 1H), 3.80 (d, J=14.2 Hz, 2H), 3.70 (d, J=14.2 Hz, 2H), 3.05-2.84 (m, 3H), 2.84-2.63 (m, 2H), 2.16 (d, J=12.3 Hz, 1H), 1.85 (tt, J=12.0, 6.2 Hz, 1H).

Step 5. N4-(3-fluorophenyl)-2-(4-pyridyl)-5,6,7,8-tetrahydroquinazoline-4,6-diamine (Compound E1.1)

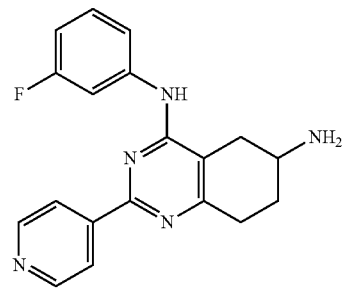

Titled compound was obtained using compound D1.1 (154.3 mg, 0.29 mmol) following the general procedure E previously described for 4 hours. Final normal phase purification (DCM/DCM:NH₃ 1M MeOH 4:1 from 90:10 to 60:40) afforded pure title compound (62.9 mg, yield 64%). Rt=1.53 min (gradient 1); MS (ESI) m/z: 336.2 [M-H]⁺, [M-H]⁺ calculated: 336.2. ¹H NMR (400 MHz, DMSO-d₆) δ 8.73 (s, 1H), 8.72-8.67 (m, 2H), 8.16-8.05 (m, 2H), 7.75 (dt, J=12.1, 2.3 Hz, 1H), 7.64 (dd, J=8.0, 1.9 Hz, 1H), 7.41 (td, J=8.2, 6.9 Hz, 1H), 6.90 (td, J=8.4, 2.6 Hz, 1H), 3.27 (s, 3H), 2.89 (dddd, J=19.8, 15.1, 8.6, 5.4 Hz, 3H), 2.46-2.35 (m, 1H), 2.09-1.89 (m, 1H), 1.70 (dtd, J=12.6, 9.5, 5.9 Hz, 1H).

Examples E1.2 and E1.3. Chiral Chromatographic Separation of (6R)—N4-(3-fluorophenyl)-2-(4-pyridyl)-5,6,7,8-tetrahydroquinazoline-4,6-diamine (E1.2) and (6S)—N4-(3-fluorophenyl)-2-(4-pyridyl)-5,6,7,8-tetrahydroquinazoline-4,6-diamine (E1.3)

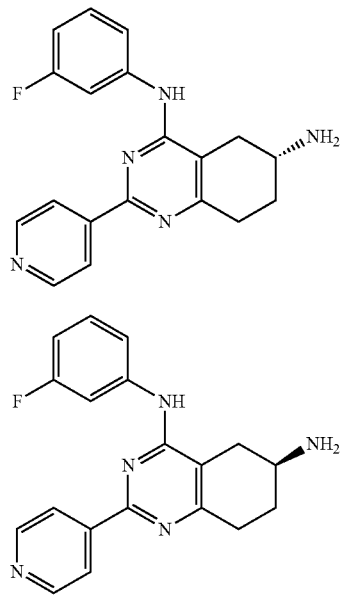

E1.2

E1.3

Chiral semi-preparative separation of both enantiomers by HPLC was run on a Waters Alliance HPLC instrument consisting of an e2695 Separation Module and a 2998 Photodiode Array Detector. The PDA range was 210-400 nm. The separation was performed isocratic on a ChiralCel OD-H column (250×10 mm ID, particle size: 5 μm) using 0.1% TEA Heptane-EtOH (95:5) as mobile phase at 5 ml/min. Post-analysis of each isolated enantiomer was performed on a ChiralCel OD-H column (250×4.6 mm ID, particle size: 5 μm) using 0.1% TEA Heptane-EtOH (95:5) as mobile phase at 1 ml/min. Chiral structure of enantiomers E1.2 and E1.3 was arbitrary assigned.

(6R)—N4-(3-fluorophenyl)-2-(4-pyridyl)-5,6,7,8-tetrahydroquinazoline-4,6-diamine (E1.2)

Enantiomeric purity of 95.2% ee at 290 nm of the first eluting enantiomer at Rt=63.3 min in ChiralCel OD-H column. Rt=1.53 min in ACQUITY UPLC BEH C18 column (gradient 1); MS (ESI) m/z: 336.2 [M-H]⁺, [M-H]⁺ calculated: 336.2. ¹H NMR (400 MHz, DMSO-d₆) δ 8.73 (s, 1H), 8.72-8.67 (m, 2H), 8.16-8.05 (m, 2H), 7.75 (dt, J=12.1, 2.3 Hz, 1H), 7.64 (dd, J=8.0, 1.9 Hz, 1H), 7.41 (td, J=8.2, 6.9 Hz, 1H), 6.90 (td, J=8.4, 2.6 Hz, 1H), 3.27 (s, 3H), 2.89 (dddd, J=19.8, 15.1, 8.6, 5.4 Hz, 3H), 2.46-2.35 (m, 1H), 2.09-1.89 (m, 1H), 1.70 (dtd, J=12.6, 9.5, 5.9 Hz, 1H).

(6S)—N4-(3-fluorophenyl)-2-(4-pyridyl)-5,6,7,8-tetrahydroquinazoline-4,6-diamine (E1.3)

enantiomeric purity >99.5% ee at 290 nm of the second eluting enantiomer at Rt=67.6 min in ChiralCel OD-H column. Rt=1.53 min in ACQUITY UPLC BEH C18 column (gradient 1); MS (ESI) m/z: 336.2 [M-H]⁺, [M-H]⁺ calculated: 336.2. ¹H NMR (400 MHz, DMSO-d₆) δ 8.73 (s, 1H), 8.72-8.67 (m, 2H), 8.16-8.05 (m, 2H), 7.75 (dt, J=12.1, 2.3 Hz, 1H), 7.64 (dd, J=8.0, 1.9 Hz, 1H), 7.41 (td, J=8.2, 6.9 Hz, 1H), 6.90 (td, J=8.4, 2.6 Hz, 1H), 3.27 (s, 3H), 2.89 (dddd, J=19.8, 15.1, 8.6, 5.4 Hz, 3H), 2.46-2.35 (m, 1H), 2.09-1.89 (m, 1H), 1.70 (dtd, J=12.6, 9.5, 5.9 Hz, 1H).

Example E1.4

(N4-(m-tolyl)-2-(4-pyridyl)-5,6,7,8-tetrahydroquinazoline-4,6-diamine

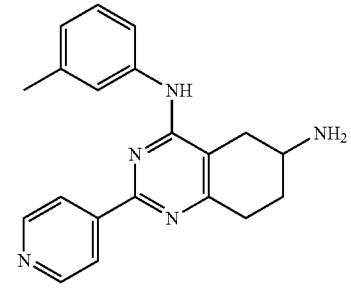

Step 1. Synthesis of N6,N6-dibenzyl-2-chloro-N4-(m-tolyl)-5,6,7,8-tetrahydroquinazoline-4,6-diamine (Compound C1.4)

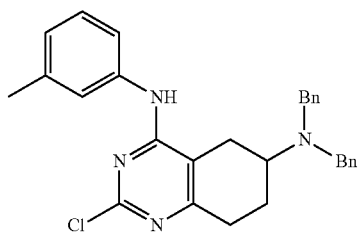 [SMILES: Cc1cccc(Nc2nc(Cl)nc3c2CC(N(Cc2ccccc2)Cc2ccccc2)CC3)c1]

Titled compound was obtained using compound B1 (250 mg, 0.63 mmol) and m-Toluidine (0.08 ml, 0.69 mmol) following the general procedure C method 1 previously described at 100° C. for 16 h. Final normal phase purification (cyclohexane/TBME from 100:0 to 90:10) afforded pure title compound (176 mg, yield 60%). Rt=2.57 min (gradient 2); MS (ESI) m/z: 469.3 [M-H]⁺, [M-H]⁺ calculated: 469.2. ¹H NMR (400 MHz, CDCl₃) δ 7.50-7.37 (m, 6H), 7.37-7.28 (m, 2H), 7.28-7.21 (m, 5H), 6.95 (d, J=7.5 Hz, 1H), 6.35 (s, 1H), 3.86 (d, J=14.0 Hz, 2H), 3.67 (d, J=14.0 Hz, 2H), 3.11 (q, J=9.0 Hz, 1H), 2.92 (ddd, J=18.3, 5.1, 2.2 Hz, 1H), 2.69 (ddd, J=18.1, 12.2, 5.5 Hz, 1H), 2.52 (d, J=8.5 Hz, 2H), 2.38 (s, 3H), 2.31-2.18 (m, 1H), 1.84-1.69 (m, 1H).

Step 2. N6,N6-dibenzyl-N4-(m-tolyl)-2-(4-pyridyl)-5,6,7,8-tetrahydroquinazoline-4,6-diamine (Compound D1.4)

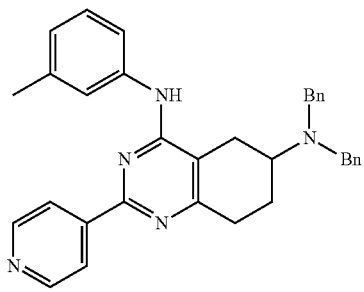 [SMILES: Cc1cccc(Nc2nc(-c3ccncc3)nc3c2CC(N(Cc2ccccc2)Cc2ccccc2)CC3)c1]

Titled compound was obtained using compound C1.4 (170 mg, 0.36 mmol) and Pyridine-4-boronic acid (59.4 mg, 0.43 mmol) following the general procedure D previously described. Final normal phase purification (cyclohexane/AcOEt from 90:10 to 60:40) afforded pure title compound (135 mg, yield 73%). Rt=2.84 min (gradient 2); MS (ESI) m/z: 512.1 [M-H]+, [M-H]+ calculated: 512.3. $^1$H NMR (400 MHz, DMSO-$d_6$) δ 8.72 (s, 1H), 8.70-8.67 (m, 2H), 8.10-8.05 (m, 2H), 7.73 (dt, J=12.0, 2.3 Hz, 1H), 7.63 (ddd, J=8.2, 2.0, 0.9 Hz, 1H), 7.48-7.39 (m, 5H), 7.32 (dd, J=8.3, 6.9 Hz, 4H), 7.25-7.17 (m, 2H), 6.92 (tdd, J=8.4, 2.5, 0.9 Hz, 1H), 3.80 (d, J=14.2 Hz, 2H), 3.70 (d, J=14.2 Hz, 2H), 3.05-2.84 (m, 3H), 2.84-2.63 (m, 2H), 2.16 (d, J=12.3 Hz, 1H), 1.85 (tt, J=12.0, 6.2 Hz, 1H).

Step 3. N4-(m-tolyl)-2-(4-pyridyl)-5,6,7,8-tetrahydroquinazoline-4,6-diamine (Compound E1.4)

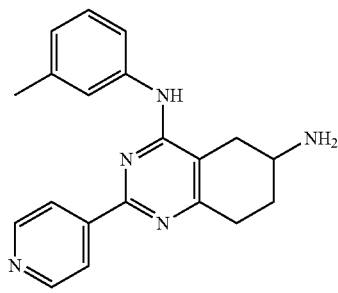 [SMILES: Cc1cccc(Nc2nc(-c3ccncc3)nc3c2CC(N)CC3)c1]

Titled compound was obtained using compound D1.1 (170.0 mg, 0.36 mmol) following the general procedure E previously described for 4 hours. Final normal phase purification (neutral alumina, DCM/DCM:MeOH 4:1 from 90:10 to 70:30) afforded pure title compound (56.4 mg, yield 67%). Rt=1.55 min (gradient 1); MS (ESI) m/z: 332.2 [M-H]+, [M-H]+ calculated: 332.2. $^1$H NMR (400 MHz, DMSO-$d_6$) δ 8.74-8.65 (m, 2H), 8.45 (s, 1H), 8.21-8.05 (m, 2H), 7.72-7.55 (m, 2H), 7.26 (t, J=7.8 Hz, 1H), 6.90 (d, J=7.4 Hz, 1H), 3.23-3.10 (m, 1H), 2.93-2.70 (m, 3H), 2.35 (s, 3H), 2.33-2.24 (m, 1H), 2.03-1.87 (m, 1H), 1.72-1.55 (m, 1H).

Example E1.5. N4-(3-methoxyphenyl)-2-(4-pyridyl)-5,6,7,8-tetrahydroquinazoline-4,6-diamine

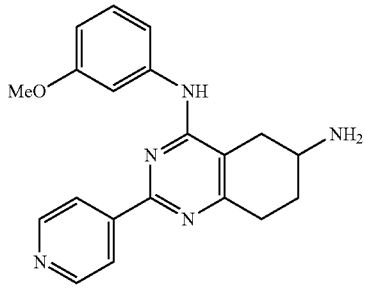 [SMILES: COc1cccc(Nc2nc(-c3ccncc3)nc3c2CC(N)CC3)c1]

Step 1. Synthesis of N6,N6-dibenzyl-2-chloro-N4-(3-methoxyphenyl)-5,6,7,8-tetrahydroquinazoline-4,6-diamine (Compound C1.5)

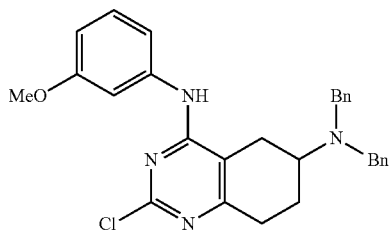 [SMILES: COc1cccc(Nc2nc(Cl)nc3c2CC(N(Cc2ccccc2)Cc2ccccc2)CC3)c1]

Titled compound was obtained using compound B1 (250 mg, 0.63 mmol) and 3-methoxyaniline (0.08 ml, 0.69 mmol) following the general procedure C method 1 previously described at 100° C. for 16 h. Final normal phase purification (cyclohexane/TBME from 100:0 to 90:10) afforded pure title compound (140 mg, yield 46%). Rt=2.43 min (gradient 2); MS (ESI) m/z: 485.2 [M-H]+, [M-H]+ calculated: 469.2. $^1$H NMR (400 MHz, CDCl$_3$) δ 7.48-7.38 (m, 5H), 7.33 (t, J=7.4 Hz, 5H), 7.24 (dd, J=7.8, 2.5 Hz, 3H), 6.95 (d, J=7.5 Hz, 1H), 6.35 (s, 1H), 3.86 (d, J=14.1 Hz, 2H), 3.67 (d, J=14.0 Hz, 2H), 3.11 (q, J=9.0 Hz, 1H), 2.92 (ddd, J=18.3, 5.1, 2.2 Hz, 1H), 2.69 (ddd, J=18.1, 12.2, 5.5 Hz, 1H), 2.52 (d, J=8.5 Hz, 2H), 2.38 (s, 3H), 2.30-2.19 (m, 1H), 1.85-1.70 (m, 1H).

Step 2. Synthesis of N6,N6-dibenzyl-N4-(3-methoxyphenyl)-2-(4-pyridyl)-5,6,7,8-tetrahydroquinazoline-4,6-diamine (Compound D1.5)

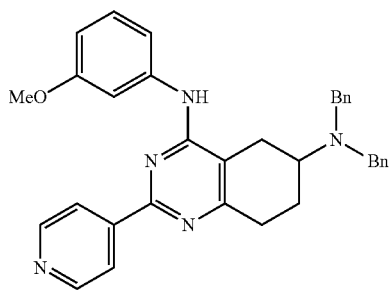 [SMILES: COc1cccc(Nc2nc(-c3ccncc3)nc3c2CC(N(Cc2ccccc2)Cc2ccccc2)CC3)c1]

Titled compound was obtained using compound C1.4 (135 mg, 0.28 mmol) and Pyridine-4-boronic acid (45.6 mg, 0.33 mmol) following the general procedure D previously described. Final normal phase purification (cyclohexane/ AcOEt from 75:25 to 60:40) afforded pure title compound (132 mg, yield 90%). Rt=2.62 min (gradient 2); MS (ESI) m/z: 528.4 [M-H]$^+$, [M-H]$^+$ calculated: 528.3. $^1$H NMR (400 MHz, DMSO-d$_6$) δ 8.71-8.63 (m, 2H), 8.55 (s, 1H), 8.15-8.05 (m, 2H), 7.48-7.40 (m, 5H), 7.38 (ddd, J=8.1, 2.0, 1.0 Hz, 1H), 7.31 (q, J=7.7 Hz, 5H), 7.25-7.18 (m, 2H), 6.69 (ddd, J=8.1, 2.5, 1.0 Hz, 1H), 3.82-3.78 (m, 5H), 3.70 (d, J=14.2 Hz, 2H), 3.03-2.84 (m, 3H), 2.84-2.63 (m, 2H), 2.16 (d, J=12.2 Hz, 1H), 1.84 (qd, J=12.1, 5.1 Hz, 1H).

Step 3. Synthesis of N4-(3-methoxyphenyl)-2-(4-pyridyl)-5,6,7,8-tetrahydroquinazoline-4,6-diamine (Compound E1.5)

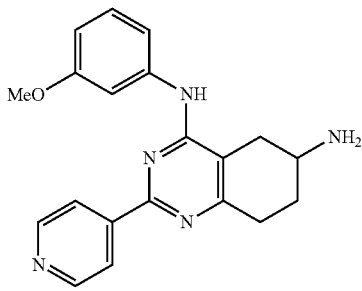

Titled compound was obtained using compound D1.5 (130.0 mg, 0.25 mmol) following the general procedure E previously described for 4 hours. Final normal phase purification (neutral alumina, DCM/DCM:MeOH 4:1 from 90:10 to 60:40) afforded pure title compound (51.4 mg, yield 60%). Rt=1.45 min (gradient 1); MS (ESI) m/z: 348.2 [M-H]$^+$, [M-H]$^+$ calculated: 348.2. $^1$H NMR (400 MHz, DMSO-d$_6$) δ 8.80-8.63 (m, 2H), 8.48 (s, 1H), 8.30-8.02 (m, 2H), 7.50 (t, J=2.2 Hz, 1H), 7.43 (ddd, J=8.2, 2.0, 0.9 Hz, 1H), 7.27 (t, J=8.1 Hz, 1H), 6.65 (ddd, J=8.2, 2.5, 0.9 Hz, 1H), 3.78 (s, 3H), 3.17 (qd, J=5.5, 2.2 Hz, 1H), 2.95-2.70 (m, 3H), 2.40-2.25 (m, 1H), 2.01-1.88 (m, 1H), 1.63 (dtd, J=12.3, 9.4, 5.5 Hz, 1H).

Example E1.6. N4-(3-aminophenyl)-2-(4-pyridyl)-5,6,7,8-tetrahydroquinazoline-4,6-diamine

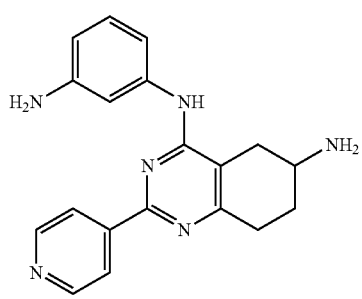 [SMILES: Nc1cccc(Nc2nc(-c3ccncc3)nc3c2CC(N)CC3)c1]

Step 1. Synthesis of N4-(3-aminophenyl)-N6,N6-dibenzyl-2-chloro-5,6,7,8-tetrahydroquinazoline-4,6-diamine (Compound C1.6)

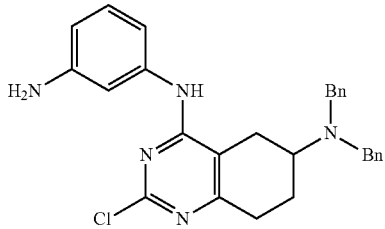 [SMILES: Nc1cccc(Nc2nc(Cl)nc3c2CC(N(Cc2ccccc2)Cc2ccccc2)CC3)c1]

Titled compound was obtained using compound B1 (500 mg, 1.26 mmol) and N-Boc-m-phenylenediamine (290.5 mg, 1.38 mmol) following the general procedure C method 1 previously described at 120° C. for 16 h. The reaction crude was concentrated to dryness at low pressure, portioned between DCM (25 ml) and NaOH 0.1 M solution (25 ml), then the organic layer was dried over Na$_2$SO$_4$ and concentrated to dryness at low pressure. Resulting crude was solved in 1,4-dioxane (3.1 ml), a solution of HCl (4M) in 1,4-dioxane (3.1 ml) was dropwise added and the reaction mixture stirred at room temperature for 1 h, then the reaction crude was concentrated to dryness at low pressure, the resulting crude portioned between DCM (20 ml) and NaOH 0.1 M (20 ml), the organic layer dried over Na$_2$SO$_4$ and concentrated to dryness at low pressure. Final normal phase purification (cyclohexane/AcOEt from 85:15 to 65:35) afforded pure title compound (101 mg, yield 17%). Rt=1.93 min (gradient 2); MS (ESI) m/z: 470.2 [M-H]$^+$, [M-H]$^+$ calculated: 470.2. $^1$H NMR (400 MHz, DMSO-d$_6$) δ 8.52 (s, 1H), 7.41 (d, J=7.2 Hz, 4H), 7.31 (dd, J=8.2, 6.8 Hz, 4H), 7.26-7.16 (m, 2H), 7.05-6.90 (m, 1H), 6.73 (dt, J=4.6, 1.5 Hz, 2H), 6.35 (ddd, J=8.0, 1.9, 1.0 Hz, 1H), 5.08 (s, 2H), 3.75 (d, J=14.2 Hz, 2H), 3.66 (d, J=14.1 Hz, 2H), 2.98-2.53 (m, 2H), 2.07 (d, J=12.5 Hz, 1H), 1.75 (dq, J=12.6, 7.3 Hz, 1H).

Step 2. Synthesis of N4-(3-aminophenyl)-N6,N6-dibenzyl-2-(4-pyridyl)-5,6,7,8-tetrahydroquinazoline-4,6-diamine (Compound D1.6)

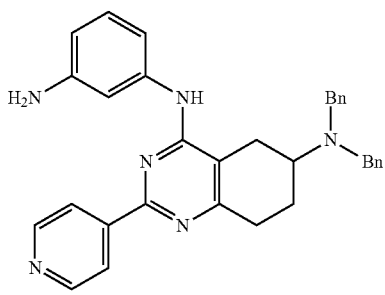 [SMILES: Nc1cccc(Nc2nc(-c3ccncc3)nc3c2CC(N(Cc2ccccc2)Cc2ccccc2)CC3)c1]

Titled compound was obtained using compound C1.6 (94 mg, 0.206 mmol) and Pyridine-4-boronic acid (32.8 mg, 0.24 mmol) following the general procedure D previously described. Final normal phase purification (cyclohexane/ AcOEt from 70:30 to 40:60) afforded pure title compound (80 mg, yield 78%). Rt=2.04 min (gradient 2); MS (ESI) m/z: 513.4 [M-H]$^+$, [M-H]$^+$ calculated: 513.3. $^1$H NMR (400

MHz, CDCl₃) δ 8.68 (d, J=5.2 Hz, 2H), 8.18 (d, J=5.2 Hz, 2H), 7.46 (d, J=7.6 Hz, 4H), 7.33 (t, J=7.4 Hz, 4H), 7.26 (s, 9H), 7.03 (d, J=7.9 Hz, 1H), 6.57-6.24 (m, 2H), 3.93 (d, J=14.0 Hz, 2H), 3.73 (d, J=14.0 Hz, 2H), 3.31-3.10 (m, 1H), 3.03 (d, J=17.4 Hz, 1H), 2.89-2.55 (m, 1H), 2.48-2.13 (m, 1H), 1.85 (ddd, J=17.2, 12.2, 5.9 Hz, 1H), 1.78-1.57 (m, 2H).

Step 3. Synthesis of N4-(3-aminophenyl)-2-(4-pyridyl)-5,6,7,8-tetrahydroquinazoline-4,6-diamine (Compound E1.6)

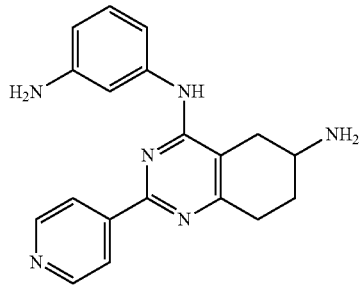 [SMILES: Nc1cccc(Nc2nc(-c3ccncc3)nc3c2CC(N)CC3)c1]

Titled compound was obtained using compound D1.5 (76.0 mg, 0.15 mmol) following the general procedure E previously described for 4 hours. Final normal phase purification (DCM/DCM:NH₃ 1N MeOH 4:1 from 80:20 to 60:40) afforded pure title compound (30.0 mg, yield 31%). Rt=1.25 min (gradient 1); MS (ESI) m/z: 333.2 [M-H]⁺, [M-H]⁺ calculated: 333.2. ¹H NMR (400 MHz, DMSO-d₆): δ 8.73-8.63 (m, 2H), 8.20 (s, 1H), 8.16-8.09 (m, 2H), 7.05 (t, J=2.1 Hz, 1H), 7.00 (t, J=7.9 Hz, 1H), 6.92 (ddd, J=8.0, 2.0, 1.1 Hz, 1H), 6.31 (ddd, J=7.9, 2.2, 1.0 Hz, 1H), 5.06 (s, 2H), 3.16 (d, J=7.0 Hz, 1H), 2.97-2.69 (m, 3H), 2.35-2.15 (m, 1H), 2.07-1.83 (m, 1H), 1.71-1.51 (m, 1H).

Example E1.7. N4-[3-(methylamino)phenyl]-2-(4-pyridyl)-5,6,7,8-tetrahydroquinazoline-4,6-diamine

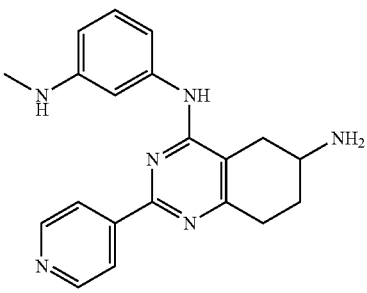 [SMILES: CNc1cccc(Nc2nc(-c3ccncc3)nc3c2CC(N)CC3)c1]

Step 1. Synthesis of N6,N6-dibenzyl-2-chloro-N4-[3-(methylamino)phenyl]-5,6,7,8-tetrahydroquinazoline-4,6-diamine (Compound C1.7)

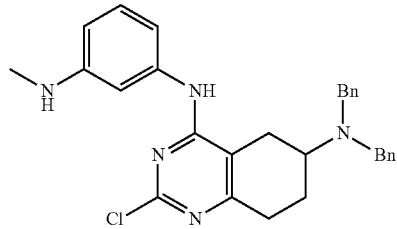 [SMILES: CNc1cccc(Nc2nc(Cl)nc3c2CC(N(Cc2ccccc2)Cc2ccccc2)CC3)c1]

Titled compound was obtained using compound B1 (250 mg, 0.63 mmol) and 3-(N-tert-Butoxycarbonyl-N-methylamino)aniline (161.5 mg, 0.69 mmol) following the general procedure C method 1 previously described at 100° C. for 16 h. The reaction crude was concentrated to dryness at low pressure, portioned between DCM (25 ml) and NaOH 0.1 M solution (25 ml), then the organic layer was dried over Na₂SO₄ and concentrated to dryness at low pressure. Resulting crude was solved in 1,4-dioxane (1.4 ml), a solution of HCl (4M) in 1,4-dioxane (1.4 ml) was dropwise added and the reaction mixture stirred at room temperature for 3 h, then the reaction crude was concentrated to dryness at low pressure, the resulting crude portioned between DCM (20 ml) and NaOH 0.1 M (20 ml), the organic layer dried over Na₂SO₄ and concentrated to dryness at low pressure. Final normal phase purification (cyclohexane/AcOEt from 100:0 to 80:20) afforded pure title compound (112 mg, yield 41%). Rt=2.24 min (gradient 2); MS (ESI) m/z: 484.3 [M-H]⁺, [M-H]⁺ calculated: 484.2. ¹H NMR (400 MHz, DMSO-d₆) δ 8.56 (s, 1H), 7.51-7.35 (m, 4H), 7.31 (t, J=7.5 Hz, 4H), 7.26-7.16 (m, 2H), 7.05 (t, J=7.9 Hz, 1H), 6.83-6.72 (m, 2H), 6.44-6.27 (m, 1H), 5.65 (q, J=5.0 Hz, 1H), 3.76 (d, J=14.2 Hz, 2H), 3.66 (d, J=14.2 Hz, 2H), 2.95-2.53 (m, 7H), 2.15-2.02 (m, 2H), 1.76 (qd, J=12.2, 5.3 Hz, 1H).

Step 2. Synthesis of N6,N6-dibenzyl-N4-[3-(methylamino)phenyl]-2-(4-pyridyl)-5,6,7,8-tetrahydroquinazoline-4,6-diamine (Compound D1.7)

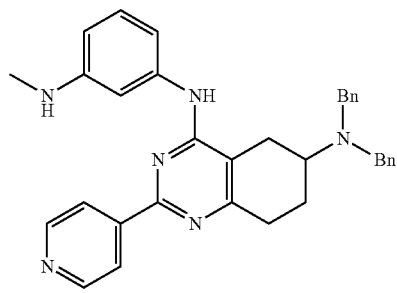 [SMILES: CNc1cccc(Nc2nc(-c3ccncc3)nc3c2CC(N(Cc2ccccc2)Cc2ccccc2)CC3)c1]

Titled compound was obtained using compound C1.7 (110 mg, 0.23 mmol) and Pyridine-4-boronic acid (37.2 mg, 0.27 mmol) following the general procedure D previously described. Final normal phase purification (cyclohexane/AcOEt from 70:30 to 50:50) afforded pure title compound (105 mg, yield 88%). Rt=2.40 min (gradient 2); MS (ESI) m/z: 527.4 [M-H]⁺, [M-H]⁺ calculated: 527.7. ¹H NMR (400 MHz, DMSO-d₆) δ 8.75-8.61 (m, 2H), 8.37 (s, 1H), 8.15-

8.06 (m, 2H), 7.49-7.39 (m, 4H), 7.32 (t, J=7.6 Hz, 4H), 7.26-7.17 (m, 2H), 7.09 (t, J=8.0 Hz, 1H), 7.04 (t, J=2.1 Hz, 1H), 6.98-6.91 (m, 1H), 6.32 (ddd, J=8.2, 2.3, 0.9 Hz, 1H), 5.68 (q, J=5.0 Hz, 1H), 3.80 (d, J=14.2 Hz, 2H), 3.70 (d, J=14.2 Hz, 2H), 2.90 (dd, J=21.2, 15.1 Hz, 3H), 2.72 (d, J=5.0 Hz, 3H), 2.15 (d, J=12.3 Hz, 1H), 1.83 (qd, J=12.1, 5.0 Hz, 1H).

Step 3. Synthesis of N4-[3-(methylamino)phenyl]-2-(4-pyridyl)-5,6,7,8-tetrahydroquinazoline-4,6-diamine (Compound E1.7)

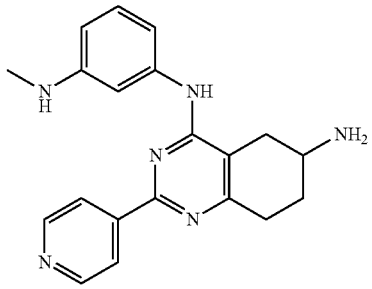 [SMILES: CNc1cccc(Nc2nc(-c3ccncc3)nc3c2CC(N)CC3)c1]

Titled compound was obtained using compound D1.7 (100 mg, 0.19 mmol) following the general procedure E previously described for 4 hours. Final normal phase purification (DCM/DCM:NH$_3$ 1N MeOH 4:1 from 95:5 to 75:25) afforded pure title compound (48.0 mg, yield 73%). Rt=1.39 min (gradient 1); MS (ESI) m/z: 347.2 [M-H]$^+$, [M-H]$^+$ calculated: 347.2. $^1$H NMR (400 MHz, DMSO-d$_6$) δ 8.71-8.63 (m, 2H), 8.25 (s, 1H), 8.18-8.10 (m, 2H), 7.12-7.03 (m, 2H), 7.02-6.96 (m, 1H), 6.29 (ddd, J=8.0, 2.3, 1.0 Hz, 1H), 5.65 (q, J=5.0 Hz, 1H), 3.16 (tdd, J=8.3, 4.9, 2.8 Hz, 1H), 2.94-2.72 (m, 3H), 2.71 (d, J=5.0 Hz, 3H), 2.30 (dd, J=16.9, 8.1 Hz, 1H), 1.93 (d, J=12.7 Hz, 1H), 1.72 (s, 2H), 1.62 (dtd, J=12.7, 9.6, 5.7 Hz, 1H).

Example E1.8. N4-(4-fluorophenyl)-2-(4-pyridyl)-5,6,7,8-tetrahydroquinazoline-4,6-diamine

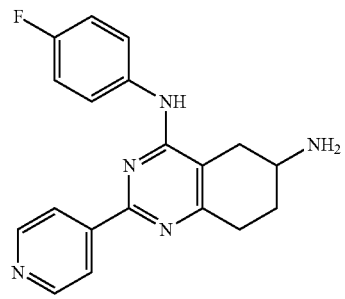 [SMILES: NC1CCc2nc(-c3ccncc3)nc(Nc3ccc(F)cc3)c2C1]

Step 1. Synthesis of N6,N6-dibenzyl-2-chloro-N4-(4-fluorophenyl)-5,6,7,8-tetrahydroquinazoline-4,6-diamine (Compound C1.8)

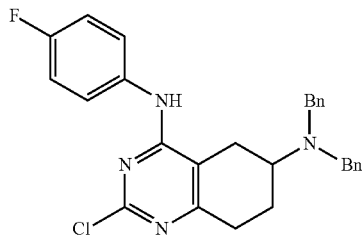 [SMILES: Fc1ccc(Nc2nc(Cl)nc3c2CC(N(Cc2ccccc2)Cc2ccccc2)CC3)cc1]

Titled compound was obtained using compound B1 (300 mg, 0.75 mmol) and 4-Fluoroaniline (0.07 ml, 0.75 mmol) following the general procedure C method 1 previously described at 100° C. for 16 h. Final normal phase purification (cyclohexane/TBME from 100:0 to 90:10) afforded pure title compound (303 mg, yield 73%). Rt=2.70 min (gradient 2); MS (ESI) m/z: 473.1 [M-H]$^+$, [M-H]$^+$ calculated: 473.2. $^1$H NMR (400 MHz, CDCl$_3$) δ 7.70-7.58 (m, 3H), 7.45-7.38 (m, 4H), 7.37-7.28 (m, 6H), 7.12-7.02 (m, 2H), 3.67 (d, J=14.0 Hz, 2H), 3.17-3.05 (m, 1H), 2.95 (ddd, J=18.2, 5.0, 2.4 Hz, 1H), 2.71 (ddd, J=18.1, 12.1, 5.6 Hz, 1H), 2.55-2.46 (m, 2H), 2.32-2.21 (m, 1H), 1.78 (qd, J=12.3, 5.1 Hz, 1H).

Step 2. Synthesis of N6,N6-dibenzyl-N4-(4-fluorophenyl)-2-(4-pyridyl)-5,6,7,8-tetrahydroquinazoline-4,6-diamine (Compound D1.8)

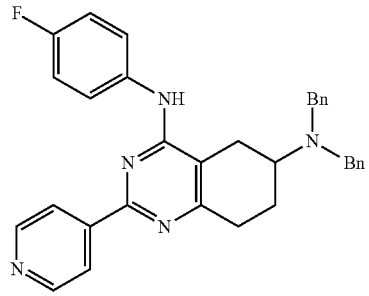 [SMILES: Fc1ccc(Nc2nc(-c3ccncc3)nc3c2CC(N(Cc2ccccc2)Cc2ccccc2)CC3)cc1]

Titled compound was obtained using compound C1.8 (75 mg, 0.16 mmol) and Pyridine-4-boronic acid (26.0 mg, 0.19 mmol) following the general procedure D previously described. Final normal phase purification (cyclohexane/TBME from 80:20 to 50:50) afforded pure title compound (75.7 mg, yield 92%). Rt=2.97 min (gradient 2); MS (ESI) m/z: 516.4 [M-H]$^+$, [M-H]$^+$ calculated: 516.2. $^1$H NMR (400 MHz, CDCl$_3$): δ 8.74-8.62 (m, 2H), 8.21-8.05 (m, 2H), 7.69-7.55 (m, 2H), 7.50-7.39 (m, 4H), 7.38-7.29 (m, 4H), 7.26 (s, 1H), 7.16-7.05 (m, 2H), 6.41 (s, 1H), 3.91 (d, J=14.0 Hz, 2H), 3.71 (d, J=14.0 Hz, 2H), 3.29-3.10 (m, 1H), 3.11-2.98 (m, 1H), 2.79 (ddd, J=17.9, 12.3, 5.5 Hz, 1H), 2.65 (d, J=8.1 Hz, 2H), 2.43-2.22 (m, 1H), 1.95-1.81 (m, 1H).

Step 3. Synthesis of N4-(4-fluorophenyl)-2-(4-pyridyl)-5,6,7,8-tetrahydroquinazoline-4,6-diamine (Compound E1.8)

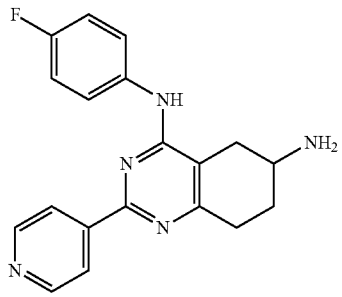 [SMILES: NC1CCc2nc(-c3ccncc3)nc(Nc3ccc(F)cc3)c2C1]

Titled compound was obtained using compound D1.8 (75.7 mg, 0.14 mmol) following the general procedure E previously described for 4 hours. Final normal phase purification (DCM/DCM:NH$_3$ 1N MeOH 4:1 from 95:5 to 75:25) afforded pure title compound (45.3 mg, yield 94%). Rt=1.65 min (gradient 1); MS (ESI) m/z: 336.1 [M-H]$^+$, [M-H]$^+$ calculated: 336.2. $^1$H NMR (400 MHz, DMSO-d$_6$) δ 8.67 (d, J=5.2 Hz, 2H), 8.59 (s, 1H), 8.08 (d, J=5.2 Hz, 2H), 7.76 (ddd, J=9.3, 5.0, 2.3 Hz, 2H), 7.22 (t, J=8.9 Hz, 2H), 2.93-2.71 (m, 3H), 2.31 (dd, J=16.9, 8.1 Hz, 1H), 1.94 (ddt, J=11.1, 7.8, 4.4 Hz, 1H), 1.63 (dtd, J=12.4, 9.6, 5.7 Hz, 1H), 1.23 (t, J=7.2 Hz, 1H).

Example E1.9. 4-[[6-amino-2-(4-pyridyl)-5,6,7,8-tetrahydroquinazolin-4-yl]amino]phenol

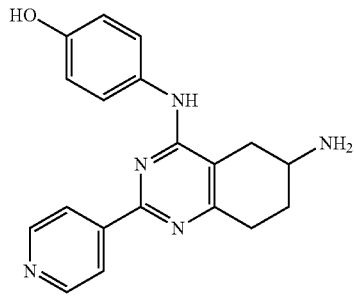

Step 1. Synthesis of 4-[[2-chloro-6-(dibenzylamino)-5,6,7,8-tetrahydroquinazolin-4-yl]amino]phenol (Compound C1.9)

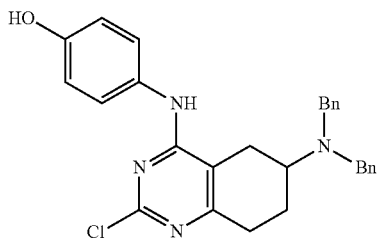 [SMILES: Oc1ccc(Nc2nc(Cl)nc3c2CC(N(Cc2ccccc2)Cc2ccccc2)CC3)cc1]

Titled compound was obtained using compound B1 (250 mg, 0.63 mmol) and p-hydroxyaniline (0.08 ml, 0.69 mmol) following the general procedure C method 1 previously described at 120° C. for 4 h. Final normal phase purification (cyclohexane/AcOEt from 100:0 to 75:25) afforded pure title compound (195 mg, yield 66%). Rt=1.83 min (gradient 2); MS (ESI) m/z: 471.0 [M-H]$^+$, [M-H]$^+$ calculated: 471.2. $^1$H NMR (400 MHz, CDCl$_3$) δ 9.95 (s, 1H), 7.80 (s, 1H), 7.37-7.26 (m, 3H), 7.29-7.24 (m, 6H), 7.24-7.20 (m, 2H), 6.90-6.84 (m, 2H), 4.21 (dt, J=12.5, 1.0 Hz, 2H), 3.69 (dt, J=12.3, 1.0 Hz, 2H), 3.14-2.99 (m, 2H), 2.83 (dt, J=17.9, 6.0 Hz, 1H), 2.69 (tt, J=7.9, 6.8 Hz, 1H), 2.49 (dd, J=18.0, 8.0 Hz, 1H), 2.15 (ddt, J=13.0, 6.9, 6.1 Hz, 1H), 1.75 (ddt, J=13.1, 7.1, 6.2 Hz, 1H).

Step 2. Synthesis of 4-[[6-(dibenzylamino)-2-(4-pyridyl)-5,6,7,8-tetrahydroquinazolin-4-yl]amino]phenol (Compound D1.9)

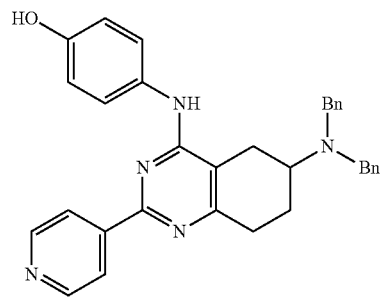 [SMILES: Oc1ccc(Nc2nc(-c3ccncc3)nc3c2CC(N(Cc2ccccc2)Cc2ccccc2)CC3)cc1]

Titled compound was obtained using compound C1.9 (190 mg, 0.40 mmol) and Pyridine-4-boronic acid (66.1 mg, 0.48 mmol) following the general procedure D previously described. Final normal phase purification (cyclohexane/TBME from 45:55 to 30:70) afforded pure title compound (160 mg, yield 77%). Rt=1.95 min (gradient 2); MS (ESI) m/z: 514.4 [M-H]$^+$, [M-H]$^+$ calculated: 514.3. $^1$H NMR (400 MHz, DMSO-d$_6$) δ 9.25 (s, 1H), 8.80-8.52 (m, 2H), 8.44 (s, 1H), 8.16-7.93 (m, 2H), 7.56-7.36 (m, 6H), 7.32 (t, J=7.6 Hz, 4H), 7.25-7.15 (m, 2H), 6.89-6.73 (m, 2H), 3.79 (d, J=14.2 Hz, 2H), 3.69 (d, J=14.2 Hz, 2H), 3.03-2.78 (m, 2H), 2.75-2.62 (m, 2H), 2.15 (d, J=12.1 Hz, 1H), 1.82 (qd, J=12.3, 5.1 Hz, 1H).

Step 3. Synthesis of 4-[[6-amino-2-(4-pyridyl)-5,6,7,8-tetrahydroquinazolin-4-yl]amino]phenol (Compound E1.9)

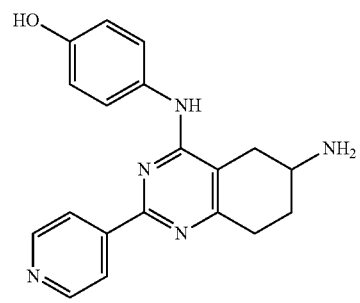

Titled compound was obtained using compound D1.9 (155.0 mg, 0.30 mmol) following the general procedure E previously described for 4 hours. Final normal phase purification (DCM/DCM:NH$_3$ 1N MeOH 4:1 from 75:25 to 50:50) afforded pure title compound (79.8 mg, yield 79%). Rt=0.49 min (gradient 1); MS (ESI) m/z: 334.2 [M-H]$^+$, [M-H]$^+$ calculated: 334.2. $^1$H NMR (400 MHz, DMSO-d$_6$) δ 8.69-8.61 (m, 2H), 8.33 (s, 1H), 8.12-8.01 (m, 2H), 7.52-7.40 (m, 2H), 6.83-6.72 (m, 2H), 3.23-3.08 (m, 1H), 2.81 (dtt, J=15.2, 9.8, 5.6 Hz, 3H), 2.26 (dd, J=16.9, 8.2 Hz, 1H), 2.00-1.86 (m, 1H), 1.61 (dtd, J=12.7, 9.6, 5.7 Hz, 1H).

Example E1.10. N4-(3-fluorophenyl)-2-(3-pyridyl)-5,6,7,8-tetrahydroquinazoline-4,6-diamine

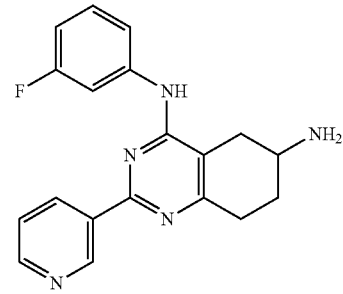 [SMILES: NC1CCc2nc(-c3cccnc3)nc(Nc3cccc(F)c3)c2C1]

Step 1. Synthesis of N6,N6-dibenzyl-N4-(3-fluorophenyl)-2-(3-pyridyl)-5,6,7,8-tetrahydroquinazoline-4,6-diamine (Compound D1.10)

Titled compound was obtained using compound C1.1 (55 mg, 0.12 mmol) and Pyridine-3-boronic acid (19.2 mg, 0.14 mmol) following the general procedure D previously described. Final normal phase purification (cyclohexane/TBME from 80:20 to 50:50) afforded pure title compound (58.0 mg, yield 96%). Rt=3.10 min (gradient 2); MS (ESI) m/z: 516.4 [M-H]$^+$, [M-H]$^+$ calculated: 516.2. $^1$H NMR (400 MHz, CDCl$_3$) δ 9.54 (dd, J=2.2, 0.9 Hz, 1H), 8.65 (dd, J=4.8, 1.7 Hz, 1H), 8.58 (dt, J=7.9, 2.0 Hz, 1H), 7.68 (dt, J=11.2, 2.3 Hz, 1H), 7.46 (d, J=7.8 Hz, 5H), 7.41-7.29 (m, 7H), 7.26 (s, 2H), 6.81 (tdd, J=8.3, 2.6, 1.2 Hz, 1H), 6.49 (s, 1H), 3.91 (d, J=13.7 Hz, 2H), 3.71 (d, J=14.0 Hz, 2H), 3.29-3.10 (m, 1H), 3.11-2.98 (m, 1H), 2.80 (ddd, J=17.9, 12.2, 5.4 Hz, 1H), 2.65 (d, J=8.3 Hz, 2H), 2.46-2.22 (m, 1H), 1.84 (qd, J=12.2, 4.8 Hz, 1H).

Step 2. Synthesis of N4-(3-fluorophenyl)-2-(3-pyridyl)-5,6,7,8-tetrahydroquinazoline-4,6-diamine (Compound E1.10)

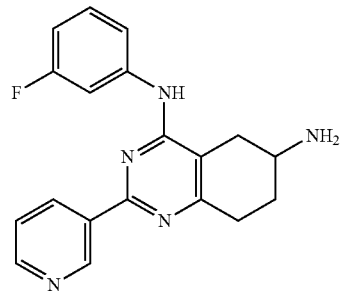 [SMILES: NC1CCc2nc(-c3cccnc3)nc(Nc3cccc(F)c3)c2C1]

Titled compound was obtained using compound D1.10 (58.0 mg, 0.11 mmol) following the general procedure E previously described for 4 hours. Final normal phase purification (DCM/DCM:NH$_3$ 1N MeOH 4:1 from 95:5 to 75:25) afforded pure title compound (12.2 mg, yield 33%). Rt=1.71 min (gradient 1); MS (ESI) m/z: 336.1 [M-H]$^+$, [M-H]$^+$ calculated: 336.2. $^1$H NMR (400 MHz, CD$_3$OD) δ 9.45-9.32 (m, 1H), 8.64 (dt, J=8.0, 1.9 Hz, 1H), 8.58 (dd, J=4.9, 1.7 Hz, 1H), 7.70 (dt, J=11.7, 2.3 Hz, 1H), 7.56-7.44 (m, 2H), 7.35 (td, J=8.2, 6.6 Hz, 1H), 6.83 (tdd, J=8.4, 2.6, 0.9 Hz, 1H), 3.29-3.22 (m, 1H), 3.04-2.83 (m, 3H), 2.40 (dd, J=16.3, 9.1 Hz, 1H), 2.21-2.08 (m, 1H), 1.77 (dtd, J=12.8, 10.3, 6.2 Hz, 1H).

Example E1.11. N4-[4-(dimethylamino)phenyl]-2-(4-pyridyl)-5,6,7,8-tetrahydroquinazoline-4,6-diamine

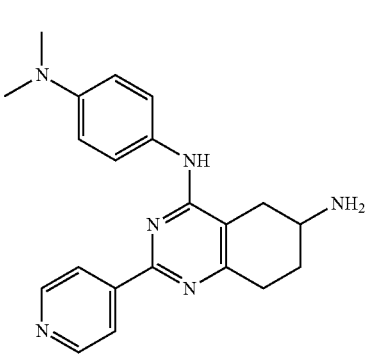 [SMILES: CN(C)c1ccc(Nc2nc(-c3ccncc3)nc3c2CC(N)CC3)cc1]

Step 1. Synthesis of N6,N6-dibenzyl-2-chloro-N4-[4-(dimethylamino)phenyl]-5,6,7,8-tetrahydroquinazoline-4,6-diamine (Compound C1.11)

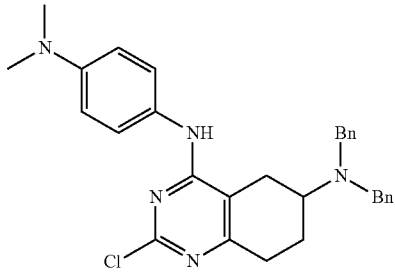 [SMILES: CN(C)c1ccc(Nc2nc(Cl)nc3c2CC(N(Cc2ccccc2)Cc2ccccc2)CC3)cc1]

Titled compound was obtained using compound B1 (250 mg, 0.63 mmol) and N4,N4-dimethylbenzene-1,4-diamine (0.09 ml, 0.69 mmol) following the general procedure C method 1 previously described at 100° C. for 16 h. Final normal phase purification (cyclohexane/AcOEt from 100:0 to 70:30) afforded pure title compound (240 mg, yield 77%). Rt=2.44 min (gradient 2); MS (ESI) m/z: 498.1/499.1 [M-H]$^+$, [M-H]$^+$ calculated: 498.1/498.9. $^1$H NMR (400 MHz, CDCl$_3$) δ 7.42 (d, J=7.5 Hz, 4H), 7.34 (dt, J=14.7, 8.1 Hz, 6H), 7.24 (t, J=7.4 Hz, 2H), 6.72 (s, 2H), 6.28 (s, 1H), 3.84 (d, J=14.1 Hz, 2H), 3.66 (d, J=14.0 Hz, 2H), 3.16-3.01 (m, 1H), 3.01-2.81 (m, 1H), 2.73-2.58 (m, 1H), 2.48 (s, 2H), 2.30-2.16 (m, 1H), 1.74 (qd, J=12.3, 5.1 Hz, 1H), 1.43 (s, 6H).

Step 2. N6,N6-dibenzyl-N4-[4-(dimethylamino)phenyl]-2-(4-pyridyl)-5,6,7,8-tetrahydroquinazoline-4,6-diamine (Compound D1.11)

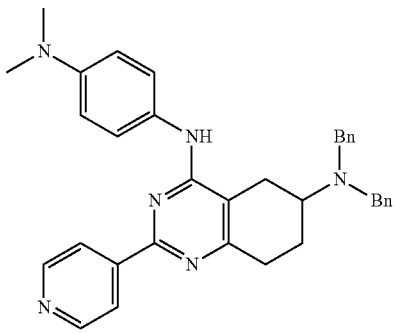 [SMILES: CN(C)c1ccc(Nc2nc(-c3ccncc3)nc3c2CC(N(Cc2ccccc2)Cc2ccccc2)CC3)cc1]

Titled compound was obtained using compound C1.11 (240 mg, 0.48 mmol) and Pyridine-4-boronic acid (85.7 mg, 0.58 mmol) following the general procedure D previously described. Final normal phase purification (cyclohexane/AcOEt from 75:25 to 50:50) afforded pure title compound (197 mg, yield 76%). Rt=2.62 min (gradient 2); MS (ESI) m/z: 541.2 [M-H]$^+$, [M-H]$^+$ calculated: 541.7. $^1$H NMR (400 MHz, DMSO-d$_6$) δ 8.68-8.60 (m, 2H), 8.40 (s, 1H), 8.09-8.01 (m, 2H), 7.57-7.49 (m, 2H), 7.47-7.39 (m, 4H), 7.32 (t, J=7.5 Hz, 4H), 7.25-7.17 (m, 2H), 6.84-6.74 (m, 2H), 3.79 (d, J=14.2 Hz, 2H), 3.69 (d, J=14.2 Hz, 2H), 3.02-2.92 (m, 1H), 2.91 (s, 6H), 2.89-2.78 (m, 2H), 2.76-2.60 (m, 2H), 2.14 (d, J=12.1 Hz, 1H), 1.81 (qd, J=12.3, 5.1 Hz, 1H).

Step 3. N4-[4-(dimethylamino)phenyl]-2-(4-pyridyl)-5,6,7,8-tetrahydroquinazoline-4,6-diamine (Compound E1.11)

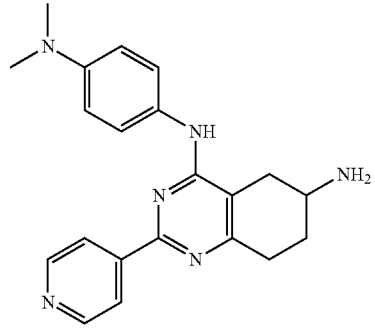 [SMILES: CN(C)c1ccc(Nc2nc(-c3ccncc3)nc3c2CC(N)CC3)cc1]

Titled compound was obtained using compound D1.11 (197.2 mg, 0.48 mmol) following the general procedure E previously described for 5 hours. Final normal phase purification (DCM/DCM:NH$_3$ 1M MeOH 4:1 from 95:5 to 40:60) afforded pure title compound (79.4 mg, yield 46%). Rt=1.32 min (gradient 1); MS (ESI) m/z: 361.2 [M-H]$^+$, [M-H]$^+$ calculated: 361.2. $^1$H NMR (400 MHz, DMSO-d$_6$) δ 8.73-8.61 (m, 2H), 8.52 (s, 1H), 8.12-8.00 (m, 2H), 7.57-7.44 (m, 2H), 6.84-6.75 (m, 2H), 3.50-3.60 (m, 1H), 2.97 (dd, J=17.0, 5.4 Hz, 1H), 2.91 (s, 6H), 2.86 (d, J=6.6 Hz, 2H), 2.60 (dd, J=16.6, 8.8 Hz, 1H), 2.17 (d, J=19.0 Hz, 1H), 1.90 (p, J=8.2 Hz, 1H).

Example E2.1. N-(3-fluorophenyl)-2-(4-pyridyl)-5,6,7,8-tetrahydropyrido[4,3-d]pyrimidin-4-amine

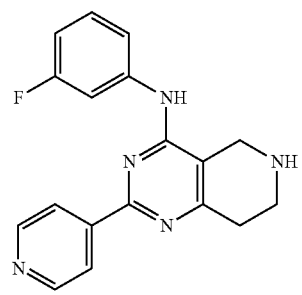 [SMILES: Fc1cccc(Nc2nc(-c3ccncc3)nc3c2CNCC3)c1]

Step 1. Synthesis of 6-benzyl-2-chloro-N-(3-fluorophenyl)-7,8-dihydro-5H-pyrido[4,3-d]pyrimidin-4-amine (Compound C2.1)

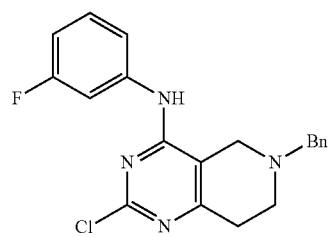 [SMILES: Fc1cccc(Nc2nc(Cl)nc3c2CN(Cc2ccccc2)CC3)c1]

Titled compound was obtained using compound B2 (140 mg, 0.48 mmol) and 3-Fluoroaniline (0.06 ml, 0.57 mmol) following the general procedure C method 1 previously described at 100° C. for 72 h. Final normal phase purification (cyclohexane/TBME from 90:100 to 50:50) afforded pure title compound (73 mg, yield 42%). Rt=2.85 min (gradient 2); MS (ESI) m/z: 369.1 [M-H]$^+$, [M-H]$^+$ calculated: 369.1. $^1$H NMR (400 MHz, DMSO-d$_6$) δ 8.86 (s, 1H), 7.61-7.45 (m, 1H), 7.44-7.31 (m, 7H), 7.31-7.23 (m, 1H), 6.99-6.88 (m, 1H), 3.76 (s, 2H), 3.54 (s, 2H), 2.72 (s, 4H).

Step 2. Synthesis of 6-benzyl-N-(3-fluorophenyl)-2-(4-pyridyl)-7,8-dihydro-5H-pyrido[4,3-d]pyrimidin-4-amine (Compound D2.1)

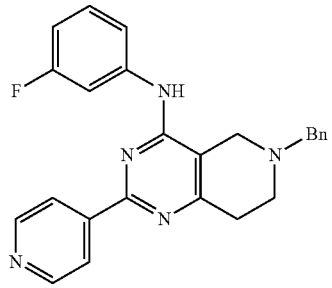 [SMILES: Fc1cccc(Nc2nc(-c3ccncc3)nc3c2CN(Cc2ccccc2)CC3)c1]

Titled compound was obtained using compound C2.1 (74 mg, 0.20 mmol) and Pyridine-4-boronic acid (32.9 mg, 0.24 mmol) following the general procedure D previously described. Final normal phase purification (cyclohexane/AcOEt from 50:50 to 20:80) afforded pure title compound (65.2 mg, yield 79%). Rt=2.96 min (gradient 2); MS (ESI) m/z: 412.2 [M-H]$^+$, [M-H]$^+$ calculated: 412.2. $^1$H NMR (400 MHz, DMSO-d$_6$) δ 8.70 (dd, J=4.4, 1.7 Hz, 3H), 8.17-8.04 (m, 2H), 7.67 (dt, J=12.0, 2.3 Hz, 1H), 7.56 (ddd, J=8.3, 2.0, 0.9 Hz, 1H), 7.45-7.39 (m, 3H), 7.39-7.34 (m, 2H), 7.32-7.25 (m, 1H), 6.91 (tdd, J=8.5, 2.6, 0.9 Hz, 1H), 3.80 (s, 2H), 3.65 (s, 2H), 2.87 (t, J=5.8 Hz, 2H), 2.78 (t, J=6.1 Hz, 2H).

Step 3. Synthesis of N-(3-fluorophenyl)-2-(4-pyridyl)-5,6,7,8-tetrahydropyrido[4,3-d]pyrimidin-4-amine (Compound E2.1)

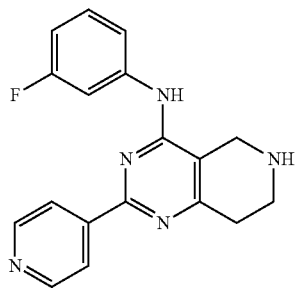 [SMILES: Fc1cccc(Nc2nc(-c3ccncc3)nc3c2CNCC3)c1]

Titled compound was obtained using compound D2.1 (60.0 mg, 0.14 mmol) following the general procedure E previously described for 4 hours. Final normal phase purification (DCM/DCM:NH$_3$ 1N MeOH 4:1 from 95:5 to 60:40) afforded pure title compound (30.2 mg, yield 52%). Rt=1.68 min (gradient 1); MS (ESI) m/z: 322.1 [M-H]$^+$, [M-H]$^+$ calculated: 322.1. $^1$H NMR (400 MHz, DMSO-d$_6$) δ 8.70 (td, J=4.2, 1.6 Hz, 2H), 8.57 (d, J=5.3 Hz, 1H), 8.10 (td, J=4.6, 1.6 Hz, 2H), 7.74 (dt, J=12.1, 2.3 Hz, 1H), 7.62 (ddd, J=8.3, 2.0, 0.9 Hz, 1H), 7.50-7.31 (m, 1H), 6.90 (tt, J=8.4, 2.4 Hz, 1H), 3.82 (d, J=3.6 Hz, 2H), 3.02 (td, J=5.9, 2.6 Hz, 2H), 2.74 (q, J=5.4 Hz, 2H).

Example E2.2. N-(3-fluorophenyl)-2-(4-pyridyl)-5,6,7,8-tetrahydropyrido[4,3-d]pyrimidin-4-amine

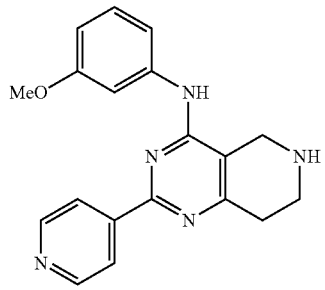 [SMILES: COc1cccc(Nc2nc(-c3ccncc3)nc3c2CNCC3)c1]

Step 1. Synthesis of 6-benzyl-2-chloro-N-(3-methoxyphenyl)-7,8-dihydro-5H-pyrido[4,3-d]pyrimidin-4-amine (Compound C2.2)

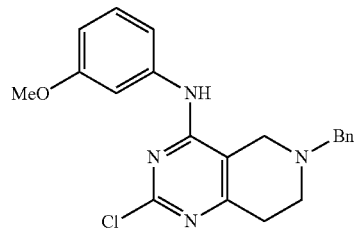 [SMILES: COc1cccc(Nc2nc(Cl)nc3c2CN(Cc2ccccc2)CC3)c1]

Titled compound was obtained using compound B2 (150 mg, 0.51 mmol) and m-methoxyaniline (0.07 ml, 0.56 mmol) following the general procedure C method 1 previously described at 100° C. for 16 h. Final normal phase purification (cyclohexane/AcOEt from 95:5 to 60:40) afforded pure title compound (150 mg, yield 58%). Rt=1.39 min (gradient 2); MS (ESI) m/z: 381.2 [M-H]$^+$, [M-H]$^+$ calculated: 381.1. $^1$H NMR (400 MHz, DMSO-d$_6$) δ 8.70 (s, 1H), 7.43-7.32 (m, 4H), 7.30-7.25 (m, 1H), 7.24 (s, 1H), 7.24-7.20 (m, 1H), 7.15 (ddd, J=8.0, 2.0, 1.0 Hz, 1H), 6.69 (ddd, J=8.2, 2.6, 1.0 Hz, 1H), 3.76 (s, 2H), 3.74 (s, 3H), 3.52 (s, 2H), 2.71 (s, 4H).

Step 2. Synthesis of 6-benzyl-N-(3-methoxyphenyl)-2-(4-pyridyl)-7,8-dihydro-5H-pyrido[4,3-d]pyrimidin-4-amine (Compound D2.2)

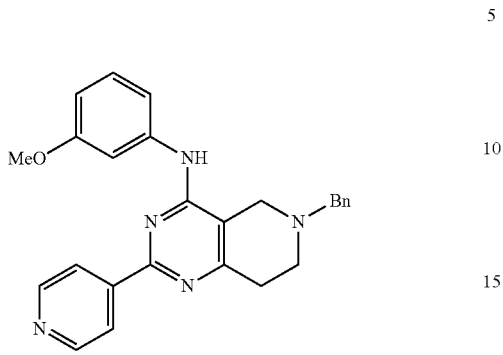

Titled compound was obtained using compound C2.2 (145 mg, 0.38 mmol) and Pyridine-4-boronic acid (62.4 mg, 0.46 mmol) following the general procedure D previously described. Final normal phase purification (cyclohexane/AcOEt from 50:50 to 30:70) afforded pure title compound (130 mg, yield 81%). Rt=1.52 min (gradient 2); MS (ESI) m/z: 424.3 [M-H]$^+$, [M-H]$^+$ calculated: 424.2. $^1$H NMR (400 MHz, DMSO-d$_6$) δ 8.74-8.64 (m, 2H), 8.52 (s, 1H), 8.28-7.98 (m, 2H), 7.45-7.25 (m, 8H), 6.67 (ddd, J=7.9, 2.5, 1.2 Hz, 1H), 3.79 (s, 2H), 3.78 (s, 3H), 3.64 (s, 2H), 2.85 (t, J=5.8 Hz, 2H), 2.78 (t, J=5.6 Hz, 2H).

Step 3. N-(3-methoxyphenyl)-2-(4-pyridyl)-5,6,7,8-tetrahydropyrido[4,3-d]pyrimidin-4-amine (Compound E2.2)

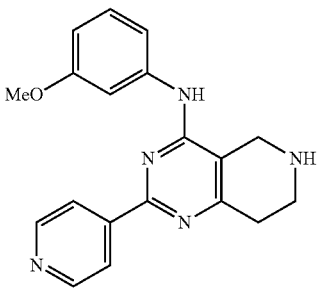

Titled compound was obtained using compound D2.2 (125.0 mg, 0.30 mmol) following the general procedure E previously described for 4 hours. Final normal phase purification (DCM/DCM:NH$_3$ 1N MeOH 4:1 from 95:5 to 75:25) afforded pure title compound (71.8 mg, yield 73%). Rt=1.47 min (gradient 1); MS (ESI) m/z: 334.2 [M-H]$^+$, [M-H]$^+$ calculated: 334.2. $^1$H NMR (400 MHz, DMSO-d$_6$) δ 8.74-8.66 (m, 2H), 8.39 (s, 1H), 8.17-8.09 (m, 2H), 7.47 (t, J=2.2 Hz, 1H), 7.39 (ddd, J=8.1, 2.0, 1.0 Hz, 1H), 7.28 (t, J=8.1 Hz, 1H), 6.67 (ddd, J=8.2, 2.6, 0.9 Hz, 1H), 3.82 (s, 2H), 3.78 (s, 3H), 3.31 (s, 1H), 3.03 (t, J=5.8 Hz, 2H), 2.73 (t, J=5.8 Hz, 2H).

Example E2.3. N1-[2-(4-pyridyl)-5,6,7,8-tetrahydropyrido[4,3-d]pyrimidin-4-yl]benzene-1,3-diamine

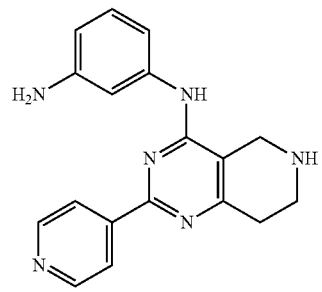

Step 1. Synthesis of tert-butyl N-[3-[(6-benzyl-2-chloro-7,8-dihydro-5H-pyrido[4,3-d]pyrimidin-4-yl)amino]phenyl]carbamate (Compound C2.3)

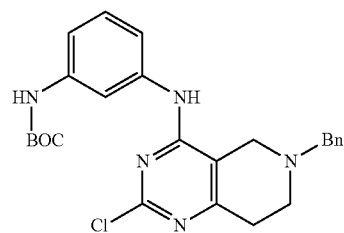

Titled compound was obtained using compound B2 (200 mg, 0.68 mmol) and N-Boc-m-phenylenediamine (158.9 mg, 0.75 mmol) following the general procedure C method 1 previously described at 100° C. for 16 h. Normal phase purification (cyclohexane/AcOEt from 85:15 to 75:25) afforded tert-butyl N-[3-[(6-benzyl-2-chloro-7,8-dihydro-5H-pyrido[4,3-d]pyrimidin-4yl)amino]phenyl]carbamate (130 mg, yield 41%). Rt=1.61 min (gradient 2); MS (ESI) m/z: 466.2 [M-H]$^+$, [M-H]$^+$ calculated: 466.2. $^1$H NMR (400 MHz, DMSO-d$_6$) δ 9.37 (s, 1H), 8.75 (s, 1H), 7.65 (q, J=1.5 Hz, 1H), 7.42-7.32 (m, 4H), 7.30-7.24 (m, 1H), 7.23-7.16 (m, 2H), 7.16-7.09 (m, 1H), 3.75 (s, 2H), 3.51 (s, 2H), 2.71 (d, J=2.4 Hz, 4H), 1.48 (s, 9H).

Step 2. Synthesis of tert-butyl N-[3-[[6-benzyl-2-(4-pyridyl)-7,8-dihydro-5H-pyrido[4,3-d]pyrimidin-4-yl]amino]phenyl]carbamate (Compound D2.3)

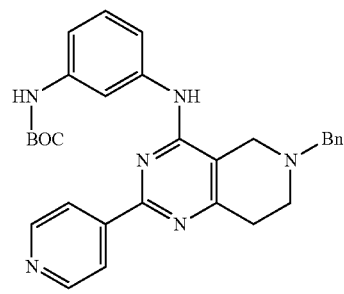 [SMILES: CC(C)(C)OC(=O)Nc1cccc(Nc2nc(-c3ccncc3)nc3c2CN(Cc2ccccc2)CC3)c1]

Titled compound was obtained using compound C2.3 (125 mg, 0.27 mmol) and Pyridine-4-boronic acid (44.0 mg, 0.32 mmol) following the general procedure D previously described. Final normal phase purification (cyclohexane/AcOEt from 30:70 to 10:90) afforded pure title compound (98 mg, yield 72%). Rt=1.67 min (gradient 2); MS (ESI) m/z: 509.3 [M-H]$^+$, [M-H]$^+$ calculated: 509.3. $^1$H NMR (400 MHz, DMSO-d$_6$) δ 9.37 (s, 1H), 8.74-8.58 (m, 2H), 8.51 (s, 1H), 8.21-8.16 (m, 2H), 8.15 (s, 1H), 7.47-7.39 (m, 2H), 7.37 (dd, J=8.4, 6.7 Hz, 2H), 7.32-7.24 (m, 2H), 7.22 (t, J=7.9 Hz, 1H), 7.00 (dt, J=7.9, 1.6 Hz, 1H), 3.79 (s, 2H), 3.63 (s, 2H), 2.85 (t, J=5.8 Hz, 2H), 2.78 (t, J=5.4 Hz, 2H), 1.49 (s, 9H).

Step 3. N1-[2-(4-pyridyl)-5,6,7,8-tetrahydropyrido[4,3-d]pyrimidin-4-yl]benzene-1,3-diamine (Compound E2.3)

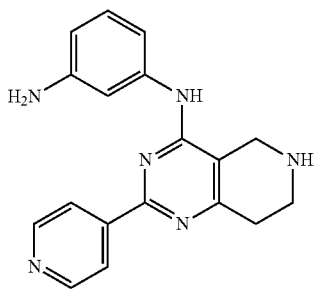 [SMILES: Nc1cccc(Nc2nc(-c3ccncc3)nc3c2CNCC3)c1]

Titled compound was obtained solving compound D2.3 (95.0 mg, 0.19 mmol) in 1,4-dioxane (0.5 ml), a solution of HCl (4M) in 1,4-dioxane (0.5 ml) was dropwise added and the reaction mixture stirred at room temperature for 6 h, then the reaction crude was concentrated to dryness at low pressure, the resulting crude portioned between DCM (20 ml) and NaOH 0.1 M (20 ml), the organic layer dried over Na$_2$SO$_4$ and concentrated to dryness at low pressure. Resulting solid (75 mg, 0.18 mmol) was treated following the general procedure E previously described for 4 hours. Final normal phase purification (DCM/DCM:NH$_3$ 1N MeOH 4:1 from 95:5 to 75:25) afforded pure title compound (18.7 mg, yield 32%). Rt=1.17 min (gradient 1); MS (ESI) m/z: 319.2 [M-H]$^+$, [M-H]$^+$ calculated: 319.4. $^1$H NMR (400 MHz, DMSO-d$_6$) δ 8.71-8.63 (m, 2H), 8.17-8.10 (m, 3H), 7.06-6.99 (m, 2H), 6.90 (dd, J=8.2, 1.9 Hz, 1H), 6.33 (dd, J=8.0, 2.1 Hz, 1H), 5.09 (s, 2H), 3.77 (s, 2H), 3.01 (t, J=5.7 Hz, 2H), 2.71 (t, J=5.7 Hz, 2H).

Example E2.4. N3-methyl-N1-[2-(4-pyridyl)-5,6,7,8-tetrahydropyrido[4,3-d]pyrimidin-4-yl]benzene-1,3-diamine

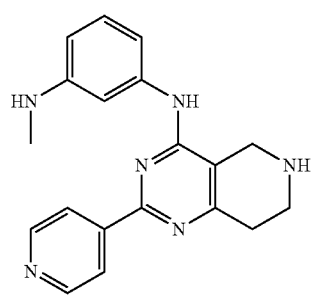

Step 1. Synthesis of tert-butyl N-[3-[(6-benzyl-2-chloro-7,8-dihydro-5H-pyrido[4,3-d]pyrimidin-4-yl)amino]phenyl]-N-methyl-carbamate (Compound C2.4)

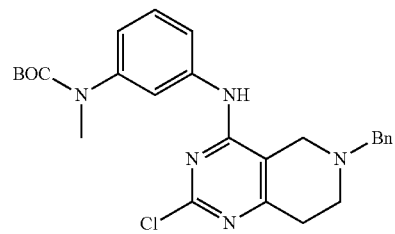 [SMILES: CN(C(=O)OC(C)(C)C)c1cccc(Nc2nc(Cl)nc3c2CN(Cc2ccccc2)CC3)c1]

Titled compound was obtained using compound B2 (200 mg, 0.68 mmol) and 3-(N-tert-Butoxycarbonyl-N-methylamino)aniline (175.0 mg, 0.75 mmol) following the general procedure C method 1 previously described at 100° C. for 16 h. Final normal phase purification (cyclohexane/AcOEt from 85:15 to 65:35) afforded titled compound. Rt=1.80 min (gradient 2); MS (ESI) m/z: 480.0 [M-H]$^+$, [M-H]$^+$ calculated: 480.2. $^1$H NMR (400 MHz, DMSO-d$_6$) δ 8.74 (s, 1H), 7.50 (t, J=2.1 Hz, 1H), 7.43-7.24 (m, 8H), 7.02 (ddd, J=7.9, 2.2, 1.0 Hz, 1H), 3.76 (s, 2H), 3.53 (s, 2H), 3.18 (s, 3H), 2.72 (s, 4H), 1.40 (s, 9H).

Step 2. Synthesis of tert-butyl N-[3-[[6-benzyl-2-(4-pyridyl)-7,8-dihydro-5H-pyrido[4,3-d]pyrimidin-4-yl]amino]phenyl]-N-methyl-carbamate (Compound D2.4)

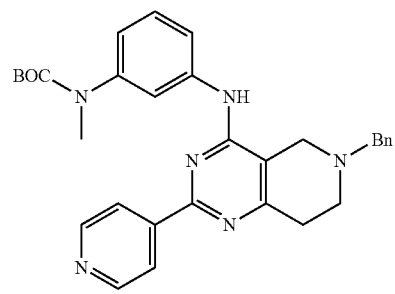 [SMILES: CN(C(=O)OC(C)(C)C)c1cccc(Nc2nc(-c3ccncc3)nc3c2CN(Cc2ccccc2)CC3)c1]

Titled compound was obtained using compound C2.4 (92 mg, 0.19 mmol) and Pyridine-4-boronic acid (31.4 mg, 0.23 mmol) following the general procedure D previously described. Final normal phase purification (cyclohexane/AcOEt from 85:15 to 30:70) afforded pure title compound (86 mg, yield 86%). Rt=1.87 min (gradient 2); MS (ESI) m/z: 523.3 [M-H]$^+$, [M-H]$^+$ calculated: 523.3. $^1$H NMR (400 MHz, DMSO-d$_6$) δ 8.70-8.64 (m, 2H), 8.60 (s, 1H), 8.16-8.10 (m, 2H), 7.65 (t, J=2.1 Hz, 1H), 7.60-7.54 (m, 1H), 7.46-7.40 (m, 2H), 7.40-7.32 (m, 3H), 7.32-7.25 (m, 1H), 7.00 (ddd, J=8.0, 2.2, 1.0 Hz, 1H), 3.80 (s, 2H), 3.64 (s, 2H), 3.22 (s, 3H), 2.85 (d, J=5.6 Hz, 2H), 2.78 (t, J=5.5 Hz, 2H), 1.40 (d, J=1.1 Hz, 9H).

Step 3. N3-methyl-N1-[2-(4-pyridyl)-5,6,7,8-tetrahydropyrido[4,3-d]pyrimidin-4-yl]benzene-1,3-diamine (Compound E2.4)

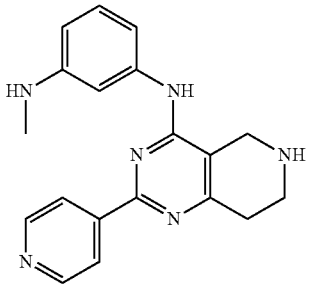 [SMILES: CNc1cccc(Nc2nc(-c3ccncc3)nc3c2CNCC3)c1]

Titled compound was obtained solving compound D2.4 (95.0 mg, 0.19 mmol) in 1,4-dioxane (0.4 ml), a solution of HCl (4M) in 1,4-dioxane (0.4 ml) was dropwise added and the reaction mixture stirred at room temperature for 3 h, then the reaction crude was concentrated to dryness at low pressure, the resulting crude portioned between DCM (20 ml) and NaOH 0.1 M (20 ml), the organic layer dried over $Na_2SO_4$ and concentrated to dryness at low pressure. Resulting crude (66 mg, 0.16 mmol) was treated following the general procedure E previously described for 4 hours. Final normal phase purification (DCM/DCM:$NH_3$ 1N MeOH 4:1 from 95:5 to 75:25) afforded pure title compound (16.1 mg, yield 31%). Rt=1.36 min (gradient 1); MS (ESI) m/z: 333.3 [M-H]$^+$, [M-H]$^+$ calculated: 333.2. $^1$H NMR (400 MHz, DMSO-$d_6$) δ 8.81-8.56 (m, 2H), 8.18 (s, 1H), 8.16-8.11 (m, 2H), 7.11-7.00 (m, 2H), 6.95 (ddd, J=8.0, 2.1, 1.0 Hz, 1H), 6.30 (ddd, J=8.1, 2.3, 1.0 Hz, 1H), 5.66 (q, J=5.0 Hz, 1H), 3.79 (s, 2H), 3.02 (t, J=5.8 Hz, 2H), 2.71 (t, J=5.6 Hz, 5H).

Example E2.5. N3,N3-dimethyl-N1-[2-(4-pyridyl)-5,6,7,8-tetrahydropyrido[4,3-d]pyrimidin-4-yl]benzene-1,3-diamine

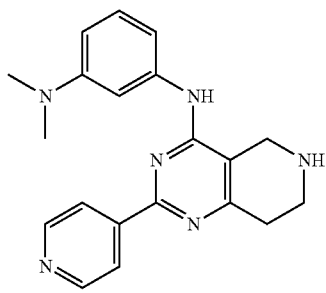 [SMILES: CN(C)c1cccc(Nc2nc(-c3ccncc3)nc3c2CNCC3)c1]

Step 1. Synthesis of N1-(6-benzyl-2-chloro-7,8-dihydro-5H-pyrido[4,3-d]pyrimidin-4-yl)-N3,N3-dimethyl-benzene-1,3-diamine (Compound C2.5)

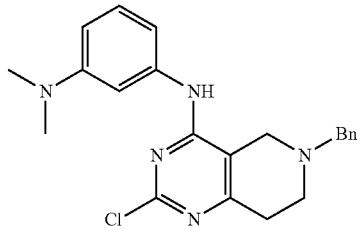 [SMILES: CN(C)c1cccc(Nc2nc(Cl)nc3c2CN(Cc2ccccc2)CC3)c1]

Titled compound was obtained using compound B2 (250 mg, 0.85 mmol) and N,N-Dimethyl-1,3-phenylenediamine dihydrochloride (197.4 mg, 0.93 mmol) following the general procedure C method 1 previously described at 100° C. for 16 h. Final normal phase purification (cyclohexane/AcOEt from 80:20 to 60:40) afforded pure title compound (227.6 mg, yield 68%). Rt=1.12 min (gradient 2); MS (ESI) m/z: 394.2 [M-H]$^+$, [M-H]$^+$ calculated: 394.2. $^1$H NMR (400 MHz, DMSO-$d_6$) δ 8.58 (s, 1H), 7.43-7.31 (m, 4H), 7.31-7.24 (m, 1H), 7.13 (t, J=8.1 Hz, 1H), 6.95 (t, J=2.2 Hz, 1H), 6.88 (ddd, J=8.0, 2.0, 0.8 Hz, 1H), 6.50 (ddd, J=8.4, 2.5, 0.9 Hz, 1H), 3.75 (s, 2H), 3.51 (s, 2H), 2.88 (s, 6H), 2.70 (d, J=2.4 Hz, 4H).

Step 2. Synthesis of N1-[6-benzyl-2-(4-pyridyl)-7,8-dihydro-5H-pyrido[4,3-d]pyrimidin-4-yl]-N3,N3-dimethyl-benzene-1,3-diamine (Compound D2.5)

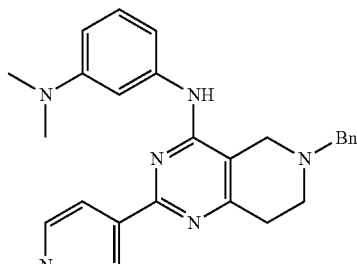

Titled compound was obtained using compound C2.5 (220 mg, 0.56 mmol) and Pyridine-4-boronic acid (91.5 mg, 0.67 mmol) following the general procedure D previously described. Final normal phase purification (cyclohexane/AcOEt from 70:30 to 20:80) afforded pure title compound (185 mg, yield 76%). Rt=1.43 min (gradient 2); MS (ESI) m/z: 437.2 [M-H]$^+$, [M-H]$^+$ calculated: 437.2. $^1$H NMR (400 MHz, DMSO-$d_6$): δ 8.70-8.64 (m, 2H), 8.36 (s, 1H), 8.17-8.09 (m, 2H), 7.48-7.39 (m, 2H), 7.39-7.33 (m, 2H), 7.31-7.25 (m, 1H), 7.23-7.13 (m, 2H), 7.06 (ddd, J=7.9, 2.0, 0.9 Hz, 1H), 6.49 (ddd, J=8.3, 2.6, 0.9 Hz, 1H), 3.79 (s, 2H), 3.63 (s, 2H), 2.92 (s, 6H), 2.84 (t, J=5.2 Hz, 2H), 2.77 (t, J=5.4 Hz, 2H).

Step 3. N3,N3-dimethyl-N1-[2-(4-pyridyl)-5,6,7,8-tetrahydropyrido[4,3-d]pyrimidin-4-yl]benzene-1,3-diamine (Compound E2.5)

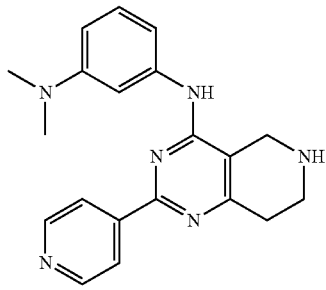 [SMILES: CN(C)c1cccc(Nc2nc(-c3ccncc3)nc3c2CNCC3)c1]

Titled compound was obtained using compound D2.5 (180.0 mg, 0.41 mmol) following the general procedure E previously described for 4 hours. Final normal phase purification (DCM/DCM:NH$_3$ 1N MeOH 4:1 from 70:30 to 20:80) afforded pure title compound (62.8 mg, yield 44%). Rt=1.55 min (gradient 1); MS (ESI) m/z: 347.2 [M-H]$^+$, [M-H]$^+$ calculated: 347.2. $^1$H NMR (400 MHz, DMSO-d$_6$): δ 8.71-8.65 (m, 2H), 8.22 (s, 1H), 8.17-8.10 (m, 2H), 7.25-7.13 (m, 2H), 7.12 (dt, J=8.2, 1.3 Hz, 1H), 6.48 (ddd, J=8.1, 2.5, 1.1 Hz, 1H), 3.80 (s, 2H), 3.02 (t, J=5.8 Hz, 2H), 2.92 (s, 6H), 2.72 (t, J=5.8 Hz, 2H).

Example E2.6. 4-[[2-(4-pyridyl)-5,6,7,8-tetrahydropyrido[4,3-d]pyrimidin-4-yl]amino]phenol

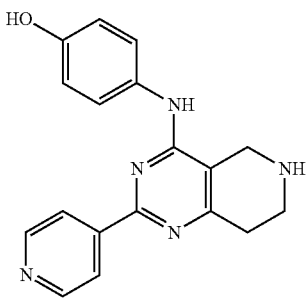 [SMILES: Oc1ccc(Nc2nc(-c3ccncc3)nc3c2CNCC3)cc1]

Step 1. Synthesis of 4-[(6-benzyl-2-chloro-7,8-dihydro-5H-pyrido[4,3-d]pyrimidin-4-yl)amino]phenol (Compound C2.6)

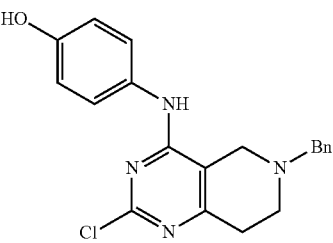 [SMILES: Oc1ccc(Nc2nc(Cl)nc3c2CN(Cc2ccccc2)CC3)cc1]

Titled compound was obtained using compound B2 (200 mg, 0.68 mmol) and p-aminophenol (82.4 mg, 0.75 mmol) following the general procedure C method 1 previously described at 100° C. for 16 h. Final normal phase purification (cyclohexane/AcOEt from 85:15 to 50:50) afforded pure title compound (149 mg, yield 60%). Rt=0.74 min (gradient 2); MS (ESI) m/z: 366.1/368.1 [M-H]$^+$, [M-H]$^+$ calculated: 366.1/368.1. $^1$H NMR (400 MHz DMSO-d$_6$) δ 9.32 (s, 1H), 8.57 (s, 1H), 7.46-7.31 (m, 4H), 7.30-7.24 (m, 1H), 7.23-7.12 (m, 2H), 6.81-6.65 (m, 2H), 3.74 (s, 2H), 3.45 (s, 2H), 2.78-2.59 (m, 4H).

Step 2. 4-[[6-benzyl-2-(4-pyridyl)-7,8-dihydro-5H-pyrido[4,3-d]pyrimidin-4-yl]amino]phenol (Compound D2.6)

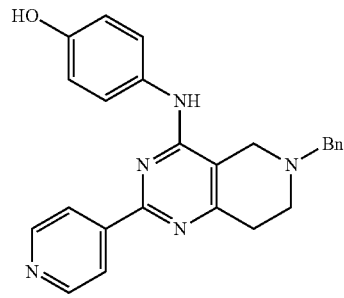 [SMILES: Oc1ccc(Nc2nc(-c3ccncc3)nc3c2CN(Cc2ccccc2)CC3)cc1]

Titled compound was obtained using compound C2.6 (148 mg, 0.40 mmol) and Pyridine-4-boronic acid (72.1 mg, 0.49 mmol) following the general procedure D previously described. Final normal phase purification (cyclohexane/AcOEt from 60:40 to 30:70) afforded pure title compound (75 mg, yield 46%). Rt=0.77 min (gradient 2); MS (ESI) m/z: 410.2 [M-H]$^+$, [M-H]$^+$ calculated: 410.2. $^1$H NMR (400 MHz, DMSO-d$_6$) δ 9.27 (s, 1H), 8.69-8.61 (m, 2H), 8.37 (s, 1H), 8.09-8.02 (m, 2H), 7.44-7.32 (m, 6H), 7.31-7.25 (m, 1H), 6.78 (d, J=8.8 Hz, 2H), 3.77 (s, 2H), 3.56 (s, 2H), 2.84-2.71 (m, 4H).

Step 3. 4-[[2-(4-pyridyl)-5,6,7,8-tetrahydropyrido[4,3-d]pyrimidin-4-yl]amino]phenol (Compound E2.6)

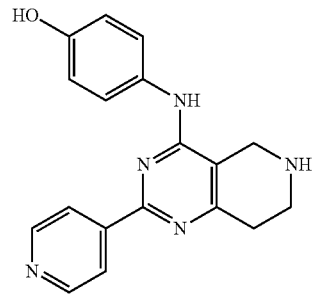 [SMILES: Oc1ccc(Nc2nc(-c3ccncc3)nc3c2CNCC3)cc1]

Titled compound was obtained using compound D2.6 (75.0 mg, 0.18 mmol) following the general procedure E previously NH described for 5 hours. Final normal phase purification (DCM/DCM:NH$_3$ 1M MeOH 4:1 from 95:5 to 75:25) afforded pure title compound (26.9 mg, yield 47%). Rt=1.32 min (gradient 1); MS (ESI) m/z: 320.1 [M-H]$^+$, [M-H]$^+$ calculated: 320.1. $^1$H NMR (400 MHz, DMSO-d$_6$) δ 8.67-8.64 (m, 2H), 8.32 (s, 1H), 8.31 (s, 1H), 8.08-8.04 (m, 2H), 7.46-7.40 (m, 2H), 6.82-6.76 (m, 2H), 3.79 (s, 2H), 3.06 (t, J=5.8 Hz, 2H), 2.73 (t, J=5.9 Hz, 2H).

Example E2.7

N-(2-fluorophenyl)-2-(4-pyridyl)-5,6,7,8-tetrahydropyrido[4,3-d]pyrimidin-4-amine

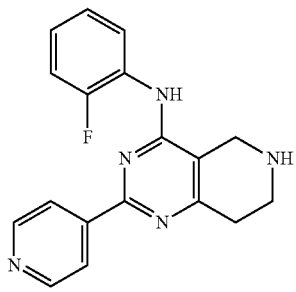 [SMILES: Fc1ccccc1Nc1nc(-c2ccncc2)nc2c1CNCC2]

Step 1. Synthesis of 6-benzyl-2-chloro-N-(2-fluorophenyl)-7,8-dihydro-5H-pyrido[4,3-d]pyrimidin-4-amine (Compound C2.7)

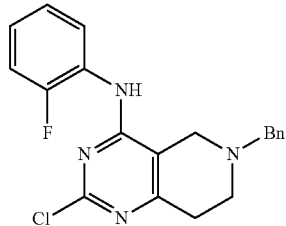 [SMILES: Fc1ccccc1Nc1nc(Cl)nc2c1CN(Cc1ccccc1)CC2]

A mixture of Pd(OAc)$_2$ (7.8 mg, 0.03 mmol) and rac-BINAP (21.6 mg, 0.03 mmol) in 1,4-dioxane (3.4 ml) was stirred under Ar flushing for 10 minutes. Then were stepwise added compound B2 (200 mg, 0.68 mmol), o-fluoroaniline (0.066 ml, 0.68 mmol) and Cs$_2$CO$_3$ (268.5 mmol, 0.82 mmol). The reaction mixture was stirred in a CEM® microwave apparatus at 80° C. for 1.5 h, filtrated through a celite coarse patch, rinsed with DCM and concentrated to dryness at low pressure. Final normal phase purification (cyclohexane/AcOEt from 95:5 to 75:25) yielded a mixture where titled compound was the majority one. Resulting crude (205 mg) was used in the next step without any further purification process. Rt=1.25 min (gradient 2, 77% purity); MS (ESI) m/z: 367.1/369.1 [M-H]$^+$, [M-H]$^+$ calculated: 367.1/369.1.

Step 2. 6-benzyl-N-(2-fluorophenyl)-2-(4-pyridyl)-7,8-dihydro-5H-pyrido[4,3-d]pyrimidin-4-amine (Compound D2.7)

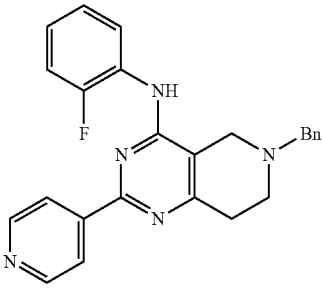 [SMILES: Fc1ccccc1Nc1nc(-c2ccncc2)nc2c1CN(Cc1ccccc1)CC2]

Titled compound was obtained using crude C2.7 (205 mg, 0.56 mmol estimated) and Pyridine-4-boronic acid (91.1 mg, 0.67 mmol) following the general procedure D previously described. Final normal phase purification (cyclohexane/AcOEt from 85:15 to 45:55) afforded pure title compound (149 mg, average yield 65% from previous step). Rt=1.37 min (gradient 2); MS (ESI) m/z: 412.2 [M-H]$^+$, [M-H]$^+$ calculated: 412.2. $^1$H NMR (400 MHz, DMSO-d$_6$) δ 8.67-8.55 (m, 3H), 8.00-7.88 (m, 2H), 7.50 (td, J=7.8, 1.8 Hz, 1H), 7.45-7.40 (m, 2H), 7.40-7.34 (m, 2H), 7.34-7.20 (m, 4H), 3.79 (s, 2H), 3.60 (s, 2H), 2.86 (t, J=5.7 Hz, 2H), 2.81 (d, J=5.0 Hz, 2H).

Step 3. N-(2-fluorophenyl)-2-(4-pyridyl)-5,6,7,8-tetrahydropyrido[4,3-d]pyrimidin-4-amine (Compound E2.7)

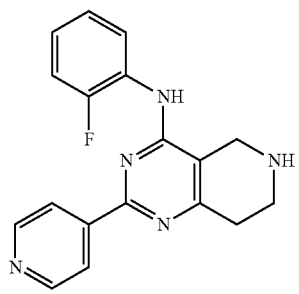 [SMILES: Fc1ccccc1Nc1nc(-c2ccncc2)nc2c1CNCC2]

Titled compound was obtained using compound D2.7 (140.0 mg, 0.34 mmol) following the general procedure E previously described for 6 hours. Final normal phase purification (DCM/DCM:NH$_3$ 1M MeOH 4:1 from 95:5 to 75:25) afforded pure title compound (72.2 mg, yield 66%). Rt=0.33 min (gradient 2); MS (ESI) m/z: 322.2 [M-H]$^+$, [M-H]$^+$ calculated: 322.1. 1H NMR (400 MHz, DMSO-d$_6$) δ 8.67-8.58 (m, 2H), 8.53 (s, 1H), 8.00-7.90 (m, 2H), 7.54 (td, J=7.8, 2.0 Hz, 1H), 7.38-7.20 (m, 3H), 3.85 (s, 2H), 3.09 (t, J=5.8 Hz, 2H), 2.76 (t, J=5.8 Hz, 2H).

Example E3

N4-(3-fluorophenyl)-2-(4-pyridyl)quinazoline-4,6-diamine

Reaction A Scheme 2

Synthesis of 6-nitro-1H-quinazoline-2,4-dione (Compound A3 Scheme 2)

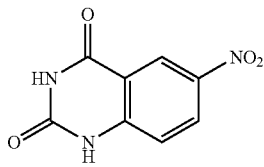 [SMILES: O=c1[nH]c(=O)c2cc([N+](=O)[O-])ccc2[nH]1]

A mixture of 2-Amino-5-nitrobenzoic acid (3200 mg, 17.04 mmol) and urea (10338.4 mg, 170.43 mmol) was stirred for 4 hours at 160° C. in a CEM® microwave apparatus. The reaction crude was triturated in water (20 ml) and filtered. Resulting solid was separated by filtration and aqueous filtrate extracted twice with ethyl acetate (2×25 ml). Combined organic layers were dried over $Na_2SO_4$, filtered, concentrated to dryness at low pressure and resulting solid mixed with the previous one obtained by filtration. Final trituration in methanol (5 ml) and filtration of combined solids afforded pure title compound (3353.7 mg, yield 95%). Rt=1.25 min; MS (ESI) m/z: 206.0 [M-H]$^-$, [M-H]$^-$ calculated: 206.0. $^1$H NMR (400 MHz, DMSO-d$_6$) δ 11.72 (s, 2H), 8.59 (d, J=2.7 Hz, 1H), 8.45 (dd, J=9.0, 2.7 Hz, 1H), 7.32 (d, J=9.0 Hz, 1H).

Reaction B Scheme 2

Synthesis of 2,4-dichloro-6-nitro-quinazoline (Compound B3 Scheme 2)

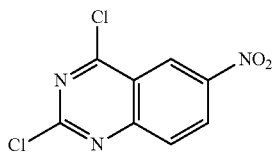 [SMILES: O=[N+]([O-])c1ccc2nc(Cl)nc(Cl)c2c1]

A suspension of 6-nitro-1H-quinazoline-2,4-dione (3530 mg, 17.04 mmol) and PCl$_5$ (18826.5 mg, 88.62 mmol) in POCl$_3$ (24.1 ml, 255.62 mmol) was stirred at 120° C. under N$_2$ for 4 hours. Then reaction crude was concentrated to dryness at low pressure and purification by typical silica gel flash chromatography (cyclohexane/AcOEt from 95:5 to 80:20) afforded the pure title compound as white solid (2412 mg, yield 58%). Rt=2.16 min; MS (ESI) m/z: 244.3 [M-H]$^+$, [M-H]$^+$ calculated: 244.3. $^1$H NMR (400 MHz, CDCl$_3$) δ 9.18 (d, J=2.4 Hz, 1H), 8.75 (dd, J=9.2, 2.5 Hz, 1H), 8.18 (d, J=9.2 Hz, 1H).

Reaction C Scheme 2

Synthesis of 2-chloro-N-(3-fluorophenyl)-6-nitro-quinazolin-4-amine (Compound C3 Scheme 2)

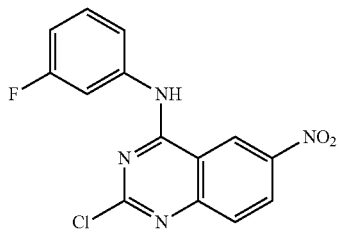 [SMILES: O=[N+]([O-])c1ccc2nc(Cl)nc(Nc3cccc(F)c3)c2c1]

A suspension of 2,4-dichloro-6-nitro-quinazoline (500 mg, 2.05 mmol), 2-Fluoroaniline (0.22 ml, 2.25 mmol) and diisopropylethylamine (0.49 ml, 3.28 mmol) in 2-propanol/DCM 4/1 (10 ml) was stirred at room temperature for 3 hours. Then reaction crude was concentrated to dryness at low pressure followed by normal phase purification (cyclohexane/AcOEt from 100:0 to 80:20) yielding titled compound (650 mg, yield 99%). Rt=2.72 min; MS (ESI) m/z: 319.1 [M-H]$^+$, [M-H]$^+$ calculated: 319.0. $^1$H NMR (400 MHz, DMSO-d$_6$) δ 10.87 (s, 1H), 9.68 (d, J=2.4 Hz, 1H), 8.60 (dd, J=9.1, 2.4 Hz, 1H), 7.90 (d, J=9.1 Hz, 1H), 7.79 (dt, J=11.4, 2.4 Hz, 1H), 7.64 (ddd, J=8.2, 2.4, 0.9 Hz, 1H), 7.51 (td, J=8.2, 6.7 Hz, 1H), 7.09 (tdd, J=8.5, 2.4, 0.9 Hz, 1H).

Reaction D Scheme 2. Synthesis of N-(3-fluorophenyl)-6-nitro-2-(4-pyridyl)quinazolin-4-amine (Compound D3 Scheme 2)

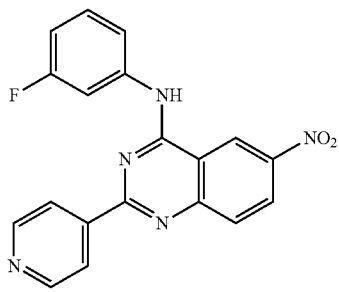 [SMILES: O=[N+]([O-])c1ccc2nc(-c3ccncc3)nc(Nc3cccc(F)c3)c2c1]

A suspension of 2-chloro-N-(3-fluorophenyl)-6-nitro-quinazolin-4-amine (650 mg, 2.04 mmol), Pyridine-4-boronic acid (334.3 mg, 2.45 mmol), PdCl$_2$(dppf) dichloromethane complex (78.5 mg, 0.10 mmol) and K$_2$CO$_3$ 2 M solution (2.04 ml, 4.08 mmol) in 1,4-dioxane (20.4 ml) was stirred in a CEM® microwave apparatus at 120° C. for 1 hour. Resulting crude was portioned between dichloromethane (25 ml), NaHCO$_3$ saturated solution (25 ml), the organic layer dried over Na$_2$SO$_4$ and concentrated to dryness at low pressure. Final normal phase purification (cyclohexane/AcOEt from 95:5 to 75:25) yielded titled compound (368 mg, yield 50%). Rt=2.80 min; MS (ESI) m/z: 362.2 [M-H]$^+$, [M-H]$^+$ calculated: 362.1. $^1$H NMR (400 MHz, DMSO-d$_6$) δ 10.69 (s, 1H), 9.75-9.62 (m, 1H), 8.85-8.74 (m, 2H), 8.61 (dd, J=9.2, 2.5 Hz, 1H), 8.28-8.23 (m, 2H), 8.07 (d, J=9.2

Hz, 1H), 7.90 (dt, J=11.7, 2.3 Hz, 1H), 7.78 (ddd, J=8.2, 2.0, 0.9 Hz, 1H), 7.55 (td, J=8.3, 6.8 Hz, 1H), 7.08 (tdd, J=8.5, 2.6, 0.9 Hz, 1H).

Reaction E Scheme 2. Synthesis of N4-(3-fluorophenyl)-2-(4-pyridyl)quinazoline-4,6-diamine (Compound E3 Scheme 2)

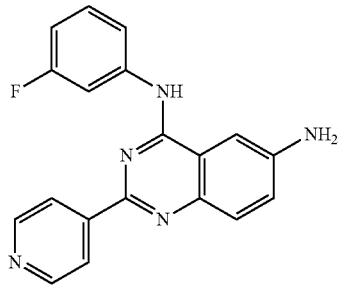 [SMILES: Nc1ccc2nc(-c3ccncc3)nc(Nc3cccc(F)c3)c2c1]

Under N₂ atmosphere, a suspension of N-(3-fluorophenyl)-6-nitro-2-(4-pyridyl)quinazolin-4-amine (365.0 mg, 0.99 mmol), ammonium formate (257 mg, 3.96 mmol) and Pd(OH)₂/C (73 mg) was stirred at reflux temperature for 4 hours. Catalyst was filtered off through a celite coarse patch and resulting filtrate concentrated to dryness at low pressure. Normal phase purification of filtrate (DCM/MeOH from 100:0 to 95:5) yielded titled compound (246 mg, yield 75%). Rt=2.21 min; MS (ESI) m/z: 332.1 [M-H]⁺, [M-H]⁺ calculated: 332.1. ¹H NMR (400 MHz, DMSO-d₆) δ 9.67 (s, 1H), 8.74-8.66 (m, 2H), 8.24-8.18 (m, 2H), 7.96 (dt, J=12.2, 2.3 Hz, 1H), 7.79 (ddd, J=8.3, 2.1, 0.8 Hz, 1H), 7.69 (d, J=8.9 Hz, 1H), 7.46 (td, J=8.2, 6.9 Hz, 1H), 7.40 (d, J=2.4 Hz, 1H), 7.32 (dd, J=8.9, 2.3 Hz, 1H), 6.94 (tdd, J=8.4, 2.6, 0.8 Hz, 1H), 5.82 (s, 2H).

Example E5

N-(3-fluorophenyl)-2-(4-pyridyl)-5,6,7,8-tetrahydropyrido[4,3-d]pyrimidin-4-amine

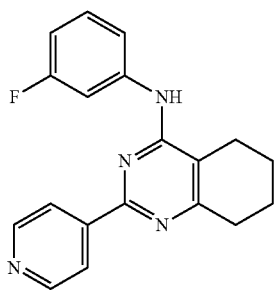 [SMILES: Fc1cccc(Nc2nc(-c3ccncc3)nc3c2CCCC3)c1]

Step 1. Synthesis of 5,6,7,8-tetrahydro-1H-quinazoline-2,4-dione (Compound A3, Scheme 1)

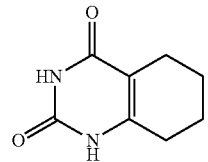 [SMILES: O=c1[nH]c2c(c(=O)[nH]1)CCCC2]

Titled compound was obtained using compound 3 (10000.0 mg, 55.81 mmol) following the general procedure A previously described and affording pure title compound (8440 mg, yield 91%). Rt=1.01 min (gradient 1); MS (ESI) m/z: 167.1 [M-H]⁺, [M-H]⁺ calculated: 167.1. ¹H NMR (400 MHz, DMSO-d₆) δ 10.71 (s, 2H), 2.29 (t, J=6.1 Hz, 2H), 2.13 (t, J=6.0 Hz, 2H), 1.61 (dddd, J=17.5, 9.3, 7.6, 4.6 Hz, 4H).

Step 2. Synthesis of 2,4-dichloro-5,6,7,8-tetrahydroquinazoline (Compound B3, Scheme 1)

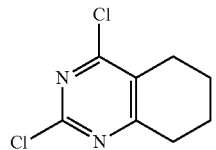

Titled compound was obtained using compound A3 (3000 mg, 18.05 mmol) following the general procedure B previously described and affording pure title compound (2055 mg, yield 56%). Rt=2.21 min (gradient 1); MS (ESI) m/z: 203.1/205.1/207.1 [M-H]⁺, [M-H]⁺ calculated: 203.1/205.1/207.1. ¹H NMR (400 MHz, CDCl₃) δ 2.88 (ddt, J=5.4, 4.1, 2.5 Hz, 2H), 2.73 (ddt, J=6.6, 4.6, 2.3 Hz, 2H), 1.88 (h, J=3.8, 3.3 Hz, 4H).

Step 3. Synthesis of 2-Chloro-N-(3-fluorophenyl)-5,6,7,8-tetrahydroquinazolin-4-amine (Compound C3, Scheme 1)

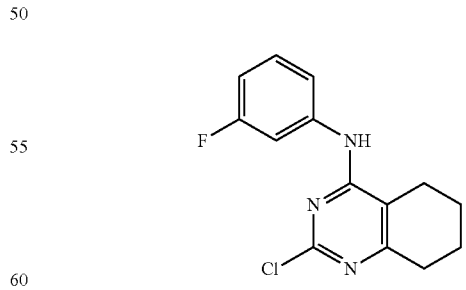

Titled compound was obtained using compound B3 (300 mg, 1.48 mmol) and 3-Fluoroaniline (0.16 ml, 1.21 mmol) following the general procedure C method 1 previously described at 120° C. for 72 h. Final normal phase purification (cyclohexane/AcOEt from 100:0 to 80:20) afforded pure title compound (115 mg, yield 28%). Rt=2.32 min (gradient 1); MS (ESI) m/z: 278.1/280.1 [M-H]+, [M-H]+ calculated: 278.1/280.1. $^1$H NMR (400 MHz, DMSO-$d_6$) δ 8.76 (s, 1H), 7.61 (dt, J=11.9, 2.3 Hz, 1H), 7.48 (ddd, J=8.2, 2.0, 0.9 Hz, 1H), 7.37 (m, 1H), 6.91 (tdd, J=8.5, 2.6, 0.9 Hz, 1H), 2.69-2.60 (m, 2H), 2.58-2.52 (m, 2H), 1.86-1.69 (m, 4H).

Step 4. Synthesis of N-(3-fluorophenyl)-2-(4-pyridyl)-5,6,7,8-tetrahydropyrido[4,3-d]pyrimidin-4-amine

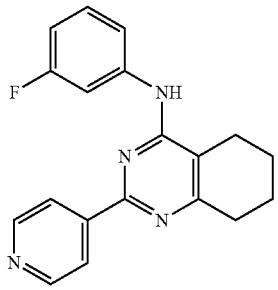 [SMILES: Fc1cccc(Nc2nc(-c3ccncc3)nc3c2CCCC3)c1]

Titled compound was obtained using compound C3 (110 mg, 0.40 mmol) and Pyridine-4-boronic acid (64.9 mg, 0.48 mmol) following the general procedure D previously described. Final normal phase purification (cyclohexane/AcOEt from 80:20 to 60:40) afforded pure title compound (65 mg, yield 51%). Rt=2.41 min (gradient 1); MS (ESI) m/z: 321.1 [M-H]+, [M-H]+ calculated: 321.1. 1H NMR (400 MHz, DMSO-$d_6$) δ 8.72-8.69 (m, 2H), 8.62 (s, 1H), 8.15-8.08 (m, 2H), 7.77 (dt, J=12.1, 2.3 Hz, 1H), 7.64 (dd, J=8.1, 1.8 Hz, 1H), 7.41 (td, J=8.2, 6.9 Hz, 1H), 6.90 (td, J=8.4, 2.6 Hz, 1H), 2.79 (t, J=5.9 Hz, 2H), 2.64 (t, J=5.8 Hz, 2H), 1.94-1.77 (m, 4H).

Example E5

Scheme 3

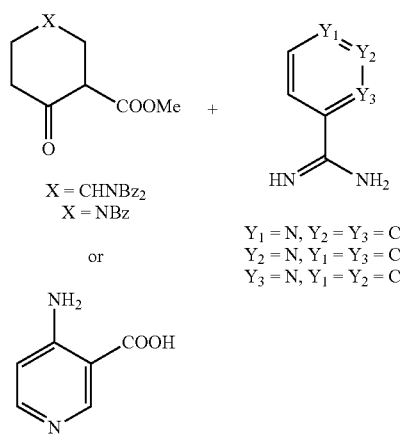

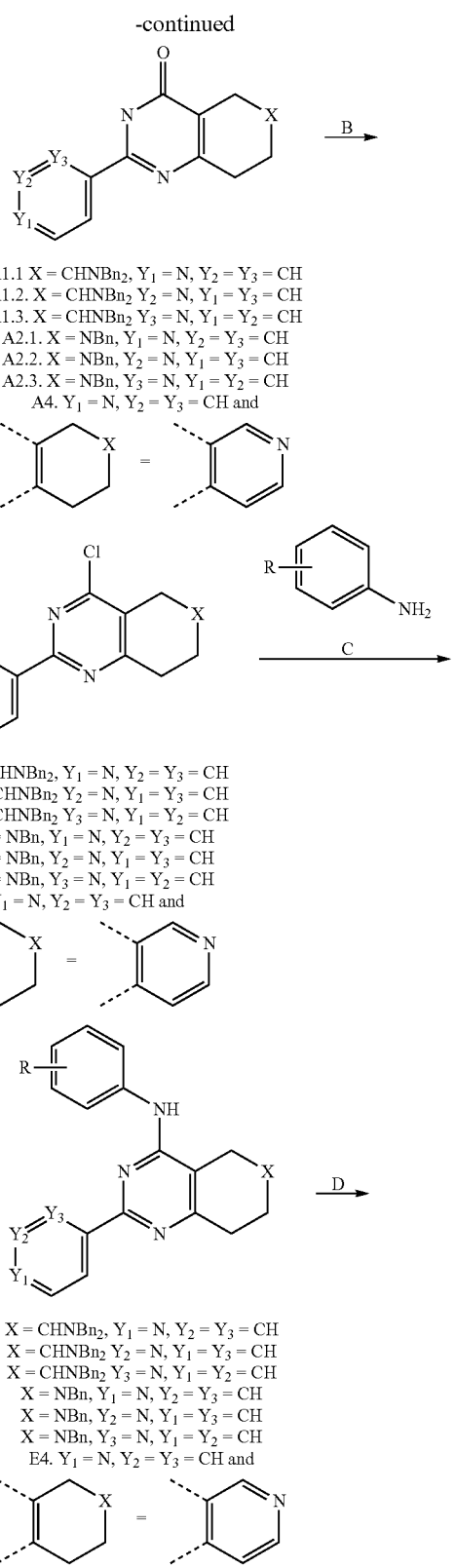

-continued

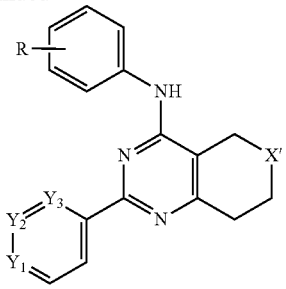

X' = CHNH$_2$, Y$_1$ = N, Y$_2$ = Y$_3$ = CH
X' = CHNH$_2$ Y$_2$ = N, Y$_1$ = Y$_3$ = CH
X' = CHNH$_2$ Y$_3$ = N, Y$_1$ = Y$_2$ = CH
X' = NH, Y$_1$ = N, Y$_2$ = Y$_3$ = CH
X' = NH, Y$_2$ = N, Y$_1$ = Y$_3$ = CH
X' = NH, Y$_3$ = N, Y$_1$ = Y$_2$ = CH

A. Method 1. MeONa, EtOH, reflux, 5 h. Method 2. NMP, Ar, 160° C., 72 h. B. Method 1: POCl$_3$, N$_2$, reflux, 5 h. Method 2: PCl$_5$, POCl$_3$, N$_2$, reflux, 5 h. C. Substituted aniline, rac-BINAP, PdOAc$_2$, Cs$_2$CO$_3$, 1,4-Dioxane, 100° C., microwave. D. HCOONH$_4$, Pd(OH)$_2$—C, MeOH, Ar, reflux.

General Procedure Reaction A Scheme 3. 2-pyrido-4-pyrimidone Fused Ring Formation Method 1.

A suspension of corresponding cyclic 2-oxo ethylester (1 mmol) in ethanol (4.5 ml), corresponding pyridinecarboxamidine hydrochloride (5 mmol) and sodium methoxide (5.5 mmol) was stirred at reflux temperature for 16 hours. Afterwards, the reaction crude was concentrated to dryness at low pressure, triturated in water (4.5 ml) and filtered. Resulting solid was then rinsed with methanol (0.5 ml) yielding titled compound.

Method 2.

A mixture of 4-Amino-nicotinic acid (1 mmol) and corresponding Pyridine-carboximidamide (5 mmol) in 1-metil-2-pirrolidone (1 ml) was stirred under Ar atmosphere at 160° C. for 72 hours. The reaction crude was poured in water (10 ml), the resulting solid filtered off and the filtrate concentrated at low pressure. Final normal phase purification yielded pure titled compound.

General Procedure Reaction B Scheme 3. 2-pyrido-4-pyrimidone Fused Ring Clorination Method 1.

A suspension of corresponding pyrimidone fused ring obtained from general procedure reaction A (1 mmol) in POCl$_3$ (1.5 ml) was stirred at 120° C. under N2 atmosphere until total solution was observed (around 4 hours). POCl$_3$ was then evaporated at low pressure, resulting residue solved in dichloromethane (15 ml), poured onto ice cold NaHCO$_3$ saturated solution (15 ml), organic layer separated, dried over Na$_2$SO$_4$ and concentrated to dryness at low pressure. Purification by normal phase chromatography finally yielded titled compound.

Method 2.

A mixture of corresponding pyrimidone fused ring (1 mmol), PCl$_5$ (1.1 mmol) and POCl$_3$ (30 mmol) was stirred under N$_2$ at 120° C. for 16 hours. The reaction crude was then concentrated to dryness at low pressure, portioned between DCM (15 ml) and cold NaHCO$_3$ saturated solution (45 ml), the organic layer dried over Na$_2$SO$_4$ and concentrated to dryness at low pressure, yielding pure titled compound.

General Procedure Reaction C Scheme 3. Aniline Introduction

A mixture of Pd(OAc)$_2$ (0.10 mmol) and rac-BINAP (0.10 mmol) in 1,4-dioxane (5 ml) was stirred under Ar flushing for 10 minutes. Then were stepwise added corresponding 2-chloro-4-pyrido-pyrimidine fused ring obtained from general procedure reaction B (1 mmol), corresponding substituted aniline (1.2 mmol) and Cs$_2$CO$_3$ (1.4 mmol). The reaction mixture was stirred in a CEM® microwave apparatus at 100° C. until reaction completion, filtrated through a celite coarse patch, rinsed with DCM and concentrated to dryness at low pressure. Final normal phase purification yielded titled compound.

General Procedure Reaction D Scheme 3. Benzyl Group Removal

Under N$_2$ atmosphere, a suspension of compound to be deprotected obtained from general procedure reaction C (1 mmol), ammonium formate (4 mmol), Pd(OH)$_2$/C (20% of starting material weight) was stirred at reflux temperature until reaction completion. Catalyst was filtered off trough a celite coarse patch and resulting filtrate concentrated to dryness at low pressure. Final normal phase purification yielded titled compound.

Synthesis of 6-(dibenzylamino)-2-(4-pyridyl)-5,6,7,8-tetrahydro-3H-quinazolin-4-one (Compound A1.1)

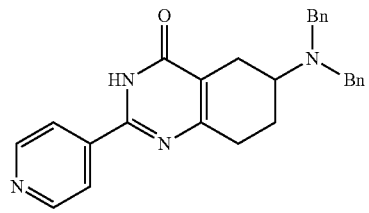 [SMILES: O=c1[nH]c(-c2ccncc2)nc2c1CC(N(Cc1ccccc1)Cc1ccccc1)CC2]

Titled compound was obtained using compound 1 (Scheme 1) (2000.0 mg, 5.69 mmol) and pyridine-4-carboxamidine hydrochloride (4624.0 mg, 28.46 mmol) following the general procedure A previously described and affording pure title compound (1620 mg, yield 67%). Rt=1.34 min (gradient 2); MS (ESI) m/z: 423.5 [M-H]$^+$, [M-H]$^+$ calculated: 423.2. $^1$H NMR (400 MHz, DMSO-d$_6$) δ 12.78 (s, 1H), 8.79-8.69 (m, 2H), 8.03-7.93 (m, 2H), 7.40 (d, J=7.1 Hz, 4H), 7.32 (t, J=7.5 Hz, 4H), 7.21 (t, J=7.3 Hz, 2H), 3.74 (d, J=14.2 Hz, 2H), 3.66 (d, J=14.2 Hz, 2H), 2.90-2.76 (m, 1H), 2.78-2.70 (m, 1H), 2.71-2.55 (m, 2H), 2.17-2.05 (m, 1H), 1.77 (qd, J=12.0, 5.4 Hz, 1H).

Synthesis of 6-(dibenzylamino)-2-(3-pyridyl)-5,6,7,8-tetrahydro-3H-quinazolin-4-one (Compound A1.2)

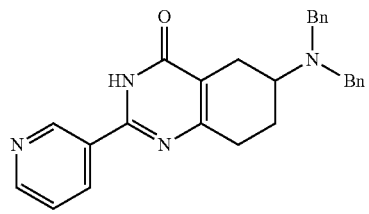 [SMILES: O=c1[nH]c(-c2cccnc2)nc2c1CC(N(Cc1ccccc1)Cc1ccccc1)CC2]

Titled compound was obtained using compound 1 (Scheme 1) (335.0 mg, 0.95 mmol) and pyridine-3-carboxamidine hydrochloride (795 mg, 4.77 mmol) following the general procedure A previously described and affording pure title compound (300 mg, yield 74%). Rt=1.30 min (gradient 2); MS (ESI) m/z: 423.5 [M-H]⁺, [M-H]⁺ calculated: 423.2. ¹H NMR (400 MHz, DMSO-d₆) δ 12.74 (s, 1H), 9.16 (d, J=2.3 Hz, 1H), 8.70 (dd, J=4.8, 1.6 Hz, 1H), 8.35 (dt, J=8.0, 2.0 Hz, 1H), 7.53 (dd, J=8.0, 4.8 Hz, 1H), 7.41 (d, J=6.8 Hz, 4H), 7.32 (t, J=7.5 Hz, 4H), 7.22 (t, J=7.3 Hz, 2H), 3.74 (d, J=14.2 Hz, 2H), 3.66 (d, J=14.2 Hz, 2H), 2.89-2.76 (m, 1H), 2.75-2.56 (m, 2H), 2.17-2.02 (m, 1H), 1.77 (qd, J=12.0, 5.4 Hz, 1H).

Synthesis of 6-(dibenzylamino)-2-(2-pyridyl)-5,6,7,8-tetrahydro-3H-quinazolin-4-one (Compound A1.3)

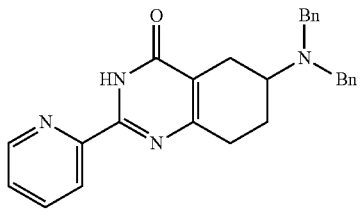 [SMILES: O=c1[nH]c(-c2ccccn2)nc2c1CC(N(Cc1ccccc1)Cc1ccccc1)CC2]

Titled compound was obtained using compound 1 (Scheme 1) (335.0 mg, 0.95 mmol) and pyridine-2-carboxamidine hydrochloride (774 mg, 4.77 mmol) following the general procedure A previously described and affording pure title compound (300 mg, yield 74%). Rt=1.89 min (gradient 2); MS (ESI) m/z: 423.5 [M-H]⁺, [M-H]⁺ calculated: 423.2. ¹H NMR (400 MHz, DMSO-d₆) δ 11.81 (s, 1H), 8.70 (dt, J=4.6, 1.3 Hz, 1H), 8.23 (d, J=7.9 Hz, 1H), 7.99 (td, J=7.8, 1.7 Hz, 1H), 7.60 (ddd, J=7.7, 4.7, 1.2 Hz, 1H), 7.43-7.36 (m, 4H), 7.31 (dd, J=8.3, 6.8 Hz, 4H), 7.25-7.15 (m, 2H), 3.73 (d, J=14.3 Hz, 2H), 3.65 (d, J=14.2 Hz, 2H), 2.91-2.76 (m, 1H), 2.73 (s, 1H), 2.70-2.54 (m, 2H), 2.12-2.05 (m, 1H), 1.77 (qd, J=12.0, 5.2 Hz, 1H).

Synthesis of 6-benzyl-2-(4-pyridyl)-3,5,7,8-tetrahydropyrido[4,3-d]pyrimidin-4-one (Compound A2.1)

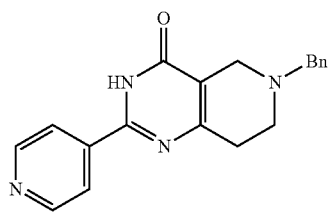 [SMILES: O=c1[nH]c(-c2ccncc2)nc2c1CN(Cc1ccccc1)CC2]

Titled compound was obtained using Methyl 1-benzyl-4-oxo-3-piperidinecarboxylate hydrochloride (1000.0 mg, 3.35 mmol) and pyridine-4-carboxamidine hydrochloride (2719.0 mg, 16.74 mmol) following the general procedure A previously described. Final normal phase purification, (DCM/DCM:MeOH 4:1 from 90/10 to 70/30) afforded pure title compound (655 mg, yield 61%). Rt=1.47 min (gradient 1); MS (ESI) m/z: 319.1 [M-H]⁺, [M-H]⁺ calculated: 319.1. ¹H NMR (400 MHz, DMSO-d₆) δ 12.82 (s, 1H), 8.77-8.73 (m, 2H), 8.03-7.98 (m, 2H), 7.40-7.34 (m, 4H), 7.32-7.24 (m, 1H), 3.70 (s, 2H), 3.27 (s, 2H), 2.74 (s, 4H).

Synthesis of 6-benzyl-2-(3-pyridyl)-3,5,7,8-tetrahydropyrido[4,3-d]pyrimidin-4-one (Compound A2.2)

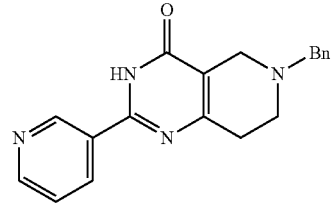 [SMILES: O=c1[nH]c(-c2cccnc2)nc2c1CN(Cc1ccccc1)CC2]

Titled compound was obtained using Methyl 1-benzyl-4-oxo-3-piperidinecarboxylate hydrochloride (250.0 mg, 0.84 mmol) and pyridine-3-carboxamidine hydrochloride (680 mg, 4.18 mmol) following the general procedure A previously described. Final normal phase purification, (DCM/DCM:MeOH 4:1 from 95/5 to 75/25) afforded pure title compound (185 mg, yield 69%). Rt=1.43 min (gradient 1); MS (ESI) m/z: 319.1 [M-H]⁺, [M-H]⁺ calculated: 319.1. ¹H NMR (400 MHz, DMSO-d₆) δ 12.73 (s, 1H), 9.18 (d, J=2.3 Hz, 1H), 8.65 (dd, J=4.8, 1.6 Hz, 1H), 8.37 (dt, J=8.0, 2.0 Hz, 1H), 7.56 (dd, J=8.0, 4.8 Hz, 1H), 7.39-7.32 (m, 4H), 7.33-7.26 (m, 1H), 3.70 (s, 2H), 3.28 (s, 2H), 2.74 (s, 4H).

Synthesis of 6-benzyl-2-(2-pyridyl)-3,5,7,8-tetrahydropyrido[4,3-d]pyrimidin-4-one (Compound A2.2)

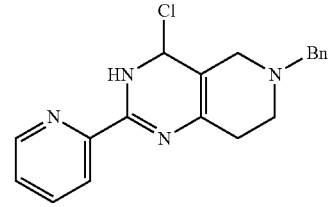 [SMILES: ClC1NC(c2ccccn2)=NC2=C1CN(Cc1ccccc1)CC2]

Titled compound was obtained using Methyl 1-benzyl-4-oxo-3-piperidinecarboxylate hydrochloride (250.0 mg, 0.84 mmol) and pyridine-2-carboxamidine hydrochloride (680 mg, 4.18 mmol) following the general procedure A previously described. Final normal phase purification, (DCM/DCM:MeOH 4:1 from 95/5 to 75/25) afforded pure title compound (185 mg, yield 69%). Rt=1.81 min (gradient 1); MS (ESI) m/z: 319.1 [M-H]⁺, [M-H]⁺ calculated: 319.1. ¹H NMR (400 MHz, DMSO-d₆) δ 11.95 (s, 1H), 8.72 (dt, J=4.8, 1.4 Hz, 1H), 8.28 (dt, J=7.9, 1.1 Hz, 1H), 8.02 (td, J=7.8, 1.8 Hz, 1H), 7.62 (ddd, J=7.6, 4.8, 1.2 Hz, 1H), 7.33-7.26 (m, 1H), 3.70 (s, 2H), 3.28 (s, 2H), 2.74 (s, 4H).

Synthesis of N,N-dibenzyl-4-chloro-2-(4-pyridyl)-5,6,7,8-tetrahydroquinazolin-6-amine (Compound B1.1)

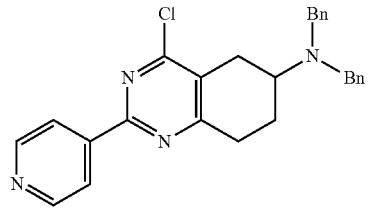 [SMILES: Clc1nc(-c2ccncc2)nc2c1CC(N(Cc1ccccc1)Cc1ccccc1)CC2]

Titled compound was obtained using compound A1.1 (Scheme 3) (1620.0 mg, 3.83 mmol) following the general procedure B previously described. Normal phase purification (CHCl$_3$/CHCl$_3$:MeOH 4:1 from 95/5 to 65/35) afforded pure title compound (1488 mg, yield 88%). Rt=2.67 min (gradient 2); MS (ESI) m/z: 441/443 [M-H]$^+$, [M-H]$^+$ calculated: 441/443. $^1$H NMR (400 MHz, DMSO-d$_6$) δ 8.99-8.89 (m, 2H), 8.55-8.39 (m, 2H), 7.73 (s, 2H), 7.62 (d, J=6.0 Hz, 2H), 7.51-7.26 (m, 6H), 4.72 (d, J=13.7 Hz, 2H), 4.60 (d, J=12.2 Hz, 2H), 3.84-3.68 (m, 1H), 3.62-3.50 (m, 1H), 3.47-3.32 (m, 1H), 3.25-3.17 (m, 1H), 3.09-2.91 (m, 1H), 2.81-2.64 (m, 1H), 2.29-2.11 (m, 1H).

Synthesis of N,N-dibenzyl-4-chloro-2-(3-pyridyl)-5,6,7,8-tetrahydroquinazolin-6-amine (Compound B1.2)

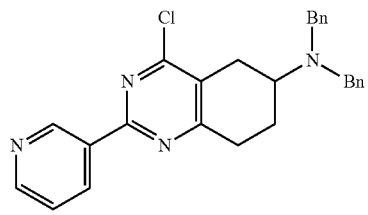 [SMILES: Clc1nc(-c2cccnc2)nc2c1CC(N(Cc1ccccc1)Cc1ccccc1)CC2]

Titled compound was obtained using compound A1.2 (Scheme 3) (300.0 mg, 0.71 mmol) following the general procedure B previously described. Normal phase purification (CHCl$_3$/CHCl$_3$:MeOH 4:1 from 100/0 to 50/50) afforded pure title compound (270 mg, yield 86%). Rt=2.64 min (gradient 2); MS (ESI) m/z: 441/443 [M-H]$^+$, [M-H]$^+$ calculated: 441/443. $^1$H NMR (400 MHz, CDCl$_3$) δ 9.55 (dd, J=2.2, 0.8 Hz, 1H), 8.68 (dd, J=4.8, 1.7 Hz, 1H), 8.61 (dt, J=8.0, 2.0 Hz, 1H), 7.42 (d, J=7.1 Hz, 4H), 7.37 (ddd, J=8.0, 4.8, 0.9 Hz, 1H), 7.35-7.28 (m, 4H), 7.26-7.19 (m, 2H), 3.83 (d, J=14.0 Hz, 2H), 3.71 (d, J=14.0 Hz, 2H), 3.22-2.96 (m, 3H), 2.94-2.75 (m, 2H), 2.38-2.22 (m, 1H), 1.84 (qd, J=12.2, 5.1 Hz, 1H).

Synthesis of N,N-dibenzyl-4-chloro-2-(2-pyridyl)-5,6,7,8-tetrahydroquinazolin-6-amine (Compound B1.3)

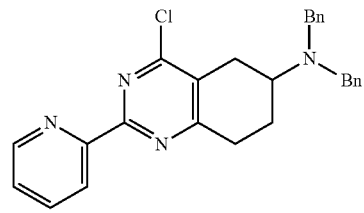 [SMILES: Clc1nc(-c2ccccn2)nc2c1CC(N(Cc1ccccc1)Cc1ccccc1)CC2]

Titled compound was obtained using compound A1.3 (Scheme 3) (300.0 mg, 0.71 mmol) following the general procedure B previously described. Normal phase purification (CHCl$_3$/CHCl$_3$:MeOH 4:1 from 100/0 to 50/50) afforded pure title compound (275 mg, yield 88%). Rt=2.29 min (gradient 2); MS (ESI) m/z: 441/443 [M-H]$^+$, [M-H]$^+$ calculated: 441/443. $^1$H NMR (400 MHz, CDCl$_3$) δ 8.82 (ddd, J=4.7, 1.8, 0.9 Hz, 1H), 8.44 (dt, J=8.0, 1.1 Hz, 1H), 7.82 (td, J=7.8, 1.8 Hz, 1H), 7.46-7.39 (m, 4H), 7.37 (ddd, J=7.5, 4.8, 1.2 Hz, 1H), 7.35-7.28 (m, 4H), 7.25-7.20 (m, 2H), 3.83 (d, J=14.0 Hz, 2H), 3.70 (d, J=14.1 Hz, 2H), 3.28 (ddd, J=18.3, 5.0, 2.5 Hz, 1H), 3.16-3.00 (m, 2H), 2.98-2.79 (m, 2H), 2.29 (ddd, J=12.5, 5.4, 2.6 Hz, 1H), 1.85 (qd, J=12.3, 5.0 Hz, 1H).

Synthesis of 6-benzyl-4-chloro-2-(4-pyridyl)-7,8-dihydro-5H-pyrido[4,3-d]pyrimidine (Compound B2.1)

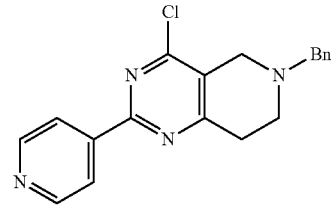 [SMILES: Clc1nc(-c2ccncc2)nc2c1CN(Cc1ccccc1)CC2]

Titled compound was obtained using compound A2.1 (Scheme 3) (650.0 mg, 2.04 mmol) following the general procedure B previously described. Normal phase purification (DCM/DCM:MeOH 4:1 from 100/0 to 80/20) afforded pure title compound (550 mg, yield 80%). Rt=2.59 min (gradient 1); MS (ESI) m/z: 337/339 [M-H]$^+$, [M-H]$^+$ calculated: 337/339. $^1$H NMR (400 MHz, DMSO-d$_6$) δ 8.79-8.73 (m, 2H), 8.20-8.14 (m, 2H), 7.46-7.34 (m, 4H), 7.34 (s, OH), 3.81 (s, 2H), 3.67 (s, 2H), 3.04 (t, J=5.8 Hz, 2H), 2.88 (d, J=5.9 Hz, 2H).

Synthesis of 6-benzyl-4-chloro-2-(3-pyridyl)-7,8-dihydro-5H-pyrido[4,3-d]pyrimidine (Compound B2.2)

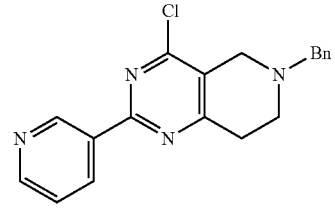 [SMILES: Clc1nc(-c2cccnc2)nc2c1CN(Cc1ccccc1)CC2]

Titled compound was obtained using compound A2.2 (Scheme 3) (180.0 mg, 0.57 mmol) following the general procedure B previously described. Normal phase purification (DCM/DCM:MeOH 4:1 from 100/0 to 80/20) afforded pure title compound (135 mg, yield 71%). Rt=2.53 min (gradient 1); MS (ESI) m/z: 337/339 [M-H]$^+$, [M-H]$^+$ calculated: 337/339. $^1$H NMR (400 MHz, DMSO-d$_6$) δ 9.21 (d, J=2.3 Hz, 1H), 8.64 (dd, J=4.8, 1.6 Hz, 1H), 8.35 (dt, J=8.0, 2.0 Hz, 1H), 7.53 (dd, J=8.0, 4.8 Hz, 1H), 7.46-7.34 (m, 4H), 7.34 (s, OH), 3.81 (s, 2H), 3.67 (s, 2H), 3.04 (t, J=5.8 Hz, 2H), 2.88 (d, J=5.9 Hz, 2H).

Synthesis of 6-benzyl-4-chloro-2-(2-pyridyl)-7,8-dihydro-5H-pyrido[4,3-d]pyrimidine (Compound B2.3)

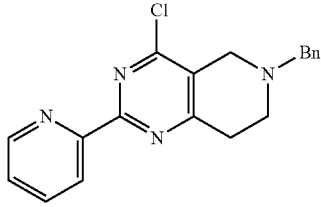 [SMILES: Clc1nc(-c2ccccn2)nc2c1CN(Cc1ccccc1)CC2]

Titled compound was obtained using compound A2.3 (Scheme 3) (180.0 mg, 0.57 mmol) following the general procedure B previously described. Normal phase purification (DCM/DCM:MeOH 4:1 from 90/10 to 0/100) afforded pure title compound (133 mg, yield 70%). Rt=2.34 min (gradient 1); MS (ESI) m/z: 337/339 [M-H]$^+$, [M-H]$^+$ calculated: 337/339. $^1$H NMR (400 MHz, DMSO-d$_6$) δ 8.75 (ddd, J=4.7, 1.8, 0.9 Hz, 1H), 8.33 (dt, J=8.0, 1.1 Hz, 1H), 7.98 (td, J=7.8, 1.8 Hz, 1H), 7.55 (ddd, J=7.6, 4.7, 1.2 Hz, 1H), 7.44-7.35 (m, 4H), 7.35-7.26 (m, 1H), 3.81 (s, 2H), 3.66 (s, 2H), 3.03 (t, J=5.8 Hz, 2H), 2.87 (t, J=5.8 Hz, 2H).

Example E4. N-(3-fluorophenyl)-2-(4-pyridyl)pyrido[4,3-d]pyrimidin-4-amine

Step 1. Synthesis of 2-(4-pyridyl)-3H-pyrido[4,3-d]pyrimidin-4-one (Compound A4 Scheme 3)

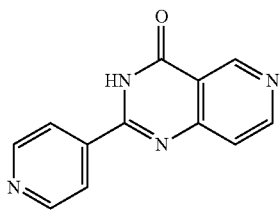 [SMILES: O=c1[nH]c(-c2ccncc2)nc2ccncc12]

Titled compound was obtained using 4-Amino-nicotinic acid (137 mg, 0.96 mmol) and Pyridine-4-carboximidamide (582.8 mg, 4.81 mmol) following the general procedure A method 2 previously described. The reaction crude was poured in water (10 ml), the resulting solid filtered off and the filtrate concentrated at low pressure. Final normal phase purification (DCM/DCM:MeOH 4:1 from 95:5 to 75:25) yielded pure titled compound (101 mg, yield 47%). Rt=1.10 min (gradient 1); MS (ESI) m/z: 225.4 [M-H]$^+$, [M-H]$^+$ calculated: 225.1. $^1$H NMR (400 MHz, DMSO-d$_6$) δ 13.10 (s, 1H), 9.33 (s, 1H), 8.88 (d, J=5.6 Hz, 1H), 8.82 (d, J=5.1 Hz, 2H), 8.10 (d, J=5.2 Hz, 2H), 7.68 (d, J=5.6 Hz, 1H).

Step 2. 4-chloro-2-(4-pyridyl)pyrido[4,3-d]pyrimidine (Compound B4 Scheme 3)

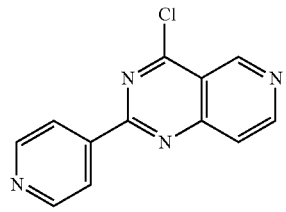 [SMILES: Clc1nc(-c2ccncc2)nc2ccncc12]

Titled compound was obtained using compound A4 (85 mg, 0.38 mmol) following the general procedure B method 2 previously described. The reaction crude was then concentrated to dryness at low pressure, portioned between DCM (5 ml) and cold NaHCO$_3$ saturated solution (15 ml), the organic layer dried over Na$_2$SO$_4$ and concentrated to dryness at low pressure, yielding pure titled compound (92 mg, yield 99%). Rt=1.74 min (gradient 1); MS (ESI) m/z: 243.3/245.3 [M-H]$^+$, [M-H]$^+$ calculated: 243.1/245.1. $^1$H NMR (400 MHz, Acetone-d$_6$) δ 9.72 (d, J=0.9 Hz, 1H), 9.10 (d, J=5.9 Hz, 1H), 8.92-8.80 (m, 2H), 8.49-8.40 (m, 2H), 8.05 (dd, J=5.9, 0.9 Hz, 1H).

Step 3. N-(3-fluorophenyl)-2-(4-pyridyl)pyrido[4,3-d]pyrimidin-4-amine (Compound E4 Scheme 3)

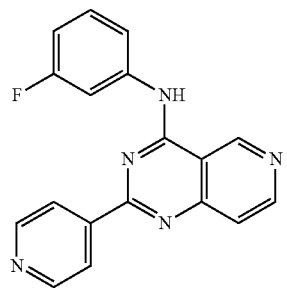 [SMILES: Fc1cccc(Nc2nc(-c3ccncc3)nc3ccncc23)c1]

Titled compound was obtained using compound B4 (92 mg, 0.38 mmol) and 3-Fluoroaniline (0.045 ml, 0.45 mmol) following the general procedure C previously described. Final normal phase purification (DCM/DCM:MeOH 4:1 from 100:0 to 60:40) yielded pure titled compound (61 mg, yield 50%). Rt=1.93 min (gradient 1); MS (ESI) m/z: 318.4 [M-H]$^+$, [M-H]$^+$ calculated: 318.1. $^1$H NMR (400 MHz, DMSO-d$_6$) δ 10.51 (s, 1H), 9.92-9.80 (m, 1H), 8.91-8.81 (m, 1H), 8.81-8.71 (m, 2H), 8.22 (dq, J=4.9, 1.6 Hz, 2H), 7.93-7.86 (m, 1H), 7.80-7.71 (m, 1H), 7.53 (tdd, J=8.2, 6.7, 1.3 Hz, 1H), 7.06 (td, J=8.5, 2.6 Hz, 1H).

Scheme 4

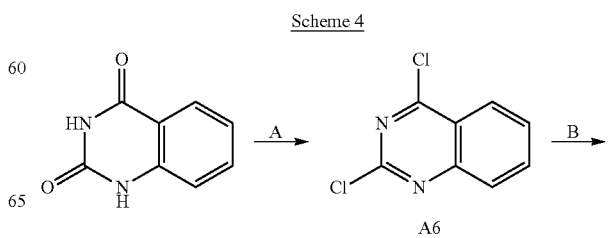

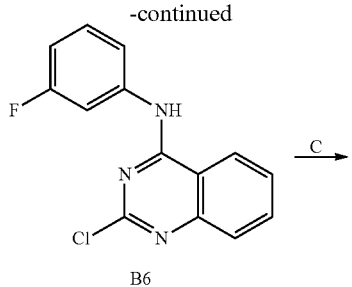

B6

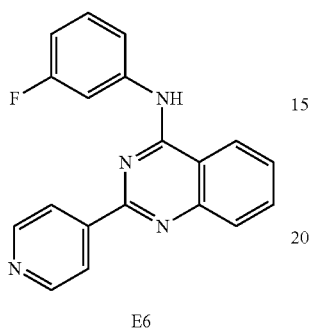

E6

Step 1. Synthesis of 2,4-dichloroquinazoline
(Compound A6, Scheme 4)

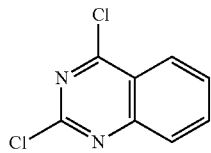

N,N-dimethylaniline (0.33 ml, 2.60 mmol), was dropwise added to an ice cold suspension of 1H-quinazoline-2,4-dione (200 mg, 1.23 mmol) in POCl$_3$ (1.15 ml). The reaction crude was then stirred at 120° C. under N$_2$ for 4 hours, cold to room temperature, poured onto ice cold water, the resulting solid filtrated and rinsed with cold water to finally yield titled compound (167 mg, yield 68%). $^1$H NMR (400 MHz, CDCl$_3$) δ 7.73-7.77 (m, 1H), 7.97-8.03 (m, 2H), 8.27 (d, 1H, J=8.4 Hz).

Step 2. Synthesis of
2-chloro-N-(3-fluorophenyl)quinazolin-4-amine
(Compound B6, Scheme 4)

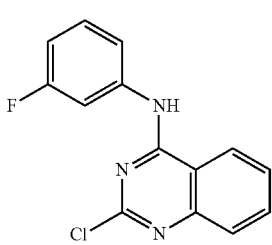 [SMILES: Fc1cccc(Nc2nc(Cl)nc3ccccc23)c1]

A solution of Compound A6 (115 mg, 0.58 mmol), 3-Fluoroaniline (0.056 ml, 0.58 mmol) and DIPEA (0.15 ml, 0.93 mmol) in a 4:1 iPrOH/DCM mixture (2.9 ml) was stirred at room temperature for 3 hours. Afterwards, the reaction crude was concentrated to dryness at low pressure, portioned between DCM (5 ml) and NaHCO$_3$ saturated solution (5 ml), the organic layer dried over Na$_2$SO$_4$ and concentrated to dryness at low pressure. Final normal phase purification (petroleum ether/AcOEt 3/2) yielded pure titled compound (53 mg, yield 34%). $^1$H NMR (400 MHz, CDCl$_3$) δ 6.90 (dt, 1H, J=2.2 Hz, J'=8.2 Hz), 7.34-7.39 (m, 1H), 7.45 (d, 1H), 7.58 (t, 1H, J=8.2 Hz), 7.77 (t, 1H, J=2 Hz), 7.80-7.86 (m, 2H), 7.88 (s, 1H), 7.94 (d, 1H, J=8 Hz).

Step 3. Synthesis of N-(3-fluorophenyl)-2-(4-pyridyl)quinazolin-4-amine (Example E6)

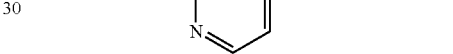

A suspension of Compound B6 (70 mg, 0.26 mmol), 4-pyridyl boronic acid (37.7 mg, 0.31 mmol), PdCl$_2$(dppf) dichloromethane complex (19.1 mg, 0.03 mmol) and K$_2$CO$_3$ 2 M solution (0.26 ml, 0.52 mmol) in 1,4-dioxane (2.6 ml) was stirred in a CEM® microwave apparatus at 100° C. for 30 min. Resulting crude was portioned between dichloromethane (15 ml), NaHCO$_3$ saturated solution (15 ml), the organic layer dried over Na$_2$SO$_4$ and concentrated to dryness at low pressure. Final normal phase purification (petroleum ether/AcOEt from 9/1 to 3/7) yielded pure title compound (54.7 mg, yield 68%). MS (ESI) m/z: 315.1 [M-H]$^-$. [M-H]$^-$ calculated: 315.1. $^1$H NMR (400 MHz, DMSO-d$_6$) δ 10.11 (s, 1H), 8.84-8.71 (m, 2H), 8.62 (dt, J=8.3, 1.1 Hz, 1H), 8.32-8.22 (m, 2H), 8.00-7.90 (m, 3H), 7.80 (ddd, J=8.2, 2.0, 0.9 Hz, 1H), 7.71 (ddd, J=8.3, 5.1, 3.1 Hz, 1H), 7.51 (td, J=8.2, 6.9 Hz, 1H), 7.01 (tdd, J=8.4, 2.6, 0.9 Hz, 1H).

The following are exemplary compounds according to Formula (I), (Ia) or (Ib) of the invention and their reported activity.

TABLE 2

Activity results

| Example | Structure | Activity Topo II IC$_{50}$ (μM) | Activity Cell IC$_{50}$ (μM) |
|---|---|---|---|
| E1.1 | (3-fluorophenyl)NH-; 2-(pyridin-4-yl)-5,6,7,8-tetrahydroquinazolin-4-amine with 6-NH$_2$ | 160 ± 20 | DU145: 15.1 ± 5.5<br>A549: 19.4 ± 1.8<br>HeLa: 17.0 ± 1.9<br>MCF7: 13.9 ± 2.3<br>A375: 9.9 ± 0.1<br>G361: 1.4 ± 0.4 |
| E1.2 | (3-fluorophenyl)NH-; 2-(pyridin-4-yl)-5,6,7,8-tetrahydroquinazolin-4-amine with (S)-6-NH$_2$ | 160 ± 20 | DU145: 17.9 ± 7.4<br>A549: 23.3 ± 2.3<br>HeLa: 17.1 ± 3.2<br>MCF7: 14.2 ± 2.5<br>A375: 10.7 ± 0.0<br>G361: 1.6 ± 0.5 |
| E1.3 | (3-fluorophenyl)NH-; 2-(pyridin-4-yl)-5,6,7,8-tetrahydroquinazolin-4-amine with (R)-6-NH$_2$ | 160 ± 20 | DU145: 11.1 ± 6.5<br>A549: 17.8 ± 0.6<br>HeLa: 21.8 ± 4.6<br>MCF7: 16.2 ± 2.6<br>A375: 10.8 ± 0.1<br>G361: 1.8 ± 0.6 |
| E1.4 | (3-methylphenyl)NH-; 2-(pyridin-4-yl)-5,6,7,8-tetrahydroquinazolin-4-amine with 6-NH$_2$ | 200 ± 20 | DU145: 12.3 ± 3.1<br>A549: 14.4 ± 0.1<br>HeLa: not available<br>MCF7: not available<br>A375: not available<br>G361: not available |
| E1.5 | (3-methoxyphenyl)NH-; 2-(pyridin-4-yl)-5,6,7,8-tetrahydroquinazolin-4-amine with 6-NH$_2$ | 170 ± 10 | DU145: 8.8 ± 1.5<br>A549: 26.2 ± 11.7<br>HeLa: not available<br>MCF7: not available<br>A375: not available<br>G361: not available |
| E1.6 | 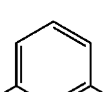 | >500 | DU145: 37.4 ± 1.5<br>A549: 75.9 ± 0.3<br>HeLa: not available |

The following are exemplary compounds according to Formula (I), (Ia) or (Ib) of the invention and their solubility and stability properties.

TABLE 3

Solubility and stability results

| Example | Structure | Solubility | Stability (t 1/2) |
| --- | --- | --- | --- |
| E1.1 | 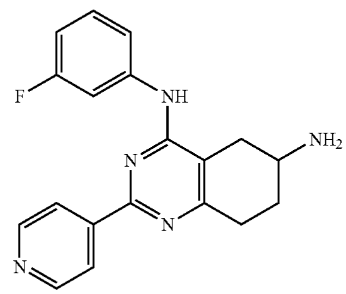 [SMILES: NC1CCc2nc(-c3ccncc3)nc(Nc3cccc(F)c3)c2C1] | Kinetic: >250 µM Termodinamic: not available | Mouse plasma: >120 min Mouse liver microsomes: >60 min |
| E1.2 | 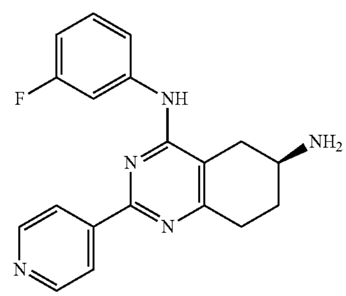 [SMILES: N[C@H]1CCc2nc(-c3ccncc3)nc(Nc3cccc(F)c3)c2C1] | Kinetic: >250 µM Termodinamic: not available | Mouse plasma: >120 min Mouse liver microsomes: not available |
| E1.3 | 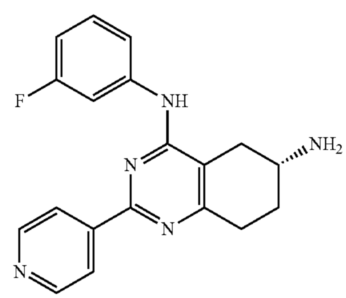 [SMILES: N[C@@H]1CCc2nc(-c3ccncc3)nc(Nc3cccc(F)c3)c2C1] | Kinetic: >250 µM Termodinamic: not available | Mouse plasma: >120 min Mouse liver microsomes: not available |
| E1.4 | 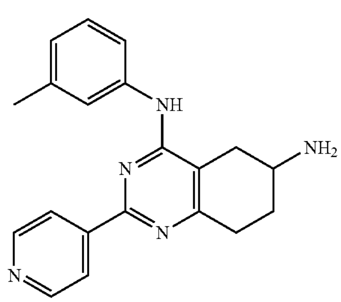 [SMILES: Cc1cccc(Nc2nc(-c3ccncc3)nc3c2CC(N)CC3)c1] | Kinetic: 249 ± 2 µM Termodinamic: not available | Mouse plasma: >120 min Mouse liver microsomes: not available |

TABLE 3-continued

Solubility and stability results

| Example | Structure | Solubility | Stability (t 1/2) |
|---|---|---|---|
| E1.5 | 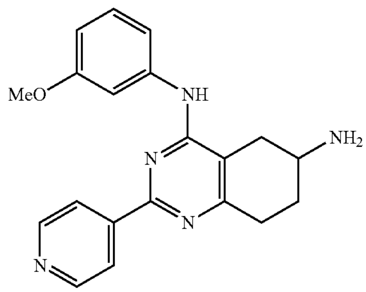 [SMILES: COc1cccc(Nc2nc(-c3ccncc3)nc3c2CC(N)CC3)c1] | Kinetic: >250 μM Termodinamic: not available | Mouse plasma: >120 min Mouse liver microsomes: not available |
| E1.6 | 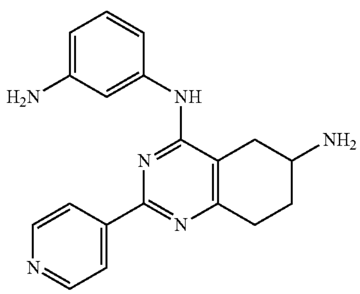 [SMILES: Nc1cccc(Nc2nc(-c3ccncc3)nc3c2CC(N)CC3)c1] | Kinetic: not available Termodinamic: not available | Mouse plasma: not available Mouse liver microsomes: not available |
| E1.7 | 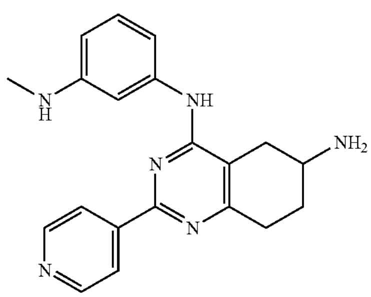 [SMILES: CNc1cccc(Nc2nc(-c3ccncc3)nc3c2CC(N)CC3)c1] | Kinetic: not available Termodinamic: not available | Mouse plasma: not available Mouse liver microsomes: not available |
| E1.8 | 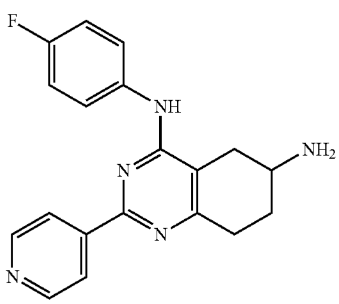 [SMILES: NC1CCc2nc(-c3ccncc3)nc(Nc3ccc(F)cc3)c2C1] | Kinetic: >250 μM Termodinamic: not available | Mouse plasma: >120 min Mouse liver microsomes: not available |
| E1.9 | 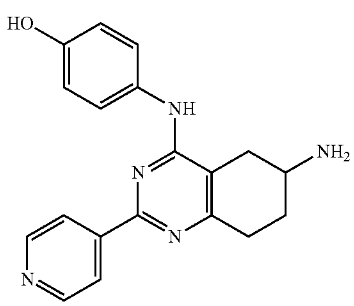 [SMILES: NC1CCc2nc(-c3ccncc3)nc(Nc3ccc(O)cc3)c2C1] | Kinetic: not available Termodinamic: not available | Mouse plasma: not available Mouse liver microsomes: not available |
| E1.10 | 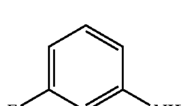 | Kinetic: 240 ± 13 μM Termodinamic: not available | Mouse plasma: >120 min Mouse liver microsomes: |

The invention claimed is:

1. A compound of Formula (Ia)

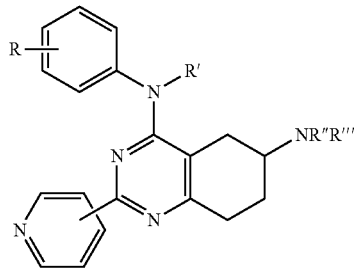

wherein R=H, $C_{1-6}$ alkyl, $C_{1-6}$ alkoxy, OH, NR"R'" and R'=H, $C_{1-6}$ alkyl;

R" and R'" are, independently, H, $C_{1-6}$ alkyl, $C_1$-$C_6$ alkylalkoxy or together may form a 4 to 7-membered heterocyclic ring with the nitrogen atom to which they are connected.

2. The compound of Formula according to claim 1, wherein R" and R'" are H.

3. The compound of Formula according to claim 1 which is selected from the group consisting of N4-(m-tolyl)-2-(4-pyridyl)-5,6,7,8-tetrahydroquinazoline-4,6-diamine (E1.4), N4-(3-methoxyphenyl)-2-(4-pyridyl)-5,6,7,8-tetrahydroquinazoline-4,6-diamine (E1.5), N4-(3-aminophenyl)-2-(4-pyridyl)-5,6,7,8-tetrahydroquinazoline-4,6-diamine (E1.6), N4-[3-(methylamino)phenyl]-2-(4-pyridyl)-5,6,7,8-tetrahydroquinazoline-4,6-diamine (E1.7), 4-[[6-amino-2-(4-pyridyl)-5,6,7,8-tetrahydroquinazolin-4-yl]amino]phenol (E1.9), and N4-[4-(dimethylamino)phenyl]-2-(4-pyridyl)-5,6,7,8-tetrahydroquinazoline-4,6-diamine (E1.11).

* * * * *

UNITED STATES PATENT AND TRADEMARK OFFICE
CERTIFICATE OF CORRECTION

PATENT NO. : 10,889,560 B2
APPLICATION NO. : 16/472593
DATED : January 12, 2021
INVENTOR(S) : Marco De Vivo It is certified that error appears in the above-identified patent and that said Letters Patent is hereby corrected as shown below:

In the Specification

At Column 72, please replace Table 2 with the following table:

Signed and Sealed this
Eighth Day of March, 2022

Drew Hirshfeld
*Performing the Functions and Duties of the
Under Secretary of Commerce for Intellectual Property and
Director of the United States Patent and Trademark Office*

| Table 2. Activity results | | | |
|---|---|---|---|
| Example | Structure | Activity Topo II $IC_{50}$ (μM) | Activity Cell $IC_{50}$ (μM) |
| E1.1 | | 160±20 | DU145: 15,1±5,5<br>A549: 19,4±1,8<br>HeLa: 17,0±1,9<br>MCF7: 13,9±2,3<br>A375: 9,9±0,1<br>G361: 1,4±0,4 |
| E1.2 | | 160±20 | DU145: 17,9±7,4<br>A549: 23,3±2,3<br>HeLa: 17,1±3,2<br>MCF7: 14,2±2,5<br>A375: 10,7±0,0<br>G361: 1,6±0,5 |
| E1.3 | | 160±20 | DU145: 11,1±6,5<br>A549: 17,8±0,6<br>HeLa: 21,8±4,6<br>MCF7: 16,2±2,6<br>A375: 10,8±0,1 |

| | | | |
|---|---|---|---|
| | | | G361: 1,8±0,6 |
| E1.4 | 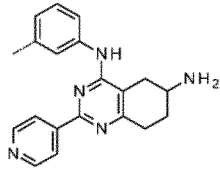 | 200±20 | DU145: 12,3±3,1<br>A549: 14,4±0,1<br>HeLa: not available<br>MCF7: not available<br>A375: not available<br>G361: not available |
| E1.5 | 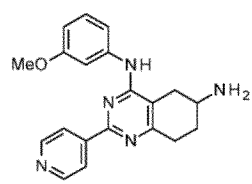 | 170±10 | DU145: 8,8±1,5<br>A549: 26,2±11,7<br>HeLa: not available<br>MCF7: not available<br>A375: not available<br>G361: not available |
| E1.6 | 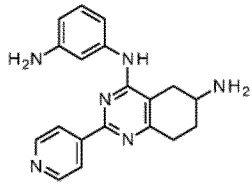 | >500 | DU145: 37,4±1,5<br>A549: 75,9±0,3<br>HeLa: not available<br>MCF7: not available<br>A375: not available<br>G361: not available |
| E1.7 | 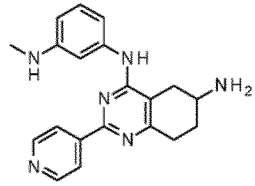 | >200 | DU145: 24,5±16,9<br>A549: 33,4 ±14,8<br>HeLa: not available<br>MCF7: not available<br>A375: not available<br>G361: not available |
| E1.8 | 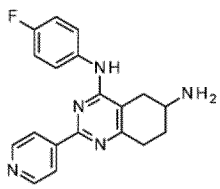 | 220±30 | DU145: 10,5±6,0<br>A549: 22,9±6,5<br>HeLa: not available<br>MCF7: not available<br>A375: not available<br>G361: not available |

| | | | |
|---|---|---|---|
| E1.9 | 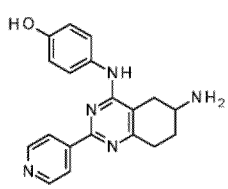 | >500 | DU145: 20,8±2,5<br>A549: 74,5±19,1<br>HeLa: not available<br>MCF7: not available<br>A375: not available<br>G361: not available |
| E1.10 | 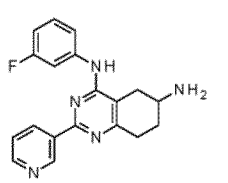 | 200±15 | DU145: 25,4±1,9<br>A549: 21,3±1,5<br>HeLa: not available<br>MCF7: not available<br>A375: not available<br>G361: not available |
| E1.11 | 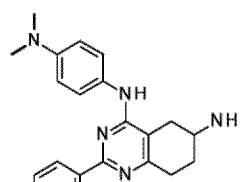 | 3.5±0.5 | DU145: not available<br>A549: not available<br>HeLa: not available<br>MCF7: not available<br>A375: not available<br>G361: not available |
| E2.1 | 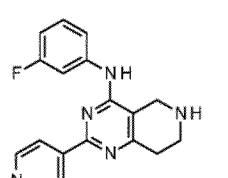 | 25±5 | DU145: 32,9±4,2<br>A549: 23,7±0,5<br>HeLa: 32,3±1,5<br>MCF7: 33,4±3,8<br>A375: 29,6±0,7<br>G361: 6,1±1,9 |
| E2.2 | 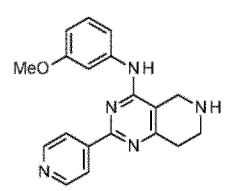 | 120±13 | DU145: 25,0±7,3<br>A549: 35,3±10,2<br>HeLa: not available<br>MCF7: not available<br>A375: not available<br>G361: not available |

| E2.3 | 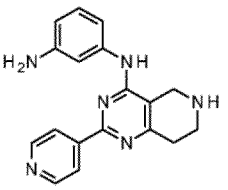 | 150±18 | DU145: 85,2±-<br>A549: 513,0±356,7<br>HeLa: not available<br>MCF7: not available<br>A375: not available<br>G361: not available |
|---|---|---|---|
| E2.4 | 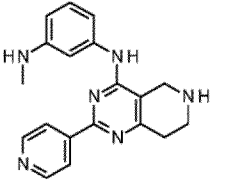 | 160±20 | DU145: 45,2±30,7<br>A549: 61,9±9,0<br>HeLa: not available<br>MCF7: not available<br>A375: not available<br>G361: not available |
| E2.5 | 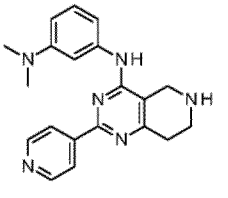 | 140±20 | DU145: 42,5±1,8<br>A549: 40,8 ± 3,3<br>HeLa: not available<br>MCF7: not available<br>A375: not available<br>G361: not available |
| E2.6 | 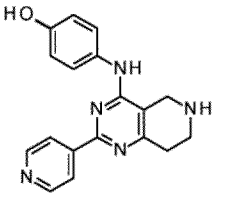 | 200±15 | DU145: not available<br>A549: not available<br>HeLa: not available<br>MCF7: not available<br>A375: not available<br>G361: not available |
| E2.7 | 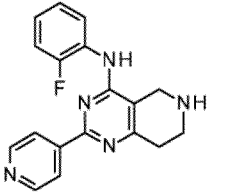 | 4.5±1 | DU145: not available<br>A549: not available<br>HeLa: not available<br>MCF7: not available<br>A375: not available<br>G361: not available |

| | | | |
|---|---|---|---|
| E3 | | 80±15 | DU145: 7,7±0,8<br>A549: 9,2±0,2<br>HeLa: 4,7±0,6<br>MCF7: 8,6±1,4<br>A375: 8,3±0,6<br>G361: 10,4±0,8 |
| E4 | | >200 | DU145: not available<br>A549: not available<br>HeLa: not available<br>MCF7: not available<br>A375: not available<br>G361: not available |
| E5 | | inactive | DU145: not available<br>A549: not available<br>HeLa: not available<br>MCF7: not available<br>A375: not available<br>G361: not available |
| E6 | | inactive | DU145: not available<br>A549: not available<br>HeLa: not available<br>MCF7: not available<br>A375: not available<br>G361: not available |

At Column 74-75, please replace Table 3 with the following table:

| Table 3. Solubility and stability results | | | |
|---|---|---|---|
| Example | Structure | Solubility | Stability (t ½) |
| E1.1 | | Kinetic: >250 µM Termodinamic: not available | Mouse plasma: >120 min Mouse liver microsomes: > 60 min |
| E1.2 | | Kinetic: >250 µM Termodinamic: not available | Mouse plasma: >120 min Mouse liver microsomes: not available |
| E1.3 | | Kinetic: >250 µM Termodinamic: not available | Mouse plasma: >120 min Mouse liver microsomes: not available |
| E1.4 | | Kinetic: 249 ± 2 µM Termodinamic: not available | Mouse plasma: >120 min Mouse liver microsomes: not available |
| E1.5 | | Kinetic: >250 µM Termodinamic: not available | Mouse plasma: >120 min Mouse liver microsomes: not available |

| | | | |
|---|---|---|---|
| E1.6 | 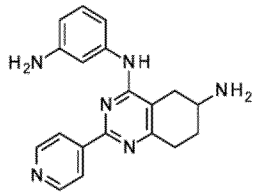 | Kinetic: not available Termodinamic: not available | Mouse plasma: not available Mouse liver microsomes: not available |
| E1.7 | 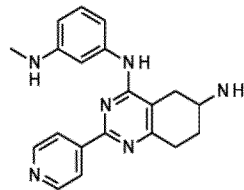 | Kinetic: not available Termodinamic: not available | Mouse plasma: not available Mouse liver microsomes: not available |
| E1.8 | 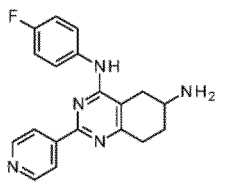 | Kinetic: >250 µM Termodinamic: not available | Mouse plasma: >120 min Mouse liver microsomes: not available |
| E1.9 | 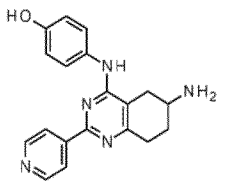 | Kinetic: not available Termodinamic: not available | Mouse plasma: not available Mouse liver microsomes: not available |
| E1.10 | 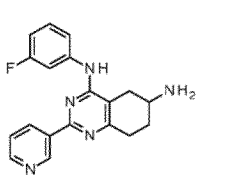 | Kinetic: 240 ± 13 µM Termodinamic: not available | Mouse plasma: >120 min Mouse liver microsomes: not available |
| E1.11 | 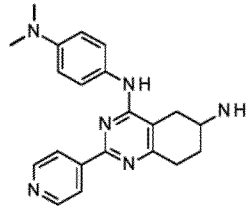 | Kinetic: >250 µM Termodinamic: 452 µM | Mouse plasma: >120 min Mouse liver microsomes: > 60 min |

| | | | |
|---|---|---|---|
| E2.1 | (3-fluorophenyl)amino tetrahydropyrido[3,4-d]pyrimidine with pyridyl | Kinetic: >250 µM  Termodinamic: 96 µM | Mouse plasma: >120 min  Mouse liver microsomes: 39 min |
| E2.2 | (3-methoxyphenyl)amino analog | Kinetic: >250 µM  Termodinamic: not available | Mouse plasma: >120 min  Mouse liver microsomes: not available |
| E2.3 | (3-aminophenyl)amino analog | Kinetic: >250 µM  Termodinamic: not available | Mouse plasma: >120 min  Mouse liver microsomes: not available |
| E2.4 | (3-methylaminophenyl)amino analog | Kinetic: >250 µM  Termodinamic: not available | Mouse plasma: >120 min  Mouse liver microsomes: not available |
| E2.5 | (3-dimethylaminophenyl)amino analog | Kinetic: >250 µM  Termodinamic: not available | Mouse plasma: >120 min  Mouse liver microsomes: not available |
| E2.6 | (4-hydroxyphenyl)amino analog | Kinetic: not available  Termodinamic: not available | Mouse plasma: not available  Mouse liver microsomes: not available |

| | | Kinetic: | Mouse plasma: |
|---|---|---|---|
| E2.7 | (structure) | >250 μM<br>Termodinamic: 596 μM | >120 min<br>Mouse liver microsomes: 30 min |
| E3 | (structure) | Kinetic:<br>17 ± 5 μM<br>Termodinamic: 0.2 μM | Mouse plasma:<br>89 min<br>Mouse liver microsomes: 22 min |
| E4 | (structure) | Kinetic:<br>not available<br>Termodinamic:<br>not available | Mouse plasma:<br>not available<br>Mouse liver microsomes:<br>not available |
| E5 | (structure) | Kinetic:<br>not available<br>Termodinamic:<br>not available | Mouse plasma:<br>not available<br>Mouse liver microsomes:<br>not available |
| E6 | (structure) | Kinetic:<br>not available<br>Termodinamic:<br>not available | Mouse plasma:<br>not available<br>Mouse liver microsomes:<br>not available |

In the Claims

At Claim 2, at Column 78, Line 1, please delete "Formula" and insert --Formula (Ia)-- in its place.

At Claim 3, at Column 78, Line 3, please delete "Formula" and insert --Formula (Ia)-- in its place.